(12) United States Patent
Flomenblit et al.

(10) Patent No.: US 10,953,141 B2
(45) Date of Patent: Mar. 23, 2021

(54) SHAPE CHANGE STRUCTURE

(71) Applicant: S.T.S. Medical Ltd., Misgav Business Park (IL)

(72) Inventors: Joseph Flomenblit, Petach-Tikva (IL); Gregory Frenklach, Modiln (IL)

(73) Assignee: S.T.S. Medical Ltd., Misgav Business Park (IL)

(*) Notice: Subject to any disclaimer, the term of this patent is extended or adjusted under 35 U.S.C. 154(b) by 153 days.

(21) Appl. No.: 14/893,069

(22) PCT Filed: May 23, 2014

(86) PCT No.: PCT/IL2014/050466
§ 371 (c)(1),
(2) Date: Nov. 22, 2015

(87) PCT Pub. No.: WO2014/188437
PCT Pub. Date: Nov. 27, 2014

(65) Prior Publication Data
US 2016/0101221 A1 Apr. 14, 2016

Related U.S. Application Data

(60) Provisional application No. 61/826,505, filed on May 23, 2013.

(51) Int. Cl.
*A61L 31/14* (2006.01)
*A61F 2/915* (2013.01)
(Continued)

(52) U.S. Cl.
CPC .............. *A61L 31/14* (2013.01); *A61F 2/844* (2013.01); *A61F 2/89* (2013.01); *A61F 2/91* (2013.01);
(Continued)

(58) Field of Classification Search
CPC .. A61F 2/89; A61F 2002/91591; A61F 2/844; A61F 2/82; A61F 2002/828;
(Continued)

(56) References Cited

U.S. PATENT DOCUMENTS 5,197,978 A  3/1993 Hess
5,336,163 A  8/1994 DeMane et al.
(Continued)

FOREIGN PATENT DOCUMENTS

CN  1210021  3/1999
CN  1252258  5/2000
(Continued)

OTHER PUBLICATIONS

Bansiddhi A., Dunand D. Shape-memory NiTi-Nb foams. Journal of Material Research. 2009;24(6):2107-2117. doi:10.1557/JMR.2009.0256.*

(Continued)

*Primary Examiner* — Kathleen S Holwerda
*Assistant Examiner* — Brooke Labranche

(57) ABSTRACT

An expandable structure comprising: a first shape memory (SM) portion which is in a strain-induced state; and a second portion which resists expansion of said structure due to said first portion, over a plurality of different expansion states of said first portion. Optionally, wherein said SM portion resists contraction of said structure due to forces applied by said second portion. Optionally or alternatively, said strain induced state is characterized by a SM portion expanding force decreasing as a function of strain of said SM portion, so as to have a difference of at least 10% in force between two strain states said structure is usable at.

35 Claims, 27 Drawing Sheets

(51) Int. Cl.
  *A61L 31/08* (2006.01)
  *A61L 31/02* (2006.01)
  *A61F 2/844* (2013.01)
  *A61F 2/89* (2013.01)
  *A61F 2/91* (2013.01)
  *A61L 31/06* (2006.01)
  *C22F 1/10* (2006.01)
  *A61F 2/82* (2013.01)
  *A61F 2/852* (2013.01)
  *A61F 2/958* (2013.01)

(52) U.S. Cl.
  CPC ............ *A61F 2/915* (2013.01); *A61L 31/022* (2013.01); *A61L 31/028* (2013.01); *A61L 31/06* (2013.01); *A61L 31/088* (2013.01); *A61L 31/146* (2013.01); *C22F 1/10* (2013.01); *A61F 2/852* (2013.01); *A61F 2/958* (2013.01); *A61F 2002/828* (2013.01); *A61F 2002/91508* (2013.01); *A61F 2002/91558* (2013.01); *A61F 2210/0019* (2013.01); *A61F 2250/0042* (2013.01); *A61L 2400/16* (2013.01)

(58) Field of Classification Search
  CPC .. A61F 2002/91508; A61F 2002/91558; A61F 2210/0019; A61F 2250/0042; A61L 31/14; A61L 31/022; A61L 31/028; A61L 31/06; A61L 31/088; A61L 31/146; A61L 2400/16
  See application file for complete search history.

(56) References Cited

U.S. PATENT DOCUMENTS

| | | | |
|---|---|---|---|
| 5,441,515 A | 8/1995 | Khosravi et al. | |
| 5,637,113 A | 6/1997 | Tartaglia et al. | |
| 5,693,065 A | 12/1997 | Rains, III | |
| 5,876,434 A | 3/1999 | Flomenblit et al. | |
| 5,882,444 A | 3/1999 | Flomenblit et al. | |
| 5,899,935 A | 5/1999 | Ding | |
| 5,964,770 A * | 10/1999 | Flomenblit | A61B 17/68 |
| | | | 604/530 |
| 6,083,259 A | 7/2000 | Frantzen | |
| 6,086,610 A | 7/2000 | Duerig et al. | |
| 7,361,168 B2 | 4/2008 | Makower et al. | |
| 7,410,480 B2 | 8/2008 | Muni et al. | |
| 7,645,272 B2 | 1/2010 | Chang et al. | |
| 7,654,997 B2 | 2/2010 | Makower et al. | |
| 7,771,409 B2 | 8/2010 | Chang et al. | |
| 7,803,150 B2 | 9/2010 | Chang et al. | |
| 8,025,635 B2 | 9/2011 | Eaton et al. | |
| 8,585,731 B2 | 11/2013 | Abbate et al. | |
| 2001/0056296 A1 | 12/2001 | Sugita et al. | |
| 2002/0002400 A1 | 1/2002 | Drasler et al. | |
| 2003/0004563 A1 | 1/2003 | Jackson et al. | |
| 2003/0036792 A1 * | 2/2003 | Richter | A61F 2/91 |
| | | | 623/1.12 |
| 2003/0149472 A1 | 8/2003 | Pinchuk et al. | |
| 2005/0004647 A1 | 1/2005 | Bassoe | |
| 2005/0251193 A1 | 11/2005 | Lary | |
| 2006/0020324 A1 | 1/2006 | Schmid et al. | |
| 2006/0106361 A1 | 5/2006 | Muni et al. | |
| 2006/0184231 A1 | 8/2006 | Rucker | |
| 2008/0009936 A1 | 1/2008 | Kim et al. | |
| 2008/0077240 A1 | 3/2008 | Saidi | |
| 2008/0147164 A1 | 6/2008 | Gale et al. | |
| 2008/0188924 A1 | 8/2008 | Prabhu | |
| 2008/0200974 A1 | 8/2008 | Trauthen et al. | |
| 2008/0300668 A1 | 12/2008 | Bonsignore | |
| 2009/0036968 A1 | 2/2009 | Hepworth et al. | |
| 2009/0099639 A1 | 4/2009 | Sabaria | |
| 2009/0266365 A1 | 10/2009 | Oberle | |
| 2010/0010622 A1 * | 1/2010 | Lowe | A61F 2/91 |
| | | | 623/1.16 |
| 2011/0112512 A1 | 5/2011 | Muni et al. | |
| 2012/0046756 A1 | 2/2012 | Wang et al. | |
| 2013/0053946 A1 | 2/2013 | Stinson | |
| 2013/0096666 A1 * | 4/2013 | Bregulla | A61L 31/022 |
| | | | 623/1.15 |
| 2014/0243950 A1 | 8/2014 | Weiner | |
| 2014/0277072 A1 | 9/2014 | Suehara | |
| 2014/0296957 A1 | 10/2014 | Janzten et al. | |
| 2018/0360626 A1 | 12/2018 | Yaniv et al. | |

FOREIGN PATENT DOCUMENTS

| | | |
|---|---|---|
| CN | 1269845 | 10/2000 |
| CN | 101048526 | 10/2007 |
| CN | 101189016 | 5/2008 |
| CN | 101612074 | 12/2009 |
| CN | 102805676 | 12/2012 |
| CN | 102973340 | 3/2013 |
| DE | 10226734 | 11/2003 |
| EP | 2298317 | 3/2011 |
| EP | 2298318 | 3/2011 |
| EP | 2298319 | 3/2011 |
| EP | 2512578 | 10/2012 |
| GB | 2343119 | 5/2000 |
| JP | 2000-135290 | 5/2000 |
| JP | 2001-510084 | 7/2001 |
| JP | 2001-511666 | 8/2001 |
| JP | 2001-525013 | 12/2001 |
| JP | 2008-850349 | 3/2008 |
| JP | 2008-113958 | 5/2008 |
| JP | 2012-034896 | 2/2012 |
| WO | WO 95/26695 | 10/1995 |
| WO | WO 95/31945 | 11/1995 |
| WO | WO 98/28035 | 7/1998 |
| WO | WO 99/04053 | 1/1999 |
| WO | WO 99/16385 | 4/1999 |
| WO | WO 99/20205 | 4/1999 |
| WO | WO 00/10485 | 3/2000 |
| WO | WO 00/24338 | 5/2000 |
| WO | WO 00/32136 | 6/2000 |
| WO | WO 01/01888 | 1/2001 |
| WO | WO 01/85064 | 11/2001 |
| WO | WO 03/020175 | 3/2003 |
| WO | WO 03/034940 | 5/2003 |
| WO | WO 2005/053576 | 6/2005 |
| WO | WO 2005/096992 | 10/2005 |
| WO | WO 2006/014699 | 2/2006 |
| WO | WO 2006/107957 | 10/2006 |
| WO | WO 2007/054014 | 5/2007 |
| WO | WO 2010/107681 | 9/2010 |
| WO | WO 2010/120532 | 10/2010 |
| WO | WO 2011/127452 | 10/2011 |
| WO | WO 2012/011269 | 1/2012 |
| WO | WO 2012/173995 | 12/2012 |
| WO | WO 2013/032494 | 3/2013 |
| WO | WO 2014/188437 | 11/2014 |
| WO | WO 2016/084087 | 6/2016 |

OTHER PUBLICATIONS

Notification of Office Action dated Aug. 14, 2017 From the State Intellectual Property Office of the People's Republic of China Re. Application No. 201480041307.4 With Summary in English. (6 Pages).

Invitation to Pay Additional Fees dated May 20, 2016 From the International Searching Authority Re. Application No. PCT/IL2015/051153.

Examination Report dated May 2, 2017 From the Australian Government, IP Australia Re. Application No. 2014269936. (3 Pages).

Translation of Notification of Office Action dated Jan. 20, 2017 From the State Intellectual Property Office of the People's Republic of China Re. Application No. 201480041307.4. (1 Page).

Notification of Office Action dated Jan. 20, 2017 From the State Intellectual Property Office of the People's Republic of China Re. Application No. 201480041307.4. (3 Pages).

(56) References Cited

OTHER PUBLICATIONS

Communication Relating to the Results of the Partial International Search dated Oct. 7, 2014 From the International Searching Authority Re. Application No. PCT/IL2014/050466.
International Preliminary Report on Patentability dated Dec. 3, 2015 From the International Bureau of WIPO Re. Application No. PCT/IL2014/050466.
International Search Report and the Written Opinion dated Feb. 3, 2015 From the International Searching Authority Re. Application No. PCT/IL2014/050466.
Vermette et al. "Biomedical Degradation of Polyurethanes", Biomedical Applications of Polyurethanes, 6(Chap.5): 97-159, 2001.
Translation of Notification of Office Action dated Aug. 14, 2017 From the State Intellectual Property Office of the People's Republic of China Re. Application No. 201480041307.4. (2 Pages).
International Preliminary Report on Patentability dated Jun. 8, 2017 From the International Bureau of WIPO Re. Application No. PCT/IL2015/051153. (15 Pages).
International Search Report and the Written Opinion dated Aug. 5, 2016 From the International Searching Authority Re. Application No. PCT/IL2015/051153.
Notification of Office Action and Search Report dated Feb. 27, 2018 From the State Intellectual Property Office of the People's Republic of China Re. Application No. 201480041307.4 and its Translation of Office Action Into English. (6 Pages).
Translation dated Apr. 22, 2018 of Notice of Reason for Rejection dated Apr. 3, 2018 From the Japan Patent Office Re. Application No. 2016-514534. (4 Pages).
Notice of Reason for Rejection dated Apr. 3, 2018 From the Japan Patent Office Re. Application No. 2016-514534 and its Summary in English. (5 Pages).
Communication Pursuant to Article 94(3) EPC dated Mar. 22, 2018 From the European Patent Office Re. Application No. 14738907.6. (7 Pages).
Translation dated Sep. 4, 2018 of Notice of Decision of Refusal dated Aug. 21, 2018 From the Japan Patent Office Re. Application No. 2016-514534. (3 Pages).
Restriction Official Action dated Mar. 29, 2019 From the US Patent and Trademark Office Re. U.S. Appl. No. 15/529,551. (10 pages).
Communication Pursuant to Article 94(3) EPC dated Apr. 16, 2019 From the European Patent Office Re. Application No. 14738907.6. (8 Pages).
Notice of Reason for Rejection dated Nov. 19, 2019 From the Japan Patent Office Re. Application No. 2014-513308 and a Summary in English. (5 Pages).
Official Action dated Sep. 19, 2019 From the US Patent and Trademark Office Re. U.S. Appl. No. 15/529,551. (51 pages).
Translation dated Dec. 5, 2019 of Notice of Reasons for Refusal dated Nov. 19, 2019 From the Japan Patent Office Re. Application No. 2014-513308. (5 Pages).
Communication Pursuant to Article 94(3) EPC dated Feb. 21, 2020 From the European Patent Office Re. Application No. 14738907.6. (7 Pages).
Interview Summary dated May 21, 2020 from the US Patent and Trademark Office Re. U.S. Appl. No. 15/529,551. (3 pages).
Requisition by the Examiner dated Jun. 5, 2020 From the Innovation, Science and Economic Development Canada, Canadian Intellectual Property Office Re. Application No. 2,911,226.
Final Official Action dated Apr. 17, 2020 from the US Patent and Trademark Office Re. U.S. Appl. No. 15/529,551. (25 pages).
Notice of Reasons for Rejection dated Aug. 21, 2018 From the Japan Patent Office Re. Application No. 2016-514534. (3 Pages).

* cited by examiner

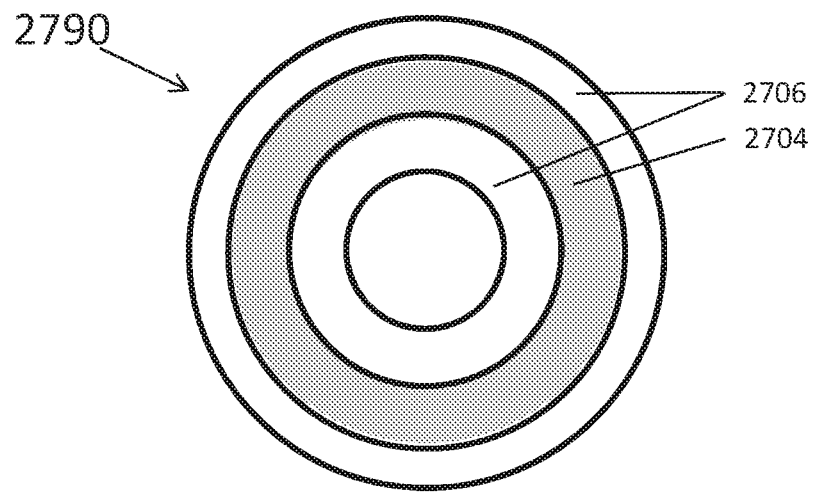
FIG. 27
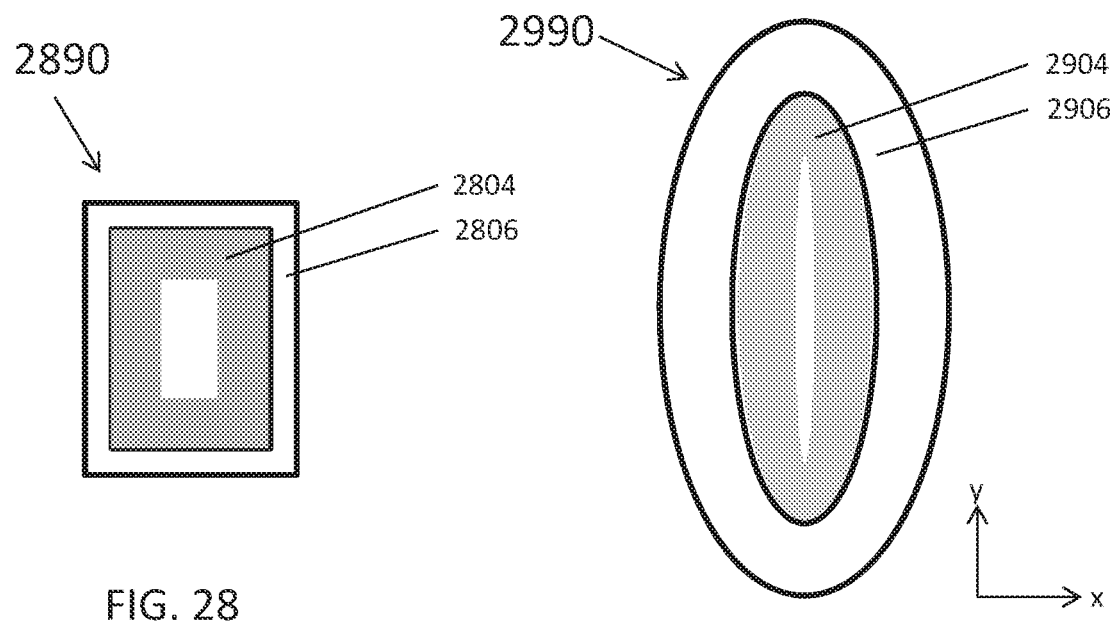
FIG. 28
FIG. 29

SHAPE CHANGE STRUCTURE

RELATED APPLICATIONS

This application is a National Phase of PCT Patent Application No. PCT/IL2014/050466 having International filing date of May 23, 2014, which claims the benefit of priority under 35 USC § 119(e) of U.S. Provisional Patent Application No. 61/826,505 filed on May 23, 2013 The contents of the above applications are all incorporated by reference as if fully set forth herein in their entirety.

FIELD AND BACKGROUND OF THE INVENTION

The present invention, in some embodiments thereof, relates to an expandable structure and, more particularly, but not exclusively, to an expandable structure for deployment in a lumen.

Expandable structures, for example, stents, are used in the body for a various applications. Common stents include self-expanding stents formed of elastic or shape-memory materials and balloon expanding stents formed of plastically deformable materials.

Stents of the art include composite stents, U.S. Pat. No. 5,964,770, the disclosure of which is incorporated herein by reference, describes "A medical device such as a stent, surgical staple, bone anchoring device or bone fixation device, intended to be deployed within the body, composes a shape memory alloy (SMA) portion with an austenitic and unaustenitic state with different memorized configurations in each of these states. The SMA which is initially in an initial configuration in which it can be placed into position within the body, can be mechanically deformed into an operational configuration in which it remains deployed within the body."

U.S. Pat. No. 5,876,434, the disclosure of which is incorporated herein by reference, describes "A medical device which comprises a shape memory alloy (SMA) portion which is deformable from an undeformed first configuration assumed by it in an austenitic state of the SMA to a deformed second configuration, whereby the SMA is converted into a strain-induced martensite or partial martensite. This conversion increases the temperature of transformation (As) from an initial transformation temperature As° to a temperature As'. When the SMA, once in the second configuration, is heated to a temperature higher than As', it transforms to an at least partial austenite and it transforms towards the undeformed first configuration with a decrease of As from As' to As°. As° is below body temperature such that when the device is deployed in the body, after placing it in its target location with the SMA portion in the second configuration and then heating it to assume its first configuration, the SMA is stable in the at least partial austenite at body temperature."

Additional background art includes U.S. Pat. No. 6,086,610, International Patent Application No. WO0032136, International Patent Application No. WO05053576, International Patent Application No. WO06014699, U.S. Patent Application Publication No. US2008188924, U.S. Patent Application Publication No. US2008300668, International Patent Application No. WO10107681, International Patent Application No. WO11127452, International Patent Application No. WO9526695, U.S. Pat. No. 5,637,113, International Patent Application No. WO0024338, International Patent Application No. WO0101888, International Patent Application No. WO12011269, International Patent Application No. WO13032494, U.S. Patent Application Publication No. US2005004647 U.S. Pat. No. 5,441,515, International Patent Application No. WO10120532, International Patent Application No. WO9920205, U.S. Pat. No. 5,899,935, International Patent Application No. WO03034940, DE10226734, U.S. Patent Application Publication No. US2008147164, International Patent Application No. WO03020175, International Patent Application No. WO05096992, CN102973340, International Patent Application No. WO12173995, International Patent Application No. WO07054014, International Patent Application No. WO0185064, International Patent Application No. WO9531945, U.S. Pat. No. 6,083,259, U.S. Patent Application Publication No. US2001056296, and International Patent Application No. WO0010485, the disclosures of all of which are herein incorporated in their entirety by reference into the specification, to the same extent as if each individual publication, patent or patent application was specifically and individually indicated to be incorporated herein by reference.

SUMMARY OF THE INVENTION

There is provided in accordance with an exemplary embodiment of the invention, an expandable structure comprising:

a first shape memory (SM) portion which is in a strain-induced state; and a second portion which resists expansion of said structure due to said first portion, over a plurality of different expansion states of said first portion.

In an exemplary embodiment of the invention, wherein said SM portion resists contraction of said structure due to forces applied by said second portion. Optionally or alternatively, said strain induced state is characterized by a SM portion expanding force decreasing as a function of strain of said SM portion, so as to have a difference of at least 10% in force between two strain states said structure is usable at. Optionally, said difference is at least 20%.

In an exemplary embodiment of the invention, said second portion both resists expansion of said SM portion and said SM portion resists contraction of said second portion, due to said strain-induced state selectively reducing a force applied by said SM portion at different deployment stages thereof.

In an exemplary embodiment of the invention, the structure is tubular and said SM portion and said second portion are tubular and wherein said SM portion defines an expanding force which decreases as a function of strain of said SM portion; wherein the expandable structure is stable in both a crimped state and a deployed state thereof, where a diameter of the structure in said deployed state is larger than a diameter of said structure in said crimped state; and wherein said structure is stable when a SM portion expanding force is less than a maximum resistive force of said second portion. Optionally, said second portion tube encloses said SM portion tube.

In an exemplary embodiment of the invention, the structure is tubular and said SM portion and said second portion are tubular and wherein said SM portion defines an expanding force which decreases as a function of strain of said SM portion; wherein the expandable structure is substantially stable in both a crimped state and a deployed state thereof, where a diameter of the structure in said deployed state is larger than a diameter of said structure in said crimped state; and wherein said structure is considered substantially stable when a SM portion expanding force at most 10% more than a maximum resistive force of said second portion.

Optionally or alternatively, said second portion is configured to contract when said structure is in a deployed state, and wherein said structure is stable when a second portion contracting force is less than a resisting force of said first portion. Optionally, said second portion is configured to elastically contract when deployed.

In an exemplary embodiment of the invention according to any of the described herein embodiments, said structure includes stable configurations wherein said SM portion expanding force is balanced to within 10% by said second portion contracting force.

In an exemplary embodiment of the invention according to any of the described herein embodiments, said balanced structure exerts less outwards force than 30% of said SM portion expanding force, at a deployed stable configuration.

In an exemplary embodiment of the invention according to any of the described herein embodiments, said structure is stable over a range of deployed in a range of structure strains where said SM portion expanding force is smaller than said second portion resistive force. Optionally, said tubular SM portion is treated such that said SM portion has a shape memory diameter at a section thereof;
wherein said tubular second portion has a second portion relaxed diameter at an axially a corresponding section thereof; and
wherein stable expandable structure diameters are between said SM shape memory diameter and said second portion relaxed diameter.

In an exemplary embodiment of the invention according to any of the described herein embodiments, said SM portion is pre-treated to have said decrease in SM portion relaxation force as a function of strain applied to said SM portion. Optionally, said pre-treatment consists a treatment selected from memorizing treatment, solution treatment, ageing treatment and combinations thereof.

In an exemplary embodiment of the invention according to any of the described herein embodiments, said SM portion is treated such that, in a crimped state, an austenite transformation finish temperature of at least 10% thereof is at least 5° C. above an austenite transformation finish temperature in a deployed state.

In an exemplary embodiment of the invention according to any of the described herein embodiments, said SM portion is treated such that, in a crimped state, an austenite transformation finish temperature of at least 10% thereof is at least 10° C. above an austenite transformation finish temperature in a deployed state.

In an exemplary embodiment of the invention according to any of the described herein embodiments, said SM portion is treated such that, in a crimped state, an austenite transformation finish temperature of at least 10% thereof is at least 15° C. above an austenite transformation finish temperature in a deployed state.

In an exemplary embodiment of the invention according to any of the described herein embodiments, said SM portion and second portion are selected so that said structure has a resistance to a crimping force acting to radially crimp the structure equal to at least 40% of a self-expansion force of said SM portion.

In an exemplary embodiment of the invention according to any of the described herein embodiments, said SM portion and second portion are selected so that said structure has a resistance to a crimping force acting to radially crimp the structure equal to at least 100% of a force required to expand the stent.

In an exemplary embodiment of the invention according to any of the described herein embodiments, said SM portion and second portion are selected so that said structure elastically deforms upon application of a low strain which changes a circumference of said structure by less than 5%.

In an exemplary embodiment of the invention according to any of the described herein embodiments, said SM portion and second portion are selected so that said structure exhibits a ratio of at least 10 between radially applied force (smaller) and crush resistance (larger).

In an exemplary embodiment of the invention according to any of the described herein embodiments, said SM portion has a surface coverage percentage which is less than 50% of a surface coverage of said second portion.

In an exemplary embodiment of the invention according to any of the described herein embodiments, said SM portion has a relaxed diameter of more than 100% of a relaxed diameter of said second portion.

In an exemplary embodiment of the invention according to any of the described herein embodiments, said SM portion uses a joint deformation mechanism to deploy and said second portion uses a strut deformation and/or elongation mechanism during deployment.

In an exemplary embodiment of the invention according to any of the described herein embodiments, the structure is in the form of a plurality of segments, each comprising
a said tubular SM portion; and
a said tubular second portion restraining said tubular SM portion; and
a plurality of connectors, each connector axially coupling two segments;
wherein a diameter of each said segment in said deployed state is radially expandable. Optionally, said plurality of connectors comprise shape memory material. Optionally or alternatively, said plurality of connectors comprise polymer material. Optionally or alternatively, each said second portion and each said connector are formed as a single tubular component. Optionally, at least one section of said single tubular component is configured to radially contract at at least one location where not overlapping with said SM portions and at least assist in preventing axial motion of said SM portion relative to said second portion.

In an exemplary embodiment of the invention according to any of the described herein embodiments, each said SM portion and each said connector are formed by as a single SM tubular portion. Optionally or alternatively, one or more segments is deployed to have a different deployed diameter than another of said segments.

In an exemplary embodiment of the invention according to any of the described herein embodiments, each said SM portion has a shape memory diameter and wherein at least one SM portion has a different shape memory diameter or cross-sectional shape than that of another of said SM portions.

In an exemplary embodiment of the invention according to any of the described herein embodiments, each said SM portion is heat treated and wherein at least one SM portion has a different heat treatment from another of said SM portions.

In an exemplary embodiment of the invention according to any of the described herein embodiments, each said segment has a segment axial length and at least one segment has a different axial length from that of another segment.

In an exemplary embodiment of the invention according to any of the described herein embodiments, at least two SM portion segments and/or second portion segments differ in one or more of thickness and lattice design.

There is provided in accordance with an exemplary embodiment of the invention, a tubular expandable structure comprising:
a tubular SM portion treated such that said SM portion has a shape memory diameter;
a tubular second portion restraining said SM portion;
wherein the expandable structure is stable in a crimped state where said shape memory diameter is less than a structure deployed state diameter;
wherein the expandable structure is stable in at least one deployed state;
wherein said SM portion is martensite at a deployed diameter; and
wherein said second portion is selected so that a contracting force thereof at said deployed state is less than a SM portion martensite resistive force.

There is provided in accordance with an exemplary embodiment of the invention, an expandable axially oriented structure comprising:
a plurality of circumferential segments;
a plurality of connectors, each connector axially coupling two segments;
wherein said connectors each comprise: two flexible struts, each flexible strut comprising a vertex around which said strut bends axially to compress said connector;
wherein said connectors are more axially compressible than said segments.

Optionally, said plurality of connectors comprise at least one rhombic shape.

There is provided in accordance with an exemplary embodiment of the invention, a tubular expandable structure comprising:
a plurality of rigid struts orientated axially along the structure and each having an initial length;
a plurality of flexible members;
wherein each rigid strut is coupled to another two rigid struts;
wherein coupling one rigid strut to another is by at least two flexibly bent members, such that rigid struts coupled by flexibly bent members form at least one circumferential segment of the tubular structure;
wherein upon a radial expanding force said flexible members unbend to expand a diameter of each said circumferential segment;
wherein upon a radial contracting force said flexible members bent to contract a diameter of each circumferential segment; and
wherein said rigid struts substantially maintain said initial lengths thereof. Optionally, the structure comprises a plurality of said circumferential segments interconnected by connecting elements. Optionally or alternatively, elements are axially contractable and elongatable and are weaker than said rigid struts.

In an exemplary embodiment of the invention according to any of the described herein embodiments, said SM portion comprises a nickel-titanium shape memory alloy.

In an exemplary embodiment of the invention according to any of the described herein embodiments, said second portion comprises polymer.

In an exemplary embodiment of the invention according to any of the described herein embodiments, said second portion is formed of at least 50% high recoil polymer.

In an exemplary embodiment of the invention according to any of the described herein embodiments, said second portion maintains elasticity after a 300% strain.

In an exemplary embodiment of the invention according to any of the described herein embodiments, said structure is configured for at least 5 expand-collapse cycles without fatigue thereof.

There is provided in accordance with an exemplary embodiment of the invention, a method of crimping an expandable structure comprising:
cooling an expanded structure comprising:
a SM portion in a strain induced state;
a second portion exerting a contracting force on said SM portion;
wherein said cooling is such that a SM resisting force is less than the second portion retracting force; and
allowing said structure to collapse due to said second portion retracting force. Optionally, said cooling is below a SM portion transformation temperature.

There is provided in accordance with an exemplary embodiment of the invention, a method of crimping an expandable structure comprising:
providing an expanded structure comprising:
a SM portion in a strain induced state;
a second portion exerting a contracting force on said SM portion;
expanding said structure such that a SM portion resisting force reduces below said second portion retracting force, thereby causing contraction of said SM portion.

There is provided in accordance with an exemplary embodiment of the invention, a method of crimping an expandable structure comprising:
cooling an expanded structure comprising:
a SM portion in a strain induced state;
a second portion exerting a contracting force on said SM portion;
wherein said cooling is such that the SM material is urged to return to a second shape memory diameter.

There is provided in accordance with an exemplary embodiment of the invention, a method of manufacturing an expandable tubular structure comprising:
treating a tubular SM portion such that:
said SM portion includes a shape memory diameter;
a SM portion expanding force decreases as a function of strain applied to
said SM portion; and
coupling said SM portion to a second tubular portion with a smaller relaxed size than said SM portion shape memory diameter. Optionally, said treating comprises heat treating. Optionally or alternatively, said SM portion is a stent formed from a shape memory material suitable for medical stents. Optionally or alternatively, said coupling comprises:
crimping said SM portion; and
inserting said SM portion into said second portion. Optionally or alternatively, said treating comprises treating said tubular SM portion such that said SM portion has a second shape with a second shape memory diameter.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

For clarity, not all elements are labeled on all figures.

In the drawings:

FIG. 1A is a simplified schematic cross sectional view of a structure in a crimped configuration within a lumen, according to some embodiments of the invention;

FIG. 1B is a simplified schematic cross sectional view of a structure in a deployed configuration within a lumen, according to some embodiments of the invention;

Figure 2:
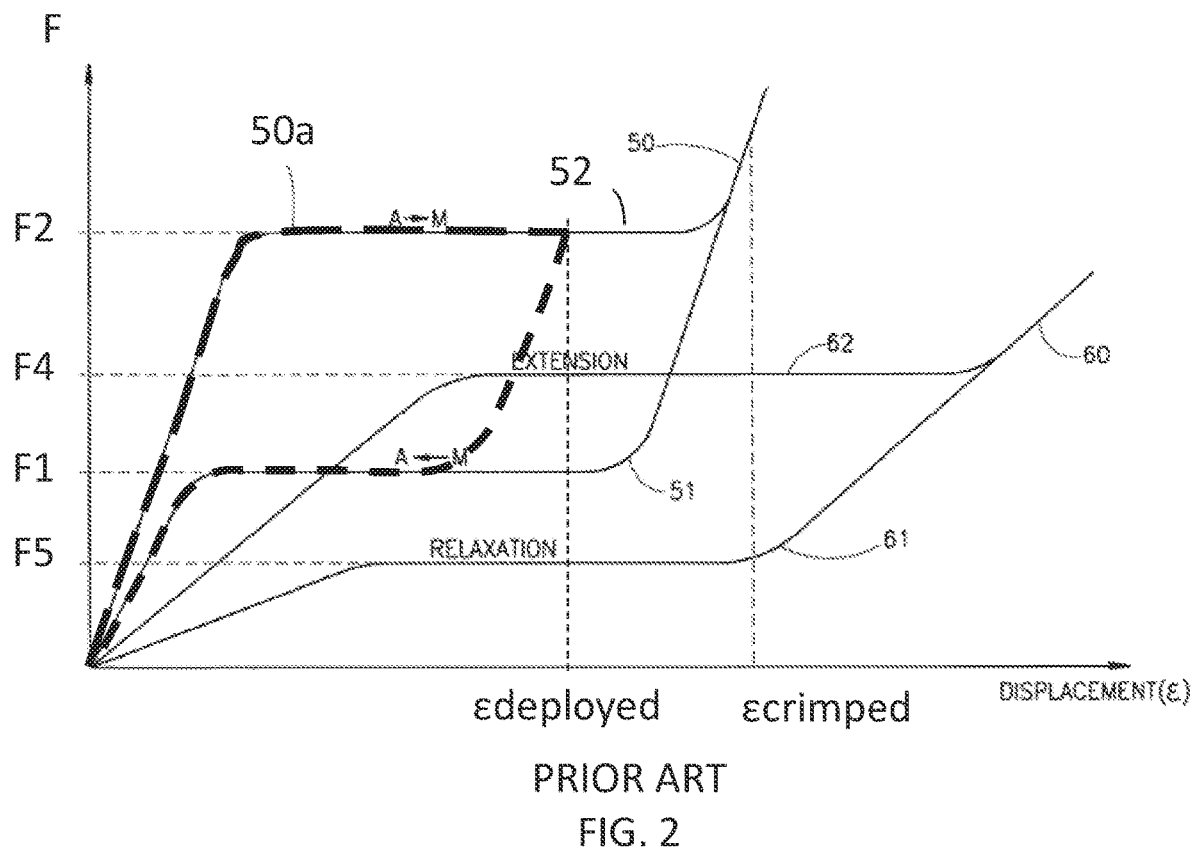
Figure 3:
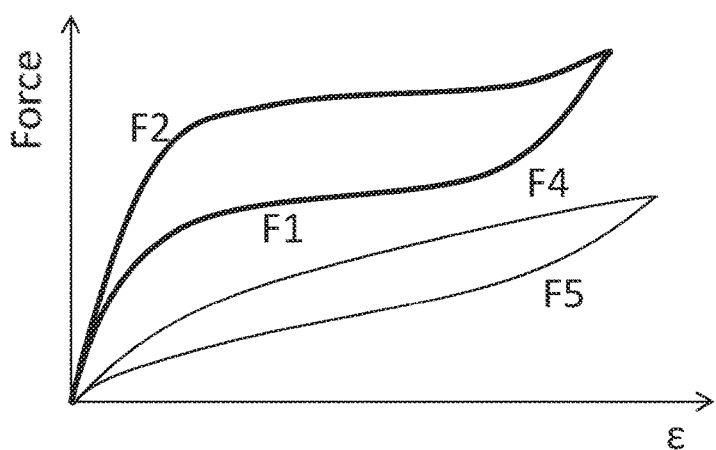
Figure 4:
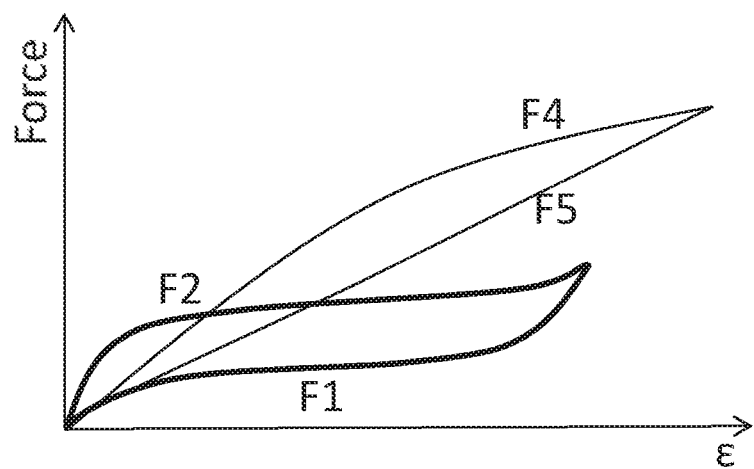
Figure 5:
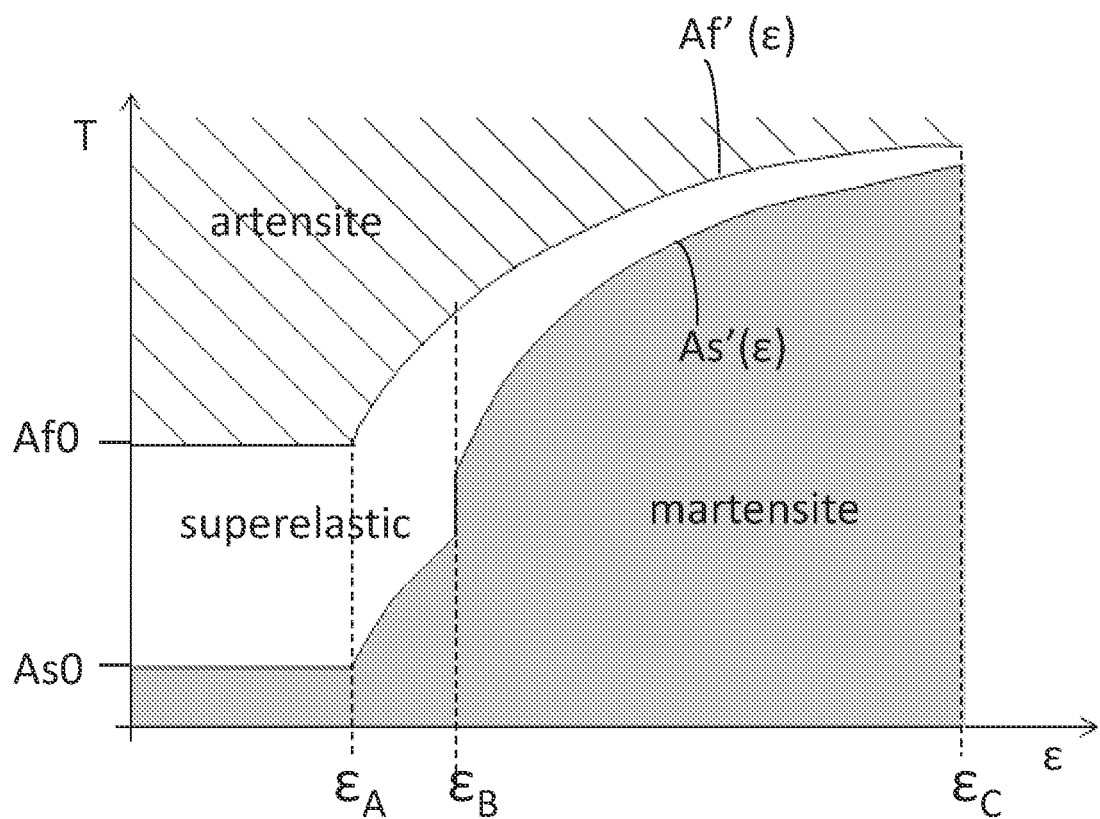
Figure 6:
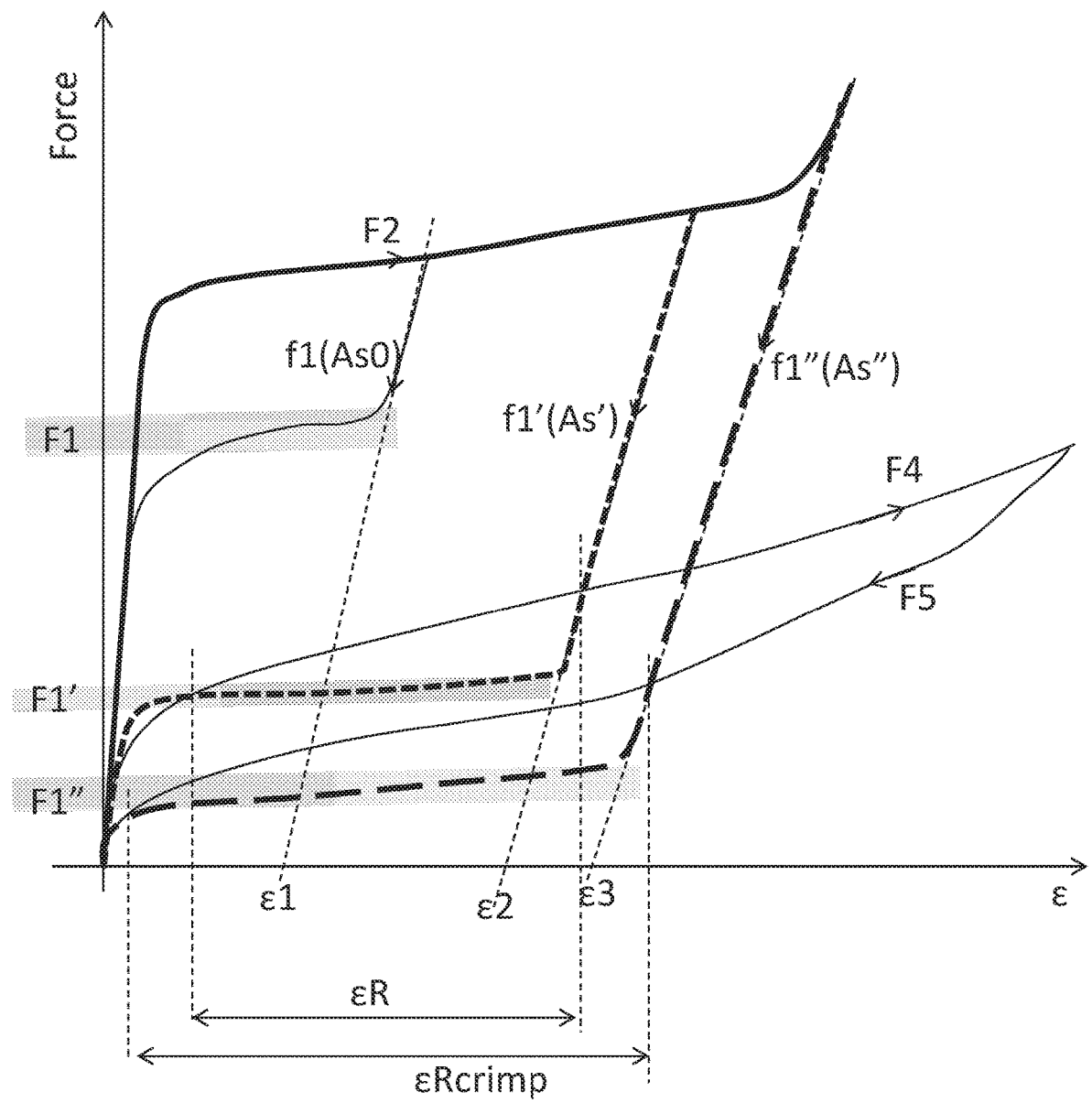
Figure 7:
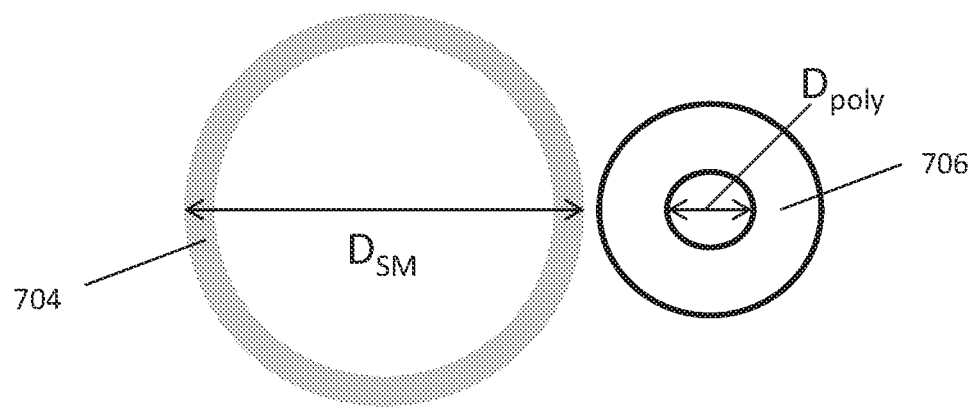
Figure 8A:
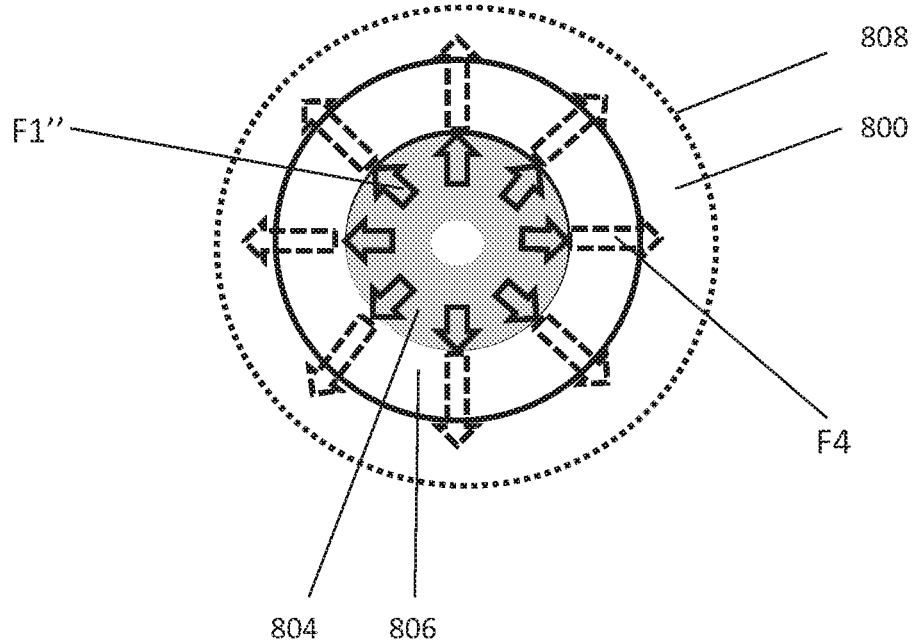
Figure 8B:
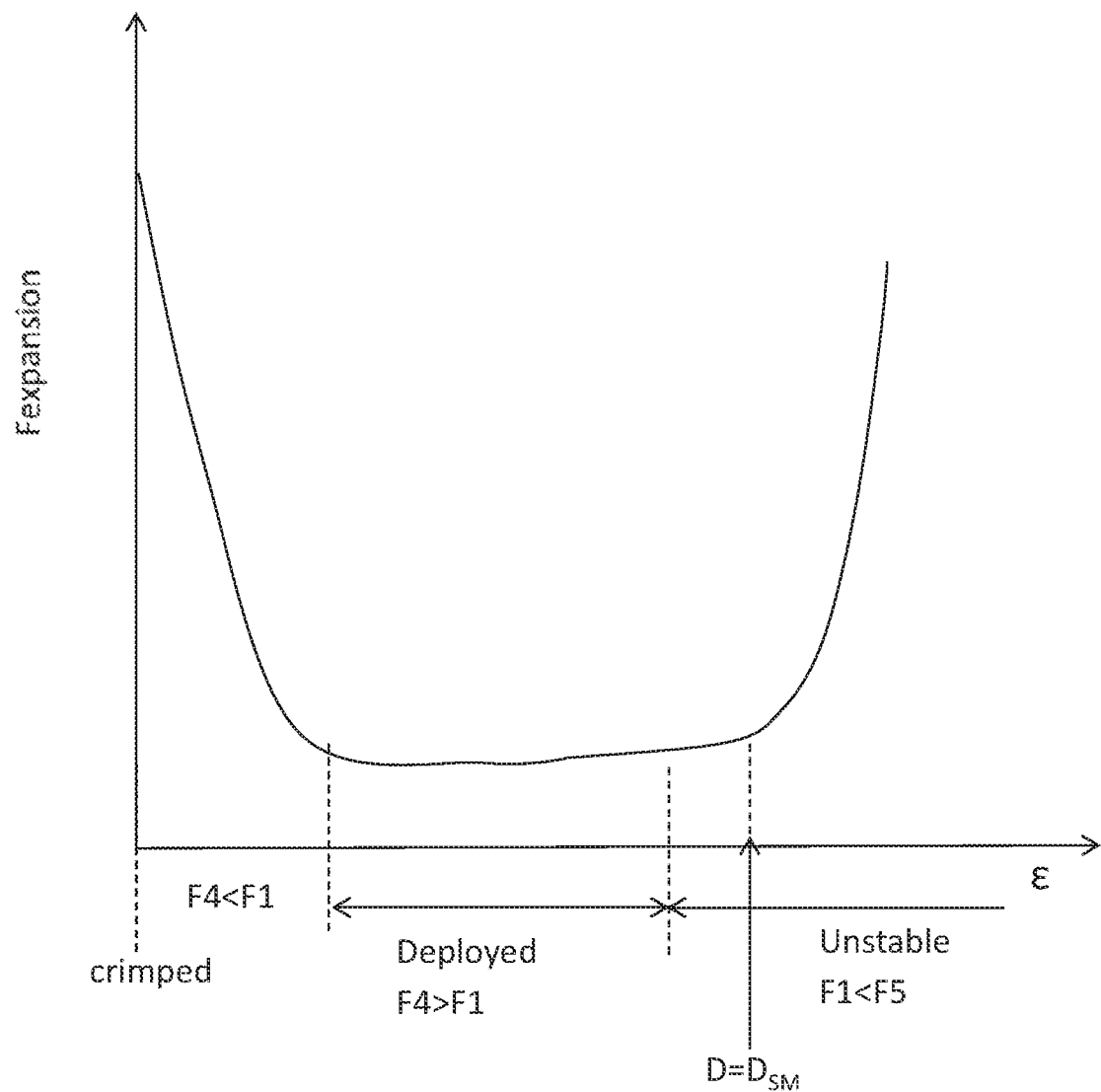
Figure 8C:
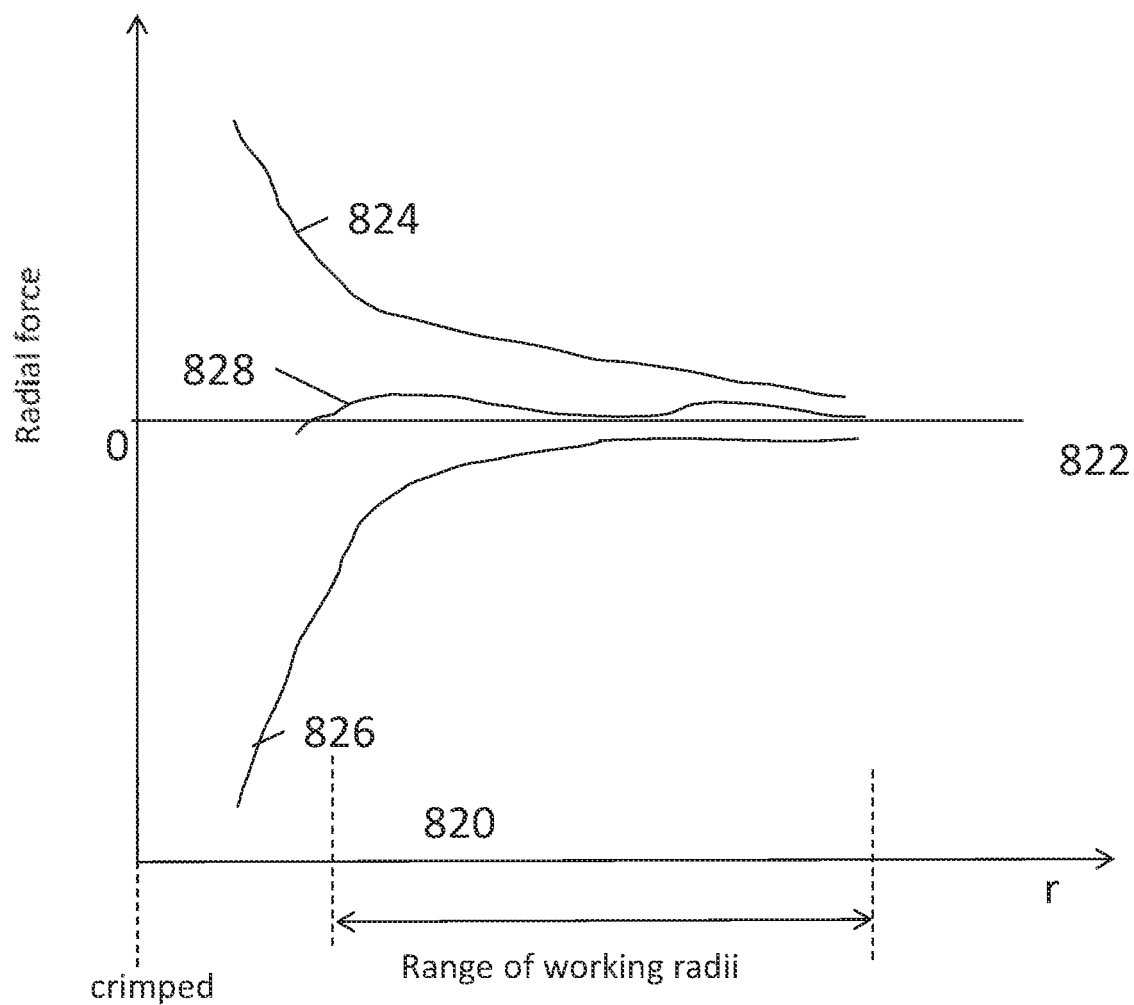
Figure 9A:
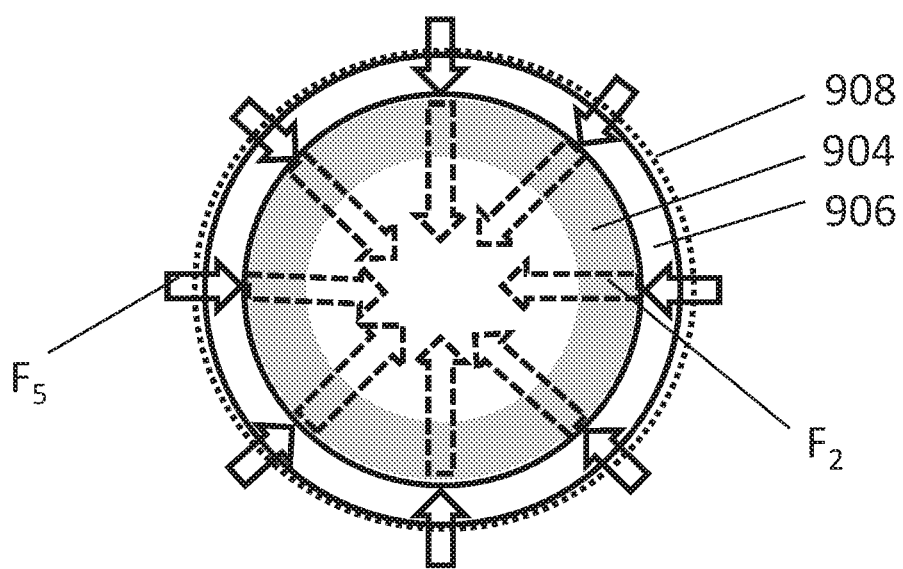
Figure 9B:
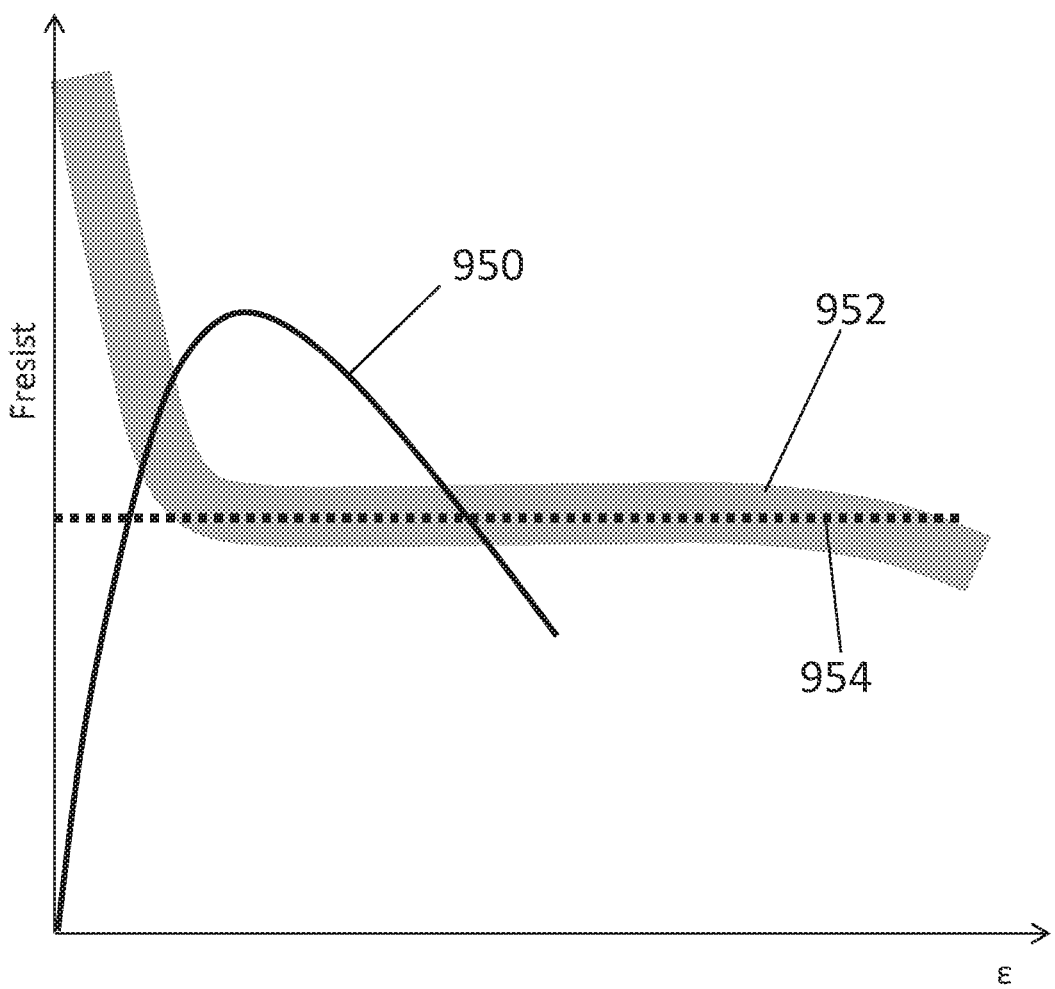
Figure 10:
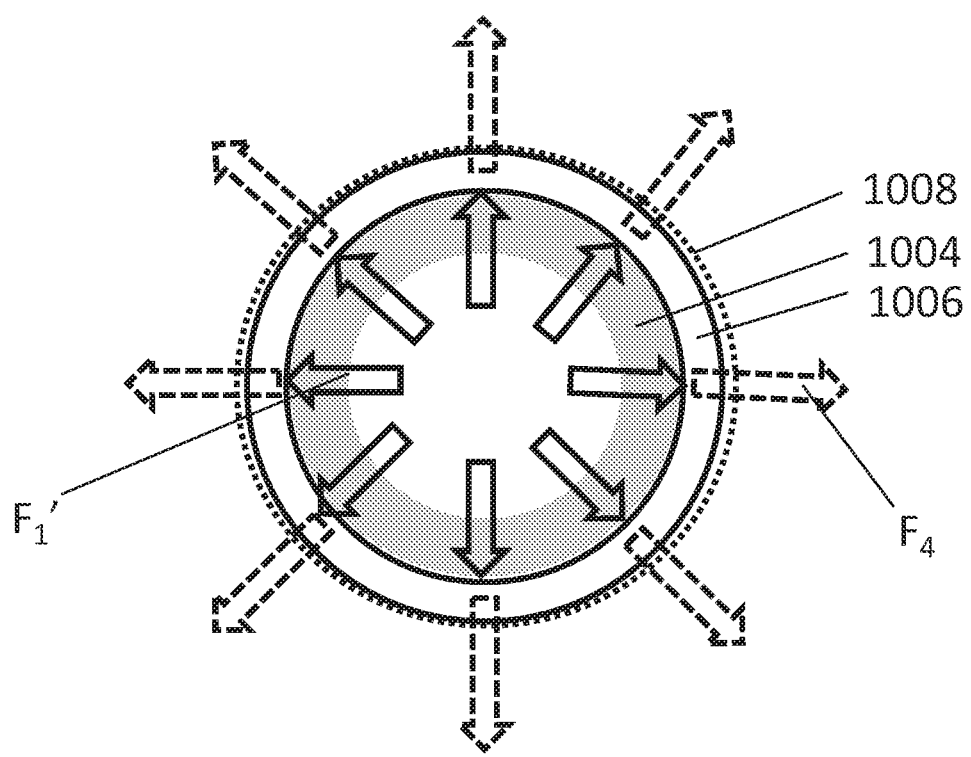
Figure 11:
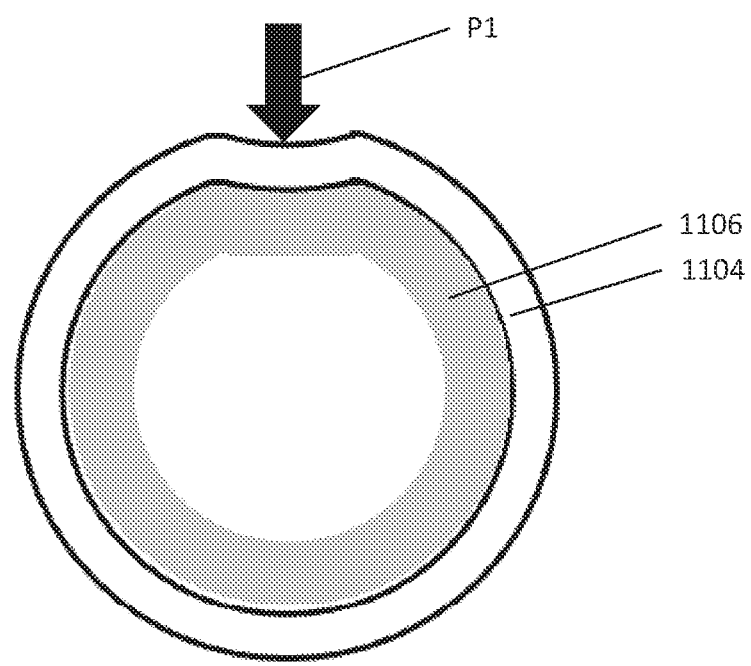
Figure 12:
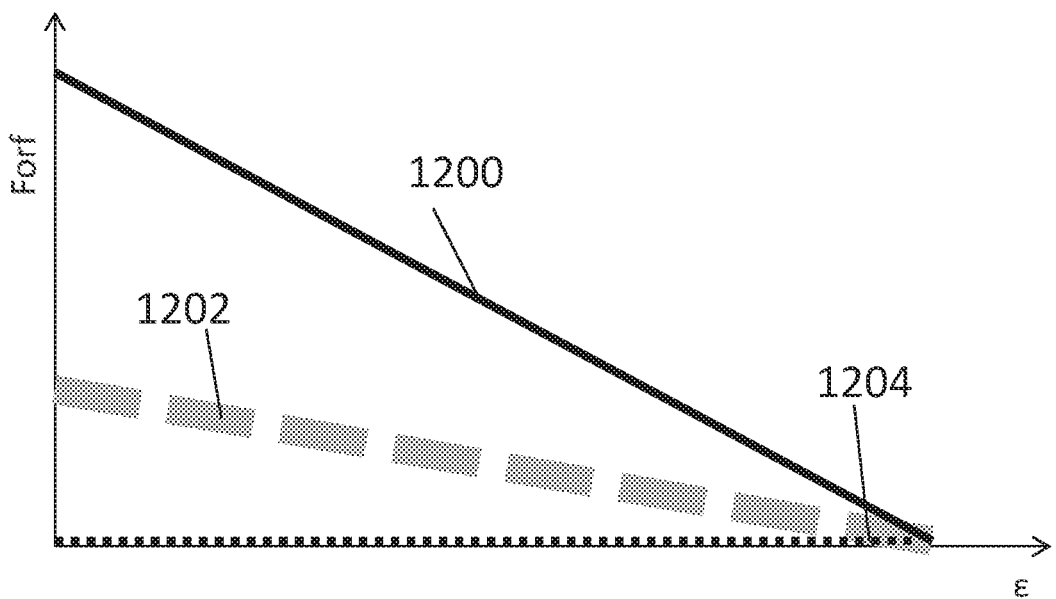
Figure 13:
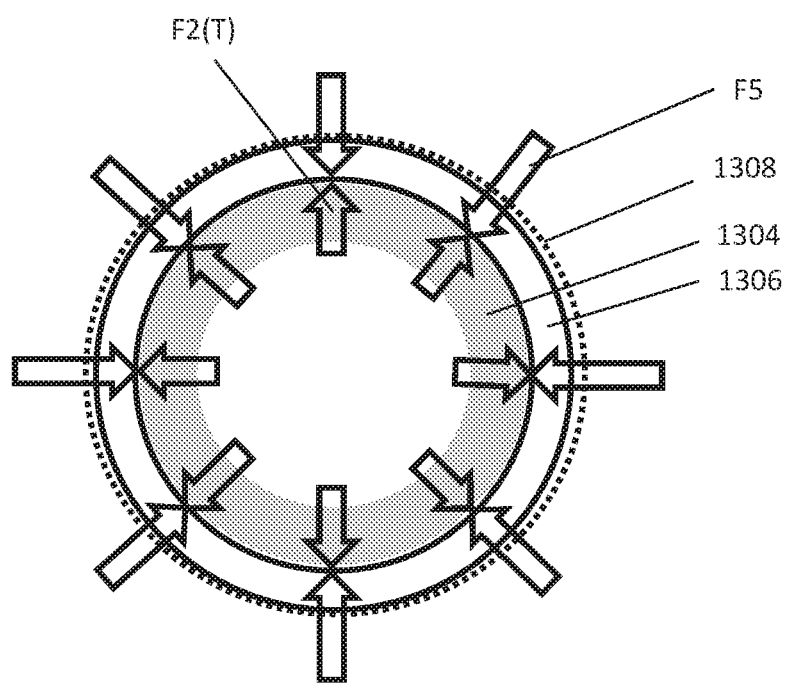
Figure 14A:
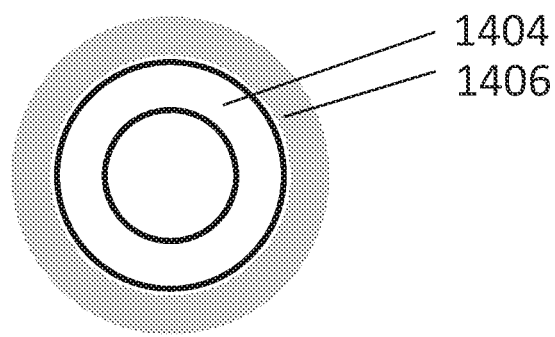
Figure 14B:
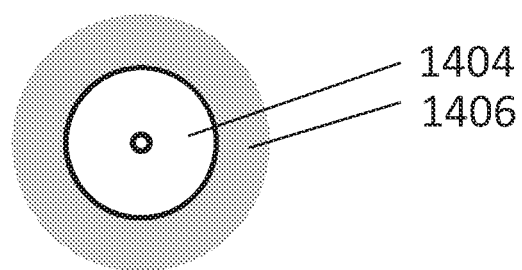
Figure 15:
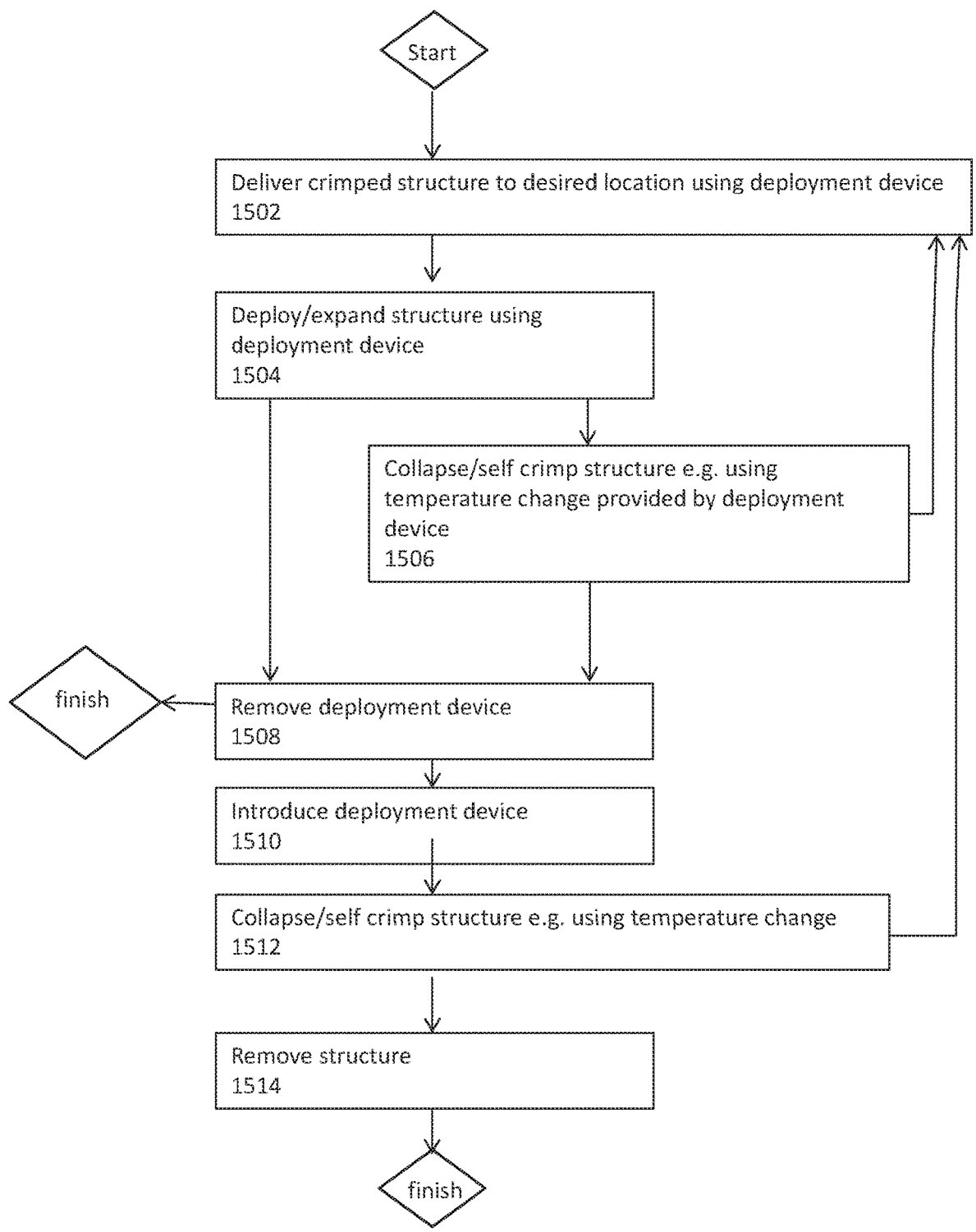
Figure 16:
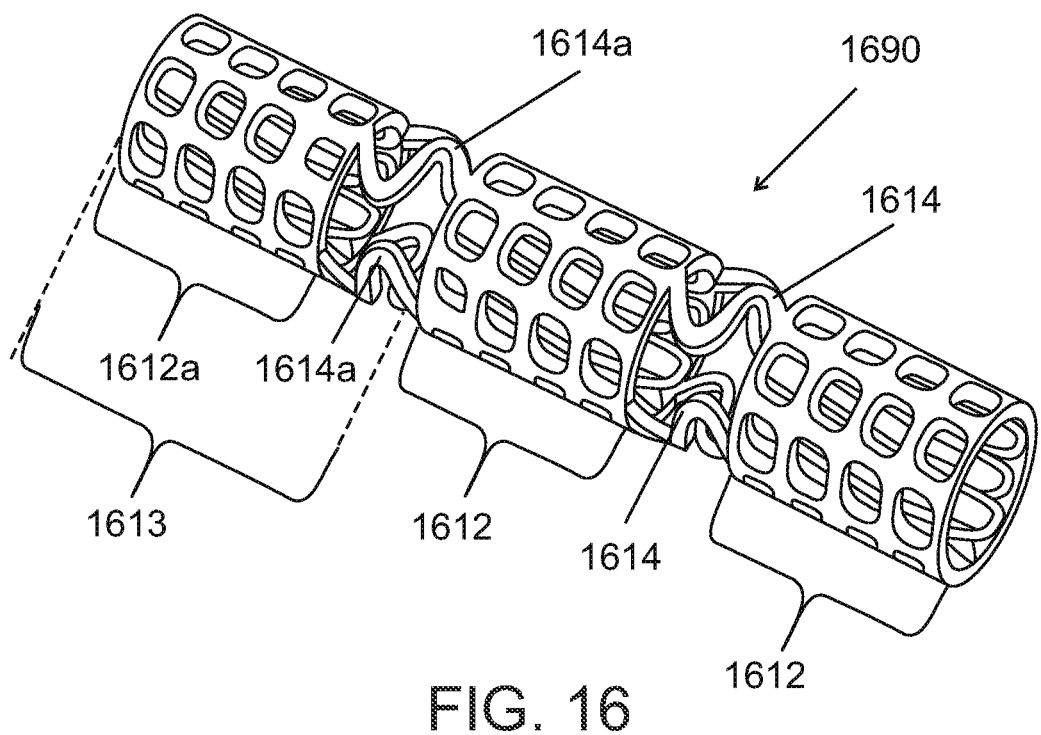
Figure 17:
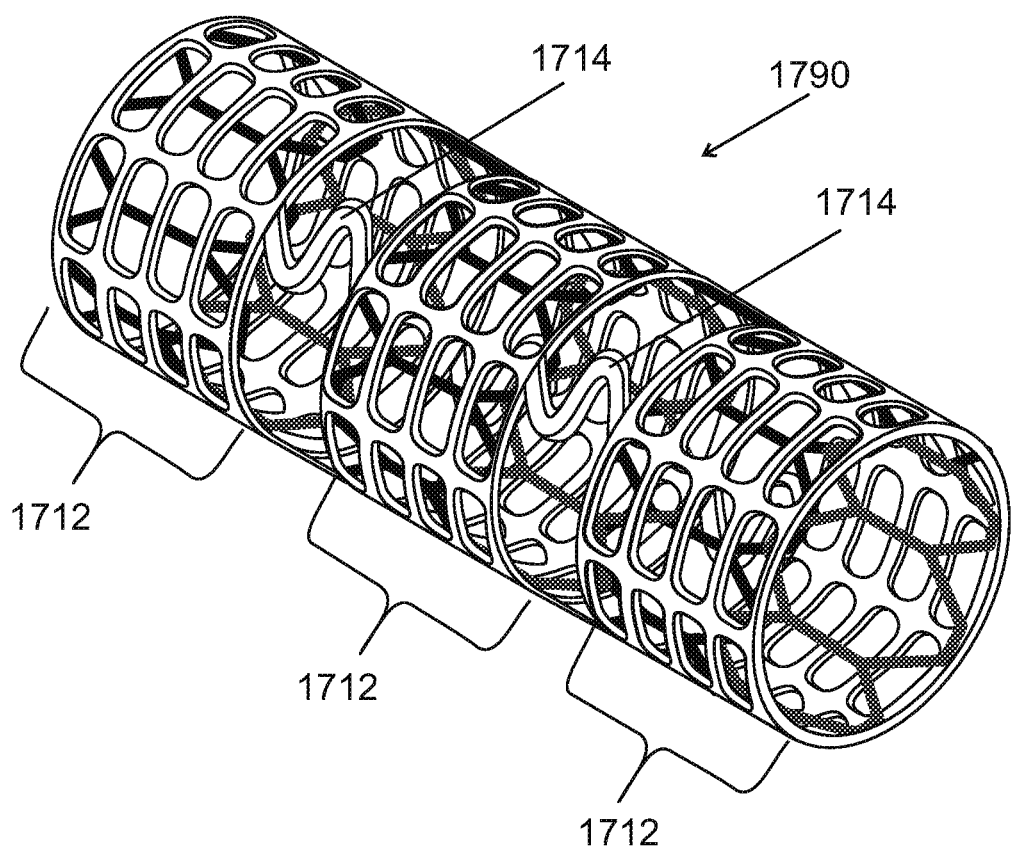
Figure 18:
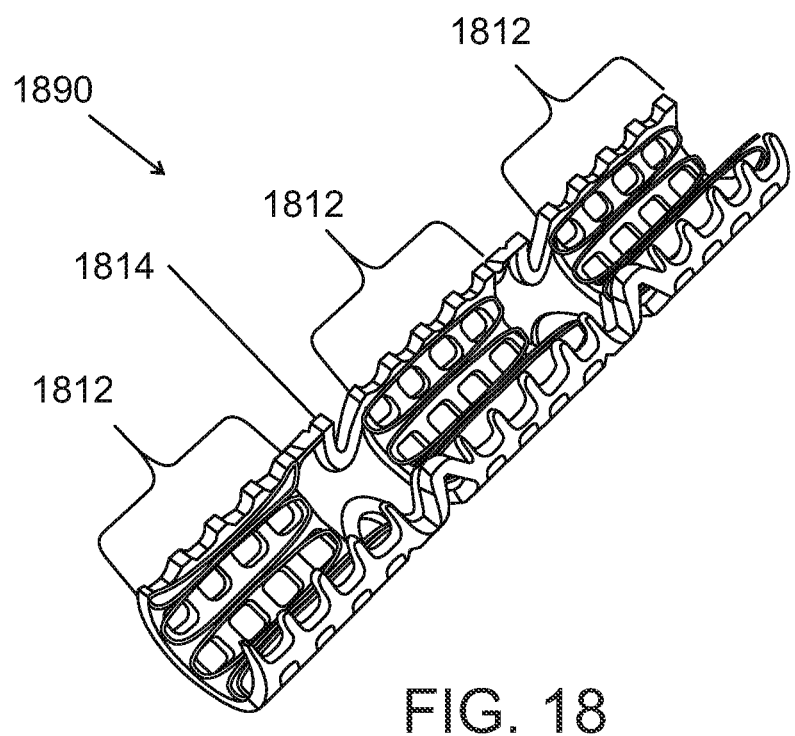
Figure 19:
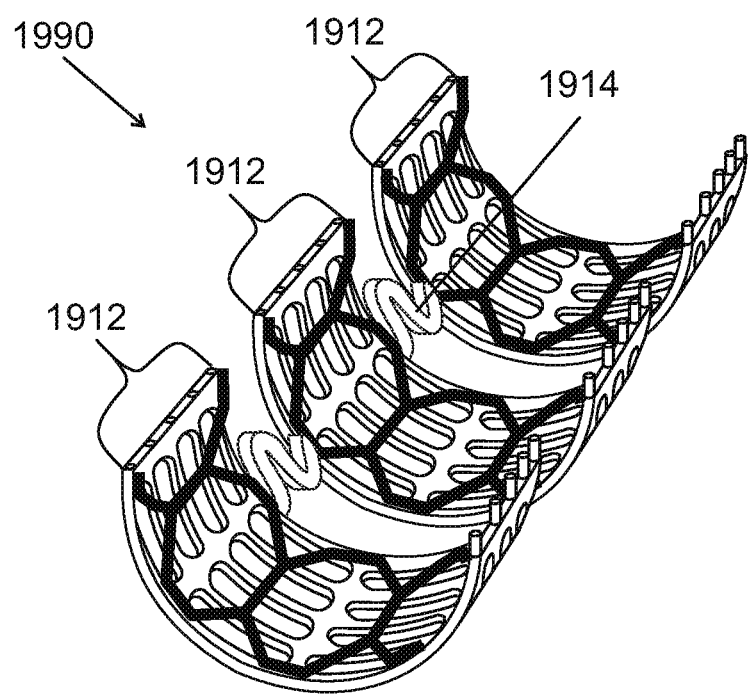
Figure 20:
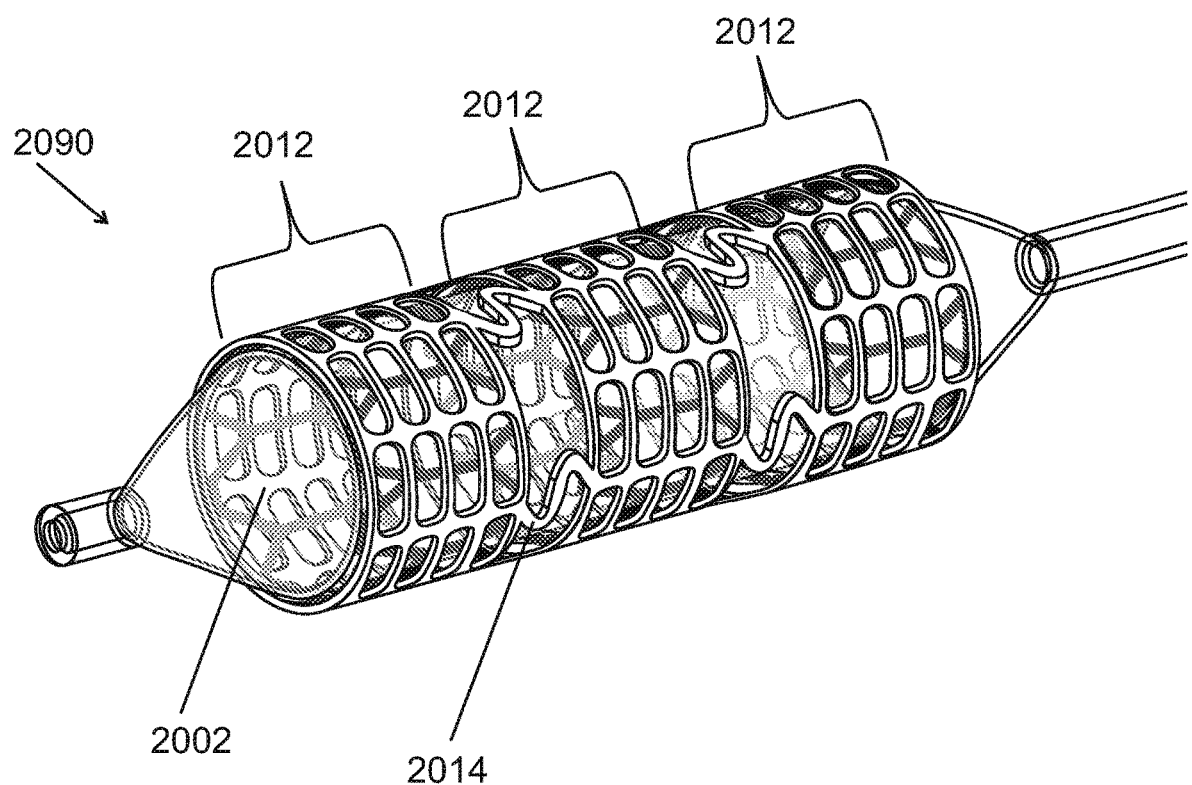
Figure 21:
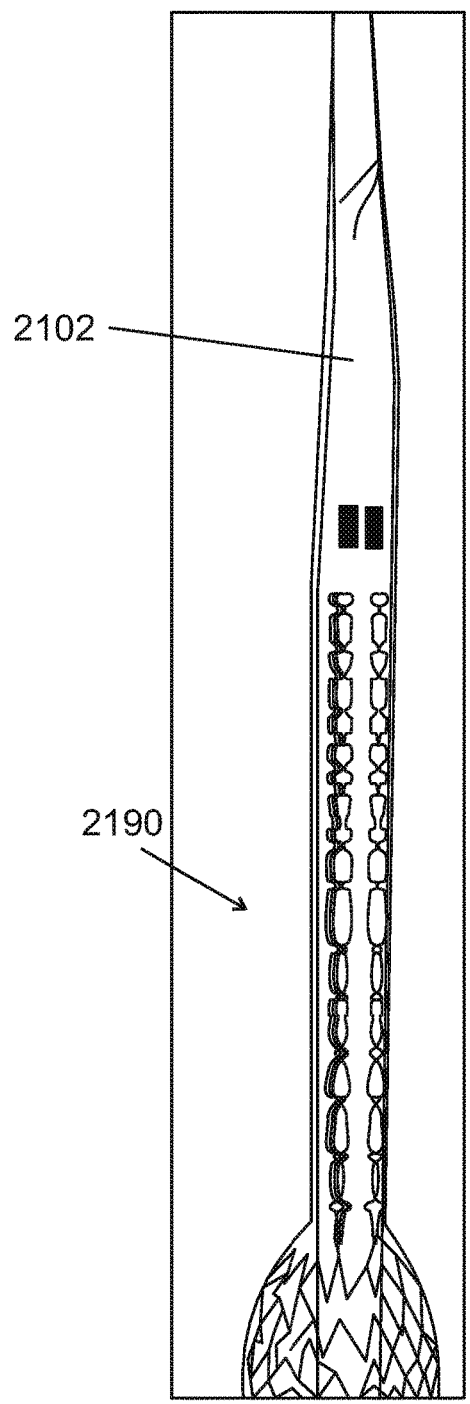
Figure 22:
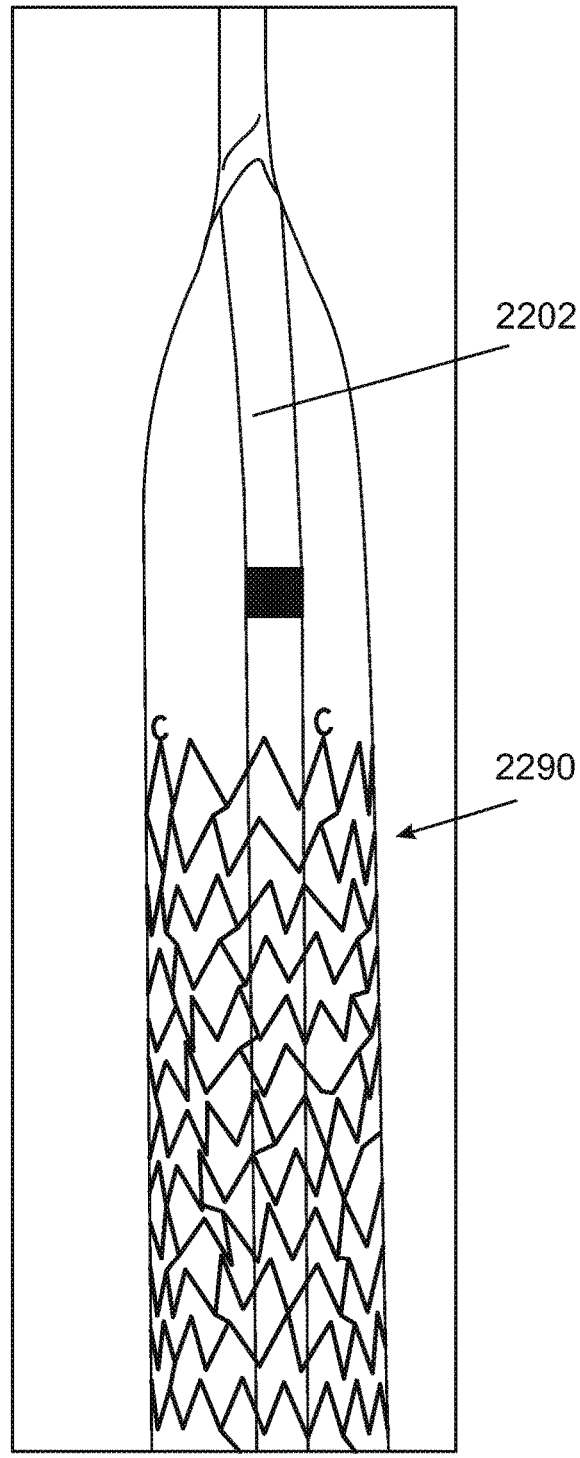
Figure 23:
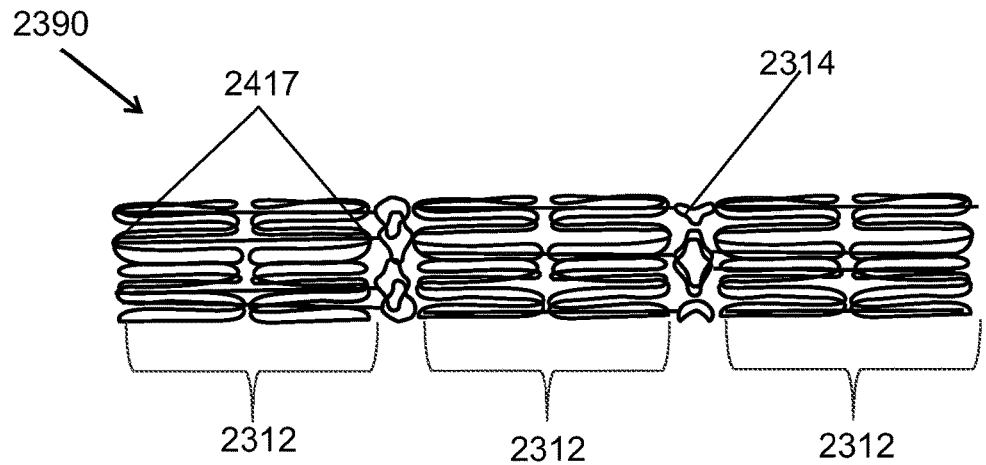
Figure 24:
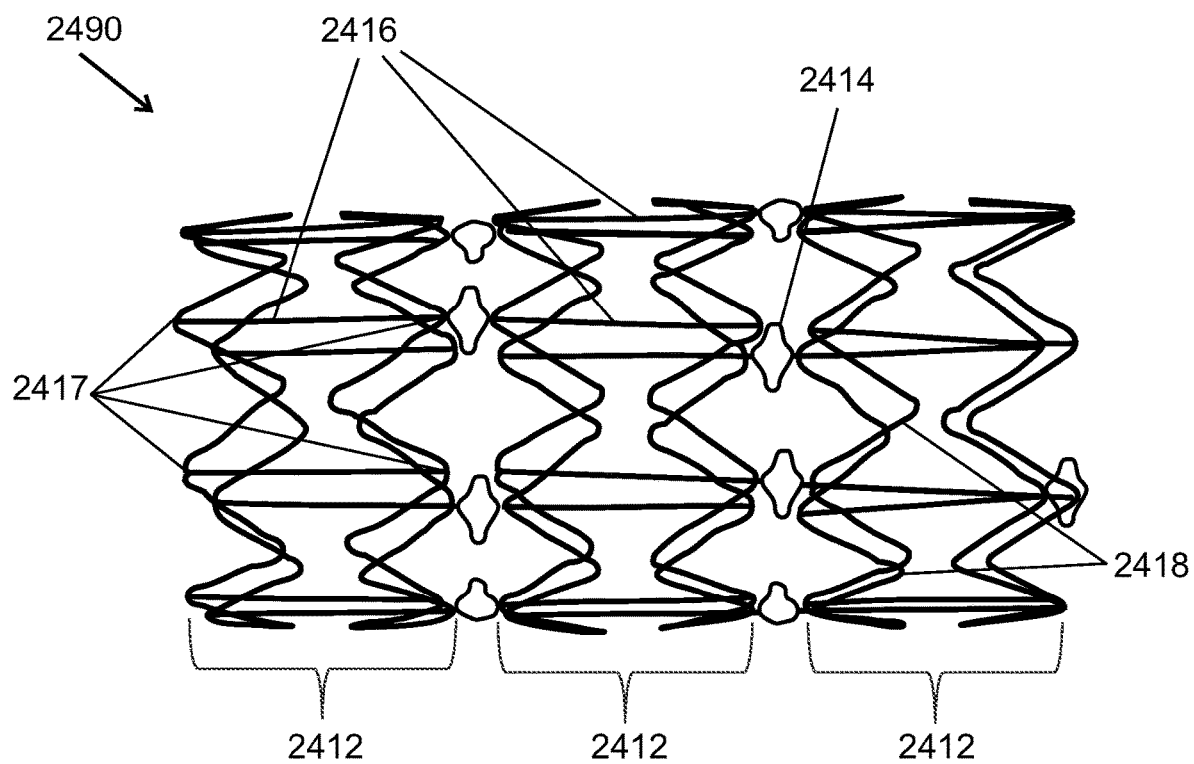
Figure 25:
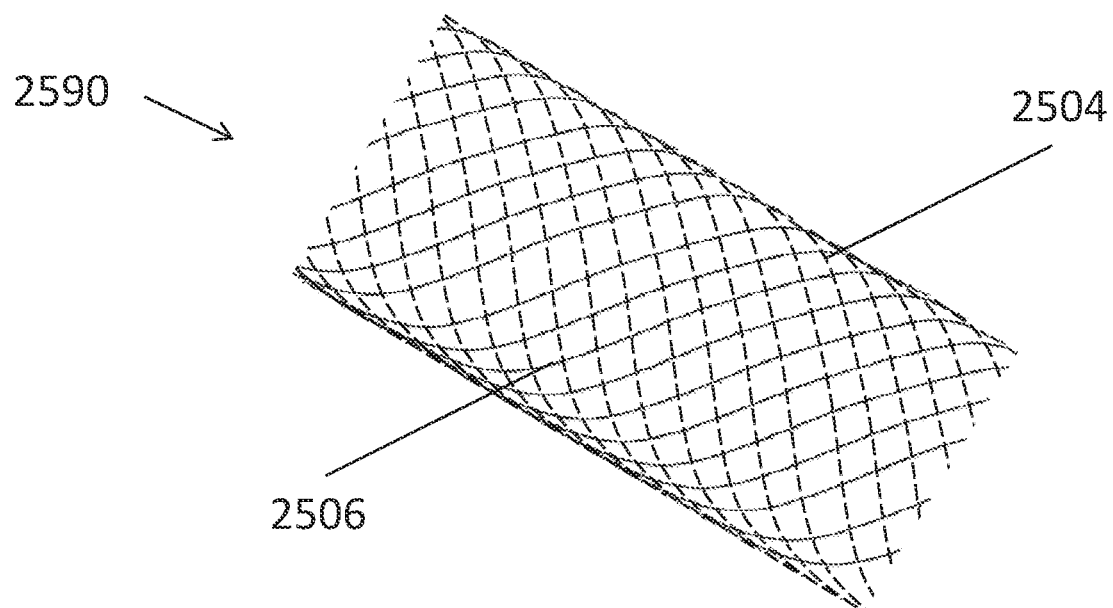
Figure 26:
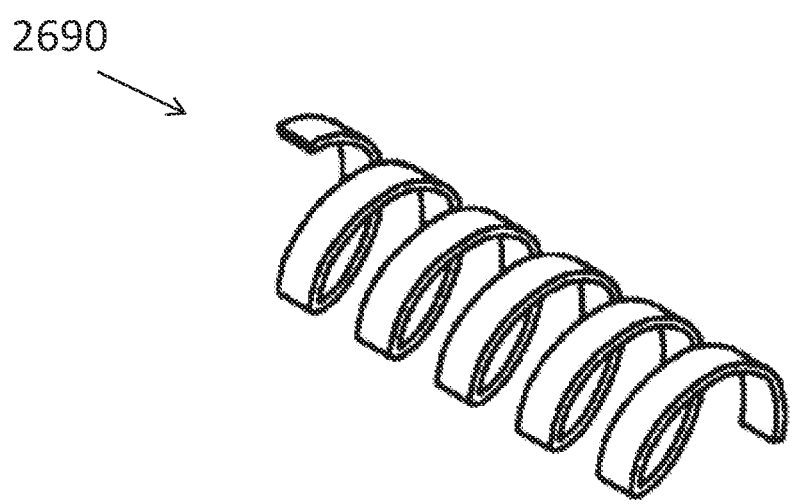
Figure 30:
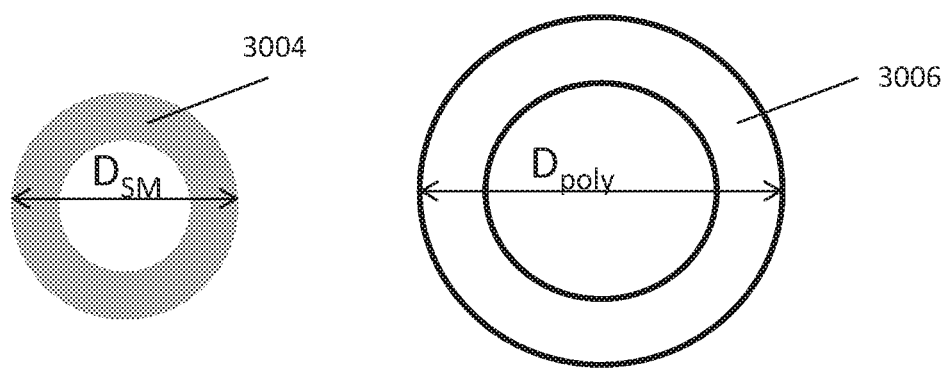
Figure 31:
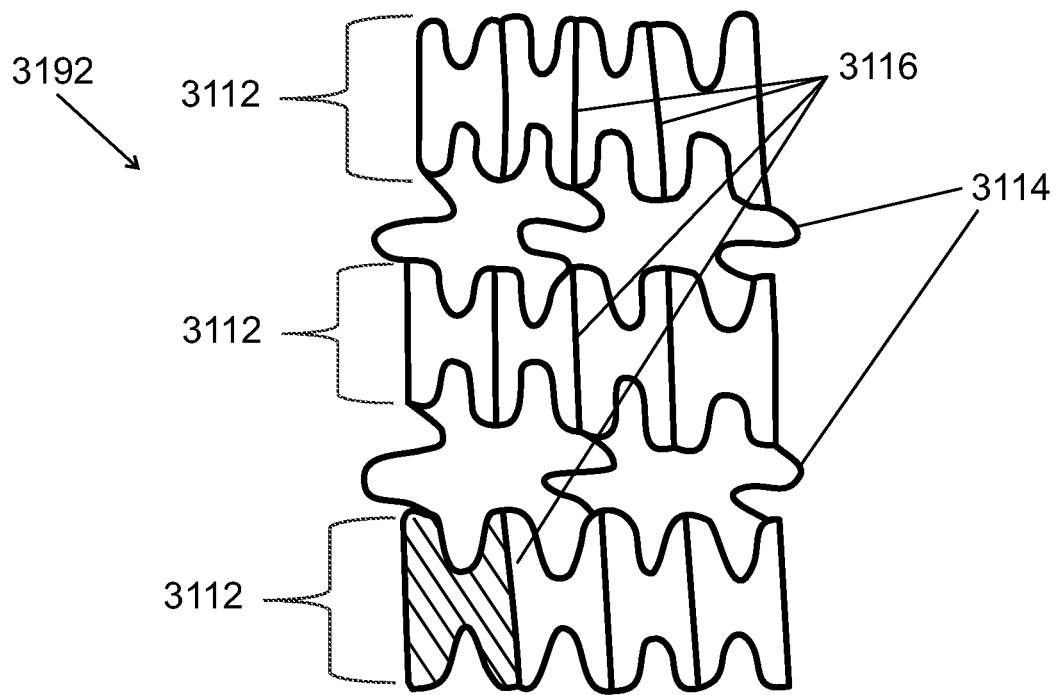
Figure 32:
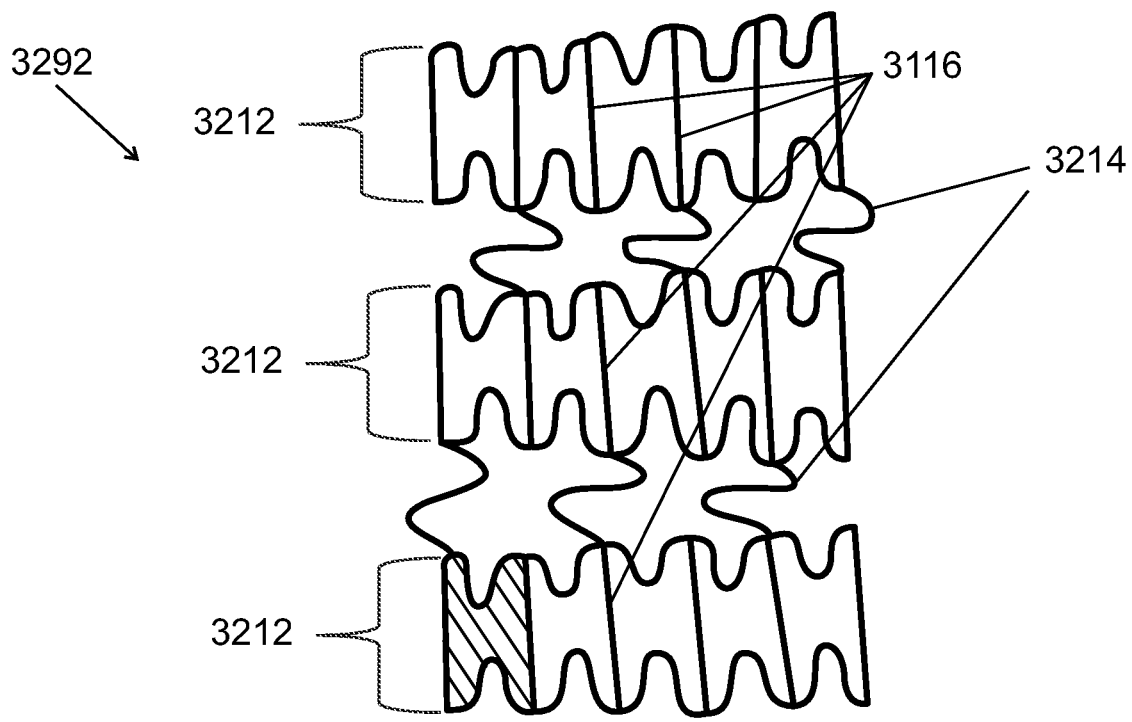
Figure 33:
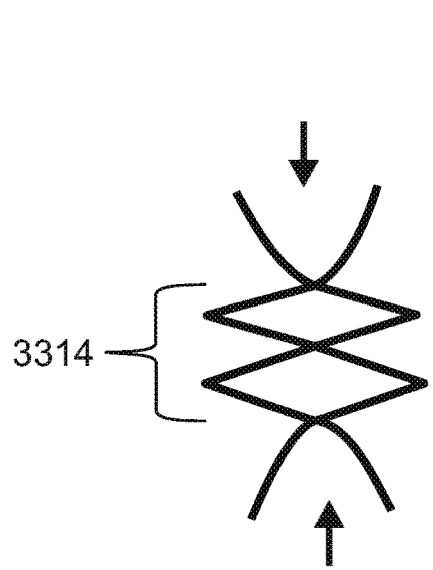
Figure 34:
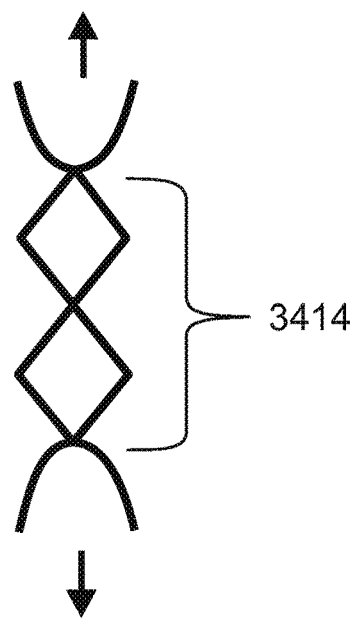
Figure 35:
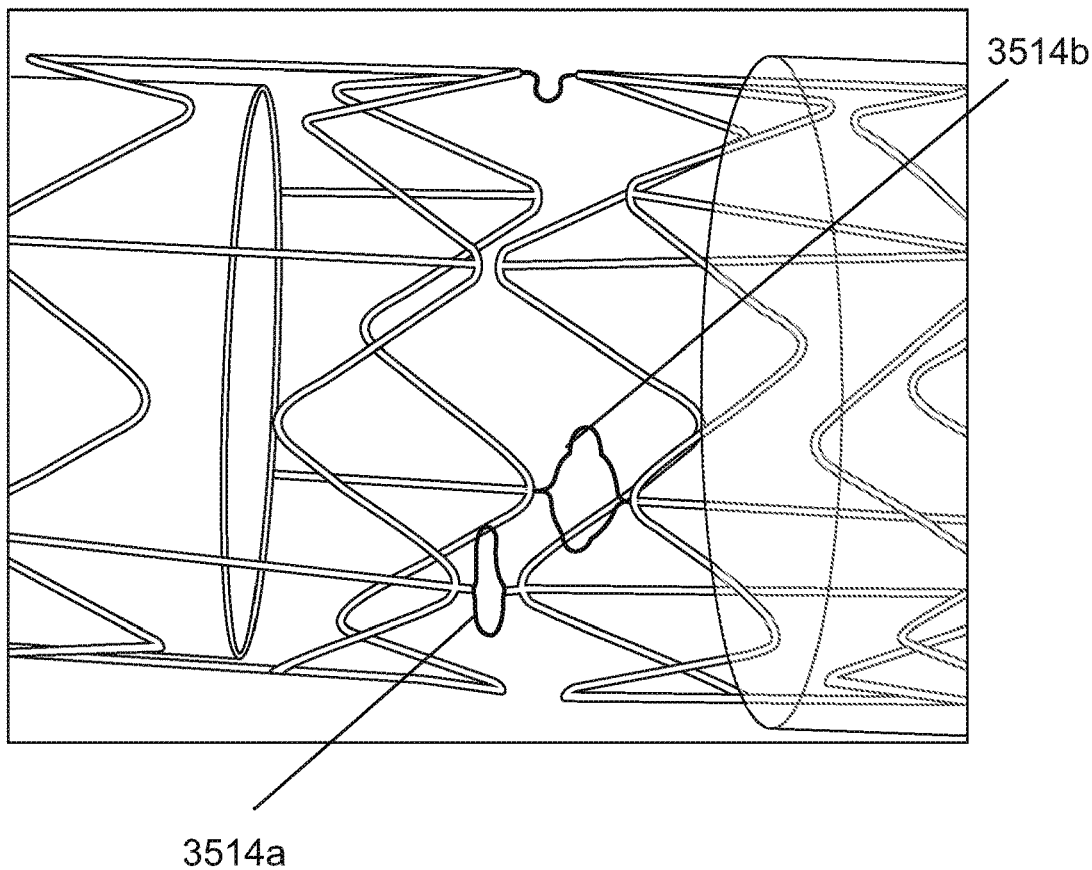
Figure 36:
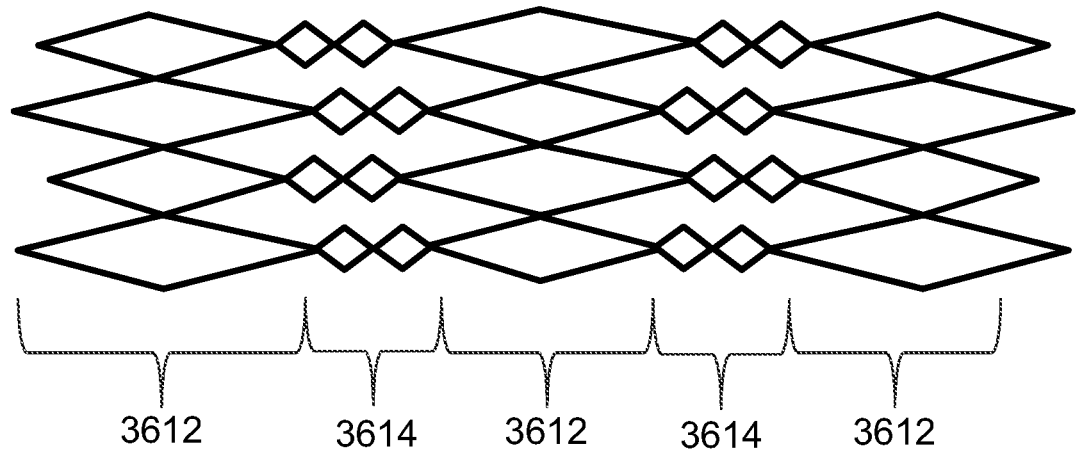
Figure 37:
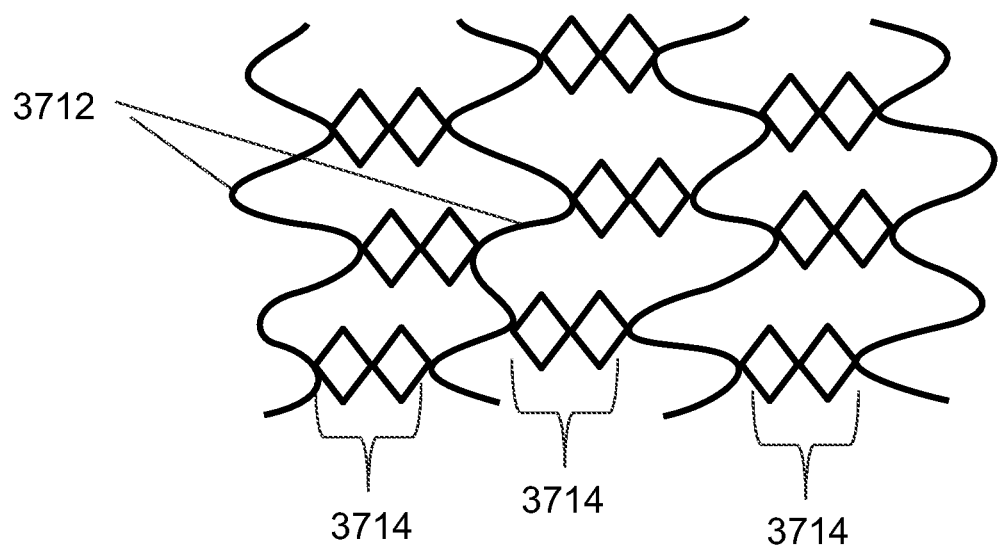
Figure 38A:
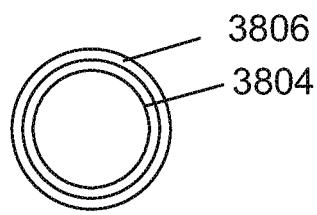
Figure 38B:
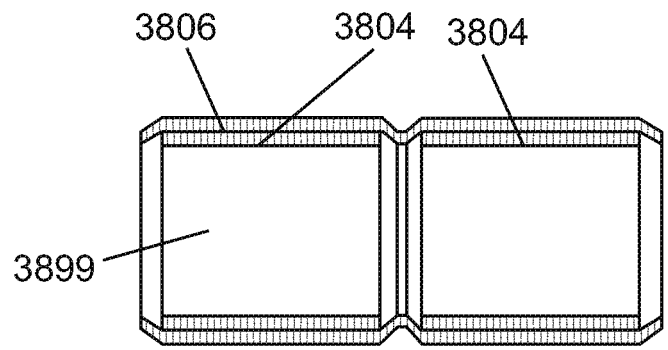
Figure 38C:
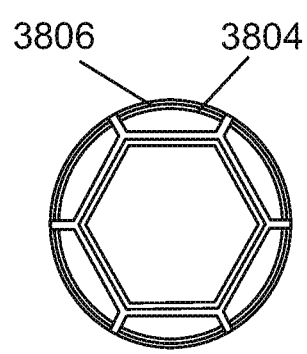
Figure 38D:
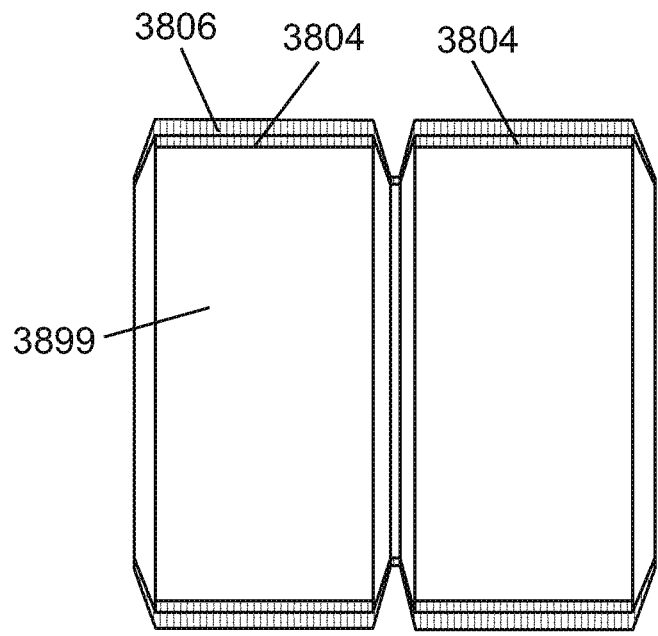
Figure 38E:
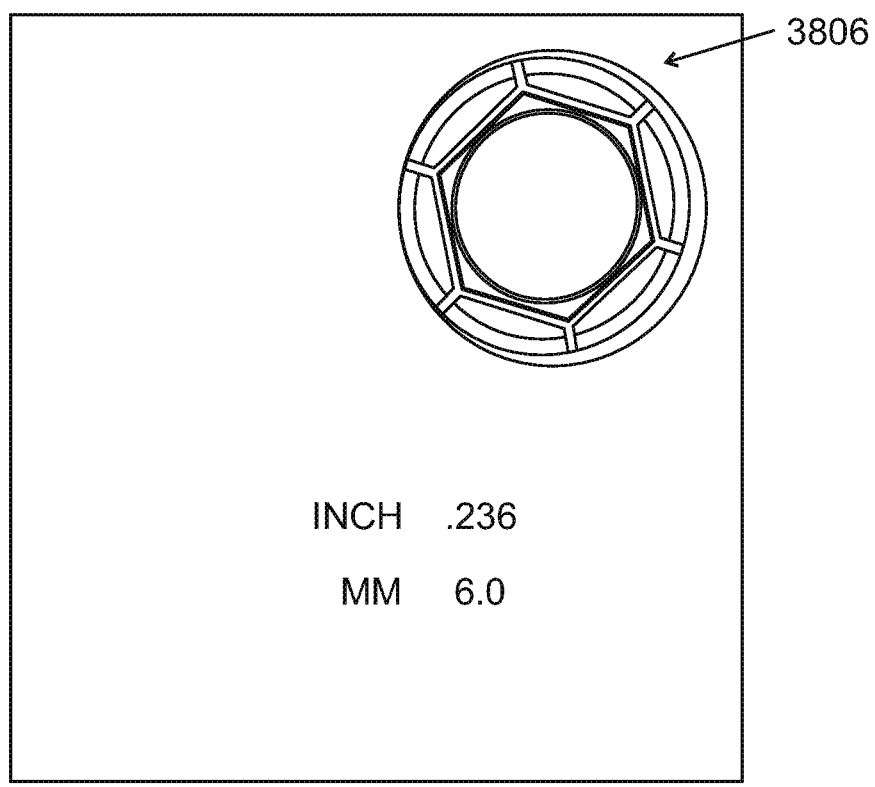
Figure 39:
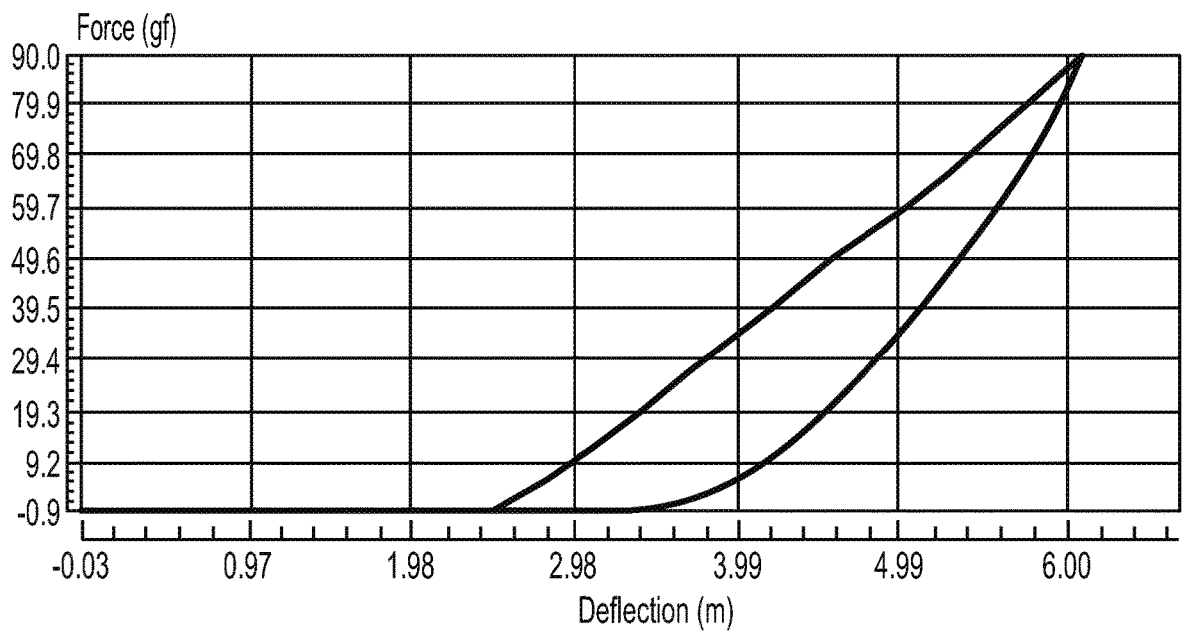
Figure 40:
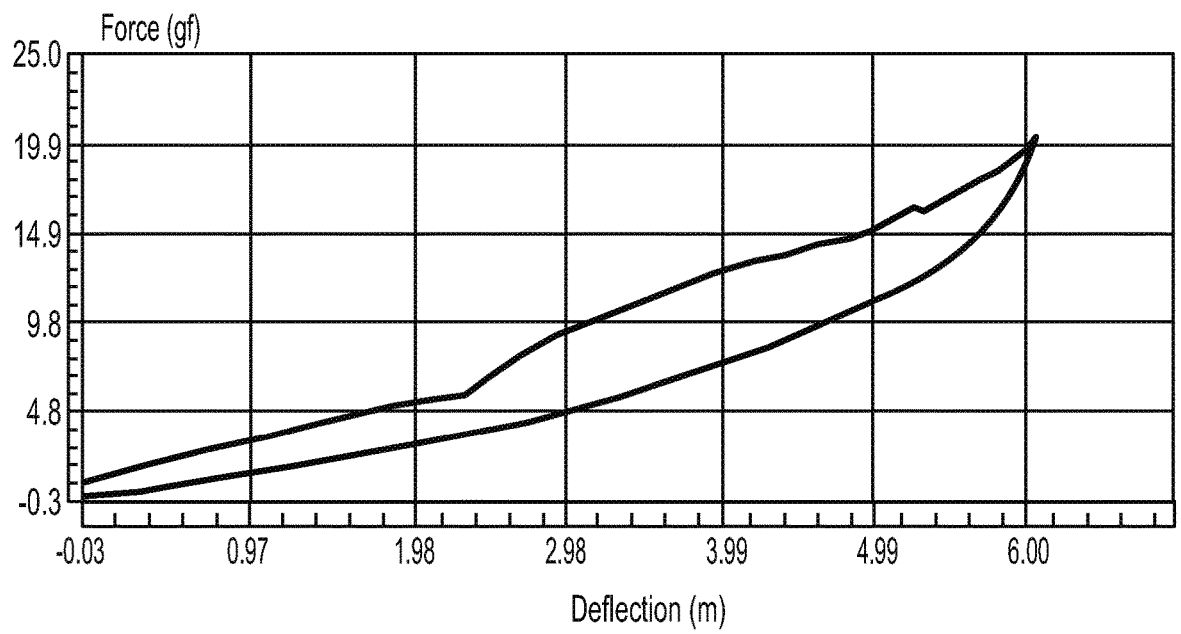
Figure 41:
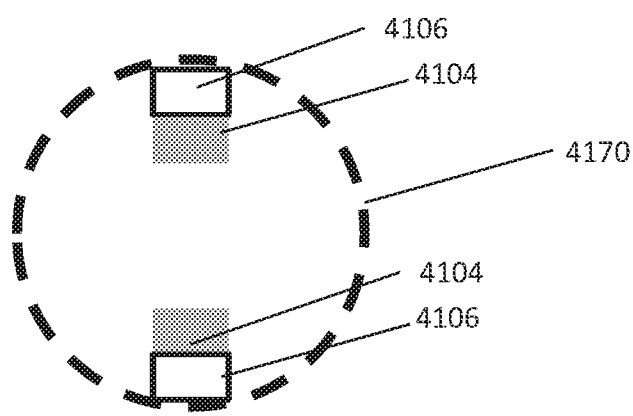
Figure 42:
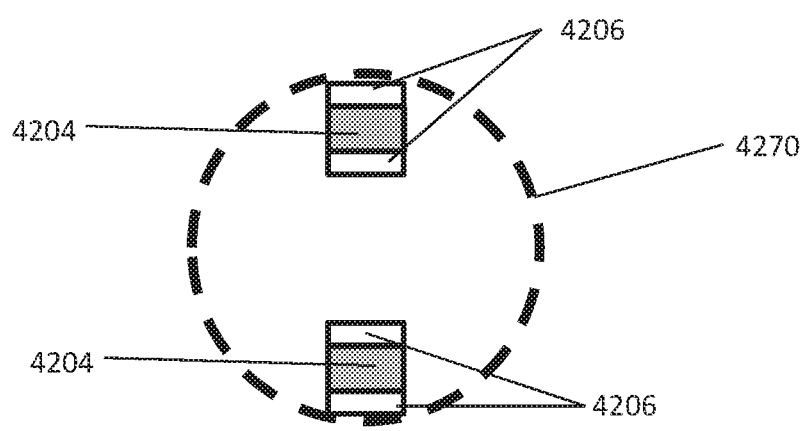

FIG. 2 presents a plot of applied force, F, with strain, $\varepsilon$, for a SM portion and for a plastic material portion of a composite stent apparently described in the art;

FIG. 3 presents a plot of applied force, F, with strain, $\varepsilon$, for materials for a composite stent apparently described in the art;

FIG. 4 presents a plot of applied force, F, with strain, $\varepsilon$, for materials for a composite stent apparently described in the art;

FIG. 5 presents plots of shape memory material austenite transformation start temperature, $A_s$, and austenite finish temperature $A_f$, with strain, for stent materials used according to some embodiments of the invention;

FIG. 6 presents a plot of a force-strain hysteresis curves for a SM portion and a force-strain hysteresis curve for a polymer portion, according to some embodiments of the invention;

FIG. 7 is a simplified schematic of an uncoupled SM portion and a polymer portion, according to some embodiments of the invention;

FIG. 8A is a simplified schematic cross sectional view of a structure in a crimped configuration, according to some embodiments of the invention;

FIG. 8B presents a plot of applied expansion force, Fexpansion, with strain, $\varepsilon$, for a composite structure, according to some embodiments of the invention;

FIG. 8C is a chart showing the balancing between a force of expansion applied by a SM portion and a force of contraction applied by a second portion, in accordance with an exemplary embodiment of the invention;

FIG. 9A is a is a simplified schematic cross sectional view of a structure in a deployed configuration, according to some embodiments of the invention and forces showing a contracting force balance;

FIG. 9B presents plots of crush resistance (Fresist) with strain $\varepsilon$, according to some embodiments of the invention;

FIG. 10 is a simplified schematic cross sectional view of a structure in a deployed configuration, according to some embodiments of the invention and forces showing an expanding force balance;

FIG. 11 is a simplified schematic cross section of a structure in a deployed configuration, undergoing a local deformation, according to some embodiments of the invention;

FIG. 12 presents plots of outwards force from the structure (pushing force, Fpush) with strain $\varepsilon$, according to some embodiments of the invention;

FIG. 13 is a simplified schematic cross section of a structure in a deployed configuration, and forces on the structure upon a temperature change;

FIG. 14A is a simplified schematic cross section of a structure in a crimped configuration, according to some embodiments of the invention;

FIG. 14B is a simplified schematic cross section of the structure of FIG. 14A where the SM portion has two way shape memory structure in a crimped configuration, according to some embodiments of the invention;

FIG. 15 is a flow diagram of methods of use of a structure, according to some embodiments of the invention;

FIG. 16 is a simplified schematic of an exemplary structure in a crimped configuration, according to some embodiments of the invention;

FIG. 17 is a simplified schematic of an exemplary structure in a deployed configuration, according to some embodiments of the invention;

FIG. 18 is a simplified schematic cross section along a length of an exemplary structure in a crimped configuration, according to some embodiments of the invention;

FIG. 19 is a simplified schematic cross section along a length of an exemplary structure in a deployed configuration, according to some embodiments of the invention;

FIG. 20 is a simplified schematic side view of an exemplary structure in a deployed configuration, on a deployment device, according to some embodiments of the invention;

FIG. 21 is a photographic side view of an exemplary structure in a crimped configuration, on a deployment device, according to some embodiments of the invention;

FIG. 22 is a photographic side view of the exemplary structure of FIG. 21 in a deployed configuration, on a deployment device, according to some embodiments of the invention;

FIG. 23 is a photographic side view of an exemplary structure in a crimped configuration, according to some embodiments of the invention;

FIG. 24 is a photographic side view the exemplary structure of FIG. 23 in a deployed configuration, according to some embodiments of the invention;

FIG. 25 is a simplified schematic side view of an exemplary braided structure, according to some embodiments of the invention;

FIG. 26 is a simplified schematic side view of an exemplary coil structure, according to some embodiments of the invention;

FIG. 27 is a simplified schematic cross section of a structure with more than two portions, according to some embodiments of the invention;

FIG. 28 is a simplified schematic cross section of a structure, according to some embodiments of the invention;

FIG. 29 is a simplified schematic cross section of a structure, according to some embodiments of the invention;

FIG. 30 is a simplified schematic of an uncoupled SM portion and a polymer portion, according to some embodiments of the invention;

FIG. 31 is a simplified schematic of a section of a structure including low foreshortening, according to some embodiments of the invention;

FIG. 32 is a simplified schematic of a section of a structure with low foreshortening, according to some embodiments of the invention;

FIG. 33 is a simplified schematic of a contracted connector, according to some embodiments of the invention;

FIG. 34 is a simplified schematic of an extended connector, according to some embodiments of the invention;

FIG. 35 is a photographic side view of an exemplary structure which has been bent, according to some embodiments of the invention;

FIG. 36 is a simplified schematic of a section of a structure including kink resistance, according to some embodiment of the invention;

FIG. 37 is a simplified schematic of a section of a structure including kink resistance, according to some embodiments of the invention;

FIG. 38A is a simplified schematic front view of a crimped stent, according to some embodiments of the invention;

FIG. 38B is a simplified schematic axial cross section of a crimped stent, according to some embodiments of the invention;

FIG. 38C is a simplified schematic front view of a deployed stent, according to some embodiments of the invention;

FIG. 38D is a simplified schematic axial cross section of a deployed stent, according to some embodiments of the invention;

FIG. 38E is a photographic top view of a exemplary structure with a second portion protruding into a structure lumen, according to some embodiments of the invention;

FIG. 39 presents a plot of measured crush resistance with deflection, for an exemplary embodiment of the invention;

FIG. 40 presents a plot of measured crush resistance with deflection, for a stent of the art;

FIG. 41 is a simplified schematic cross sectional view of a structure, according to some embodiments of the invention; and FIG. 42 is a simplified schematic cross sectional view of a structure, showing various layers therein, according to some embodiments of the invention.

DESCRIPTION OF SPECIFIC EMBODIMENTS OF THE INVENTION

The present invention, in some embodiments thereof, relates to an expandable structure and, more particularly, but not exclusively, to an expandable structure for deployment in a lumen.

Overview

A broad aspect of some embodiments of the invention relates to balancing between forces applied by various parts of an expandable structure, especially for use in structures having a shape memory portion.

An aspect of some embodiments of the invention relates to an expandable structure (e.g. a stent) including at least a shape memory material (SM) portion and a second portion, where the SM portion includes strain induced behavior. The second portion is mechanically coupled to the first portion, for example being in an overlaying layer, and interferes with the relaxation of the first, SM, portion. In some embodiments, straining the SM portion reduces a SM portion expanding force. In some embodiments, reduction of SM portion expanding force is used to design a structure where, when the structure is in a crimped state, SM portion expanding force is low, for example, below a second portion expansion force (e.g. 50 MPa or less). In an exemplary embodiment of the invention, the SM expanding force is at least 10%, 20%, 30% or more (or intermediate percentages) less than the SM resisting force.

In some embodiments, when the structure is in a crimped state, the SM portion is highly strained. In some embodiments, a SM portion shape memory state (relaxed state) has a larger diameter than a crimped diameter. In an exemplary embodiment of the invention, the SM portion is treated (and sufficiently strained) so that the reduction in expansion force is at least 30%, 50%, 70%, 80% or intermediate percentages as compared to the same structure without treatment.

An aspect of some embodiments of the invention relates to a composite stent including a SM portion where the SM portion has different unloading stress and/or force, for different strains. In some embodiments, the SM portion has a different unloading stress/force, corresponding to crimped configuration strain, to an unloading stress/force corresponding to deployed configuration strains. For example, the difference can be, for example that the unloading force in crimped configuration is reduced by at least 30%, 50%, 70%, 80% or intermediate percentages as compared to a deployed configuration (e.g., a stent with a radius greater by a factor of 2, 3 or intermediate or greater factor). For non-tubular elements, "crimping" is provided by a change in length of the SM elements.

In some embodiments, the SM portion is treated such that the SM portion has an expanding force which decreases as a function of strain. In some embodiments, treatment comprises heat treatment. In some embodiments, the SM portion is treated such that it has a relaxed shape memory configuration (e.g. a tubular SM portion has a shape memory diameter). In an exemplary embodiment of the invention, the structure is designed to take this decrease into account, for example, to identify a suitable matching polymer whose hysteresis graph lies within a range between the higher expanding force and the lower expanding force of the SM portion.

In some embodiments, the SM portion is restrained by the second portion, where the second portion prevents and/or limits expansion of the SM portion. In one type of structure (e.g., a stent) the SM portion is predisposed to radially expand, while the second portion resists such expansion. In an alternative structure, the SM portion would contract and the second portion would resist such contraction. In some embodiments, the resistance is by force caused by elastic or super elastic relaxation. Optionally or alternatively, the resistance is by a force caused by resistance to plastic or super-plastic and/or other deformation.

In some structures (stent or otherwise) the forces are not symmetric (rotationally and/or axially) and/or radial. For example, in a stent, a resisting force at one location may be smaller than at a different one and/or a SM force at one location may be larger at another location. This may cause the structure to bend and/or exhibit other asymmetric properties. Optionally, the force applied during bending is selected to be small. This may allow, for example, for a device to adapt to a shape of a surrounding lumen, but not enforce a particular curvature thereon.

In some embodiments, not all the structure is expandable and/or expands in a same direction. For example, one part may radially expand while another part is designed to maintain a fixed radius (e.g., not include expandable portions), and/or while a third part radially contracts. Optionally or alternatively, one part may be self expanding while another part be balloon expandable. Also, a structure can be balloon expandable and once sufficiently expanded, may exhibit self-expansion properties. The converse is also within the scope of some embodiments of the invention, namely that the structure self expands up to one radius and is balloon expandable after.

In an exemplary embodiment of the invention, a stent as described herein shows a low recoil, for example, less than 10%, 5%, 3%, 1% or intermediate percentages of recoil in diameter after deployment.

An aspect of some embodiments of the invention relates to an expandable structure which is substantially stable in more than one configuration. For example, the expansion and/or contraction force applied by the structure may be less than a threshold. In an exemplary embodiment of the invention, the threshold is substantially zero. Optionally or alternatively, the threshold is less than 50%, 30%, 20%, 10%, 5% or intermediate percentages of the force applied by any part of the device at that configuration. In an exemplary embodiment of the invention, the device is formed of a SM portion and a second portion, optionally polymer, but optionally, formed of other materials, for example, SM. In an exemplary embodiment of the invention, at least 10%, 20%, 30%, 40%, 50% or intermediate percentages by volume of the structure are formed of a SM material.

In some embodiments, a structure is stable in a crimped state and a plurality of expanded states, optionally covering a continuum. For example, in some embodiments, a tubular structure has a continuum of ranges of diameters. In some embodiments, a deployed diameter is 1.5-3 times a crimped diameter, for example, between 1.7 and 2.8. Optionally or alternatively, the range covers a factor of at least 1.5, 2, 3, 4 or intermediate or greater ranges of diameters.

Optionally, the stable range (e.g., deployed for a stent) is separated from a stable configuration (e.g., crimped for a stent) by an unstable region. Optionally or alternatively, the stable range may consist of a plurality of stable points (e.g., be discrete), for example, 3, 4, 5, or more separated by configuration which tend towards a nearby stable point.

In some embodiments, the SM portion and the second portion are configured such that the SM portion is configured to apply an expanding force and the second portion has a reactive contracting force to the expanding force. In some embodiments, the structure is stable as the SM portion expanding force and the second portion reactive contracting force are balanced.

A potential benefit of balanced forces is, in some embodiments, the structure exerts substantially no outwards force. For example, for a tubular structure, the structure exerts substantially no radial outwards force. In some cases, the force exists, but is low enough that it can be counteracted by the surrounding lumen. Optionally or alternatively, the force is absent due to hysteresis behavior of one or both of the portions or due to a portion exhibiting plastic deformation resisting the deformation implied by the net force applied by the two portions.

In an exemplary embodiment of the invention, while the applied outwards force is low, the resistance to crushing is considerably greater, for example, by a factor of 2, 3, 5, 7, 10, 15, 20 or intermediate numbers. It is noted that in regular SM stents crush resistance is often 50% or less of radial force. In some embodiments of the invention crush resistance is lower in absolute number numbers (10-30% lower, for example as compared to a SM stent of similar design. However, as radial force is so low, greater ratios can be achieved.

In some embodiments, a structure is configured such that a SM portion expanding force is less than a force required to expand the second portion (a second portion expansion force) and the second portion contracting force is less than a force required to contract the SM portion (a SM contraction force).

In some embodiments, there are a range of stable deployed configurations. In some embodiments, a tubular structure has a range of stable deployed diameters. In some embodiments, stable deployed diameters are between a SM portion shape memory diameter (e.g., in a memory state) and a second portion relaxed diameter.

In some embodiments, the structure has high resistance to radial crimping forces, for example, corresponding to a SM portion loading force. In some embodiments, loading or crimping of the SM portion follows a stress-strain curve including an elastic portion with strain proportional to stress, followed by a superelastic portion where small increases in stress correspond in large strains (loading plateau). In some embodiments, the SM portion unloading plateau has high stress/forces, corresponding with high forces required to radially crimp the structure. A potential benefit of high forces required to crimp the structure, is structure resistance to collapse. In some embodiments, loading plateau forces of the SM portion are for example, between 50 and 1000 MPA, for example, between 200 and 700 MPA, for example, approximately 450 MPa.

In some embodiments, the structure elastically deforms under low strain. In some embodiments, under a low strain, the SM portion behaves elastically (e.g. remaining martensite). In some embodiments, under a low strain the second portion behaves elastically or plastically and/or does not interfere with the elastic behavior of the SM portion. For example, when a unidirectional crushing force is applied and removed, the structure returns to an original deployed configuration. In some embodiments, the reactive force (to the crushing force) of the second portion (e.g., a polymer portion), is almost zero, corresponding to a small strain of the polymer portion. Once local pressure P1 is removed, for example, as the polymer portion has not significantly changed in circumference, the SM portion returns to a pre-deformation deployed configuration.

In an exemplary embodiment of the invention, the SM material is selected to have a strong memory, so that the range over which this elastic behavior is exhibited is large enough for, for example, resistance to deformations of between 0.1 and 10% of the diameter of the structure. Such resistance can correspond to SM material strain of between 0.1% and 2%, for example, depending on stent design parameters.

In some embodiments, the SM portion includes temperature dependent characteristics. In some embodiments, the SM portion expanding force changes upon a temperature change.

For example, in some embodiments, a temperature change reduces the SM radial resistance force (e.g. below the contracting force of the second portion) and the structure collapses and/or self-crimps and/or otherwise deforms.

For example, in some embodiments, a temperature change increases the SM expanding force (e.g. above a radially contracting force of the second portion) and the structure expands and/or self-deploys.

In some embodiments the structure is tubular. In some embodiments, the structure is a tubular mesh or lattice with multiple apertures therein and a coverage percentage of, for example, between 1% and 70%, for example, between 10% and 50%, for example, between 15% and 25%. In some embodiments, the structure is shaped to be used as a stent. In some embodiments, the SM portion is tubular and/or the second portion is tubular.

In some embodiments, the structure includes a plurality of axial segments (e.g., between 2 and 10, for example, between 3 and 5). In some embodiments, segments are coupled by a plurality of connectors. In one design family, the SM portions are provided as discrete segments interconnected by the second portion. Optionally, this provides a plurality of bending points where properties of the second portion dictate the bending properties of the device, optionally increasing flexibility. Optionally or alternatively, SM interconnectors are used. Optionally, the connectors are treated to not exhibit SM behavior at the working temperatures used.

In an exemplary embodiment of the invention, the SM segments are interconnected by an overlying tube comprising at least part of the second portion. The ends of this tube optionally extend past one or both ends of the outermost SM segments.

In some embodiments, an axial geometry enclosed by the structure, when in a relaxed state and/or uniformly expanded state is rotationally symmetrical (e.g., to within 10% variation in diameter at each axial location and/or ignoring axial bending). For example, in some embodiments, a tubular structure has a circular axial enclosed geometry. In some embodiments, an axial geometry enclosed by the structure, varies at different points along a structure length. For example, in some embodiments, different segments have different axial geometries enclosed by the structure. For example, a structure with a first tubular segment and a second tubular segment has, in some embodiments, a first segment deployed diameter larger than a second segment deployed diameter and/or having a different design (e.g., surface pattern). A potential benefit of a different enclosed axial geometries/properties along a structure length is better conformability of the deployed structure (e.g. to a lumen), as compared to a stent with uniform axial behavior.

In some embodiments, an axial geometry enclosed by the structure at one or more points along a structure length is asymmetrical, for example, the axial geometry enclosed by the structure is oval. A potential benefit of asymmetrical enclosed axial geometries is good conformability of the deployed structure (e.g. to a lumen).

In some embodiments, one or more segment SM portion has a different treatment from other segments. In some embodiments, one or more segment SM portion and/or polymer portion has different geometry e.g. one or more of axial geometry, thickness, length and/or surface aperture pattern and/or dimensions.

In some embodiments, each segment includes a SM portion and a second portion. In some embodiments, connectors are flexible. A potential benefit of flexible segments is flexibility of the crimped stent for ease of deployment and/or conformability of the deployed stent to a lumen.

In some embodiments, connectors do not include SM material. In some embodiments, connectors include second portion material (e.g., such as polymer). In an exemplary embodiment of the invention, a first segment is connected to a second segment by between 1 and 7, for example, between 2 and 5, circumferentially arranged connectors. Different inter-segment portions may have different numbers and/or positioning and/or relative circumferential positioning of the connectors.

In some embodiments, connectors include SM material. In some embodiments connectors are formed of both SM material and material as used in the second portion (e.g., a polymer).

In some embodiments, the SM portion includes a shape memory alloy (SMA), for example Fe—Mn—Si, Cu—Zn—Al, Cu—Al—Ni, NiTi. In some embodiments the SM portion is nitinol (NiTi). In some embodiments, the SM portion includes a NiTi-based ternary alloy, for example NiTi—Cu, NiTi—Co, NiTi—Pd, NiTi—Pt, NiTi—Zr, NiTi—Hf.

In some embodiments, the second portion exhibits elastic hysteresis. In some embodiments, the second portion includes polymer or a high-recoil polymer. Exemplary polymers which may be used (e.g., with exact properties possibly selected according to the application, possibly using principles as described herein, include: Silicone elastomer, Silastic elastomer, Polyurethane, carbosil, Desmopan (Bayer), Carbothane (Lubrizol), Tecothane (Lubrizol), Tecoflex (Lubrizol), ChronoFlex® C; CarboSil (DSM), Texin (Bayer) etc.

In some embodiments, a method of use of a structure includes inserting the structure into a lumen in a crimped configuration and expanding the structure to a deployed configuration inside the lumen (e.g. expanding on an inflatable balloon and/or self-deploying e.g. upon a temperature change).

An aspect of some embodiments of the invention relates to an expandable structure exhibiting SM and/or elastic behavior which is deployed using balloon expansion over the range of deployment states where SM and/or elastic behavior is exhibited by the component parts of the structure. A potential benefit of balloon deployment is control of expansion speed, positioning and/or extent.

In some embodiments, the structure is expanded using a compliant balloon (e.g. using a low inflation pressure for example, using an inflation pressure of 0.1-5 atmospheres, or 0.3 to 2 atmospheres). A potential benefit of structure deployment using a compliant balloon is a highly conformed stent shape to lumen geometry.

In some embodiments, the structure is expanded using a non-compliant balloon (e.g. of 5-15 atmospheres, or 5-8 atmospheres, or 12-15 or 18 atmospheres, or about 8 atmospheres). A potential benefit of structure deployment using a non-compliant balloon is that the stent can be used to open and/or enlarge a lumen (e.g. a body lumen), according to the balloon size (e.g., combined PCTA and stenting, direct stenting).

In some embodiments, a method of use of a structure includes deploying the structure more than one time, for example, redeploying (e.g. for correct positioning), where the structure is crimped (e.g. self-crimped) in between deployments.

In some embodiments, a method of use of a structure includes removing the structure a time period after deployment, for example, by self-crimping the structure onto a deployment/removal device (e.g. a catheter).

An aspect of some embodiments of the invention relates to an expandable structure where a length of the structure remains substantially the same in crimped and deployed configurations. In some embodiments, the structure includes a plurality of coupled flexible members and a plurality of rigid members where the rigid members are orientated generally axially (e.g., a centerline thereof lying, within 30 degrees of parallel to the axis) along the structure. In some embodiments, axially orientated rigid segments are interconnected by connectors which can morph to accommodate difference in expansion of different segments. Optionally, each such segment optionally includes one or more of the struts described below.

In some embodiments, each rigid member is coupled to two other rigid struts and each coupling is by at least one flexible member. In some embodiments, when the structure expands and/or contracts (deploys and crimps respectively) the flexible members bend during contraction and unbend during expansion of the structure. In some embodiments, bending of the flexible members brings the rigid members together (crimping) and unbending pushes the rigid members apart (deploying).

An aspect of some embodiments of the invention relates to an expandable structure where the structure is kink resistant, the structure bends without closing the structure at a bend and/or substantially (e.g., by more than 20%, 10%, 5% or intermediate percentages) decreasing an axial geometry enclosed by the structure at the bend (e.g., the structure which is defined if all the apertures in the surface are filled in with sections that match a general curvature of the surface. In some embodiments, the structure includes a plurality of circumferential segments, where segments are coupled using connectors. In some embodiments, connectors are axially compressible and/or expandable. In some embodiments, at a bend, connectors expand at the outer side of the bend and/or contract at the inner side of the bend. In some embodiments, connectors each include one or more flexible strut, each flexible strut comprising a vertex around which the strut bends axially to compress the connector. In some embodiments, one or more connector includes at least one rhombic shape or other closed shape. Optionally, the shape increases a flexibility of radially resistant surfaces and/or provides such flexibility between them).

An aspect of some embodiments of the invention relates to a balloon expandable composite stent including at least one metallic and at least one polymer parts, co-existing in force equilibrium. In some embodiments, the metallic part is made of shape memory material with strain induced martensite behavior where transformation temperatures from martensite to austenite A's, A'f in a crimped configuration (deformed) are different to As, Af temperatures in an expanded configuration. Where A's>As, A'f>Af. In some embodiments and polymer part is made of a polymer with high elastic recoil. In some embodiments, the stent has three configurations, a crimped configuration with a small diameter, an expanded configuration with a large diameter and a self-crimped configuration with an intermediate diameter. In some embodiments, in the crimped configuration the polymer part eliminates expansion of the metallic part before stent deployment, enforces the metallic part and all of the stent after deployment, makes the stent highly conformable, eliminates chronic outward forces from the stent on the lumen walls and provides a self-crimping feature during stent removal. In some embodiments, the metallic part after deployment eliminates/decreases post deployment stent recoil and provides stent crush resistance.

In an exemplary embodiment of the invention, stent recoil (e.g., percentage by which the diameter of a stent decreases from its expanded diameter (when the balloon is inflated at the nominal pressure) to its relaxed diameter (when the balloon is retrieved from the stent) (or increases), is less than, for example, 10%, 5%, 3%, 2%, 0.5% or intermediate percentages.

An aspect of some embodiments of the invention relates to a balloon expandable composite stent including at least one metallic and at least one polymer portion, co-existing in force equilibrium where the metallic part is made of shape memory material displaying decreasing of lower plateau in mechanical hysteresis curve with increasing deforming strain (FIG. 6) and the polymer part is made of a polymer with high elastic recoil. In some embodiments, the stent has three configurations: a crimped configuration with small diameter, an expanded configuration with large diameter and a self-crimped configuration with intermediate diameter. In some embodiments, in the crimped configuration the polymer part eliminates expansion of the metallic part before stent deployment, enforces metallic part and all of the stent after deployment, makes the stent highly conformable, eliminates chronic outward forces from the stent on the lumen walls and provides a self-crimping feature during stent removal. In some embodiments, the metallic part after deployment eliminates/decreases post deployment stent recoil and provides stent crush resistance.

In some embodiments, when the stent is deformed to a small strain (e.g. $\varepsilon 1$, FIG. 6), the metallic part has a lower plateau force (e.g. F1, FIG. 6) and an upper plateau force (e.g. F2, FIG. 6). In some embodiments, when the stent is deforming to a crimping configuration (e.g. $\varepsilon 3$, FIG. 6), the lower plateau force is e.g. F"1 (FIG. 6), and polymer part expansion force is e.g. F4 (FIG. 6) and elastic recoil force is e.g. F5 (FIG. 6) so that F4>F"1 providing safe force equilibrium in the crimped condition, F2>F5 that provides safe force balance in deployed condition and F1>F4 that provides crush resistance of the stent.

In some embodiments, the polymer part has high recoil. In some embodiments, at low temperatures Fpoly (F5) is above Fniti (F2(T)).

In some embodiments, low temperature is reached by cold fluid flush and stent self-crimps over a retrieving catheter.

In some embodiments, the SM portion has at least two segments with different design, for examples so that the SM portion provides different support in different stent areas and/or provides enhanced conformability and/or high migration resistance.

In some embodiments, at least two nitinol segments (SM portions) have different free diameters, potentially enhancing stent conformability and/or migration resistance.

In some embodiments, at least two nitinol segments have a different pattern structure, potentially enhancing conformability and/or migration resistance.

An aspect of some embodiments of the invention relates to a delivery system including a high pressure balloon. In some embodiments, a high pressure balloon delivery system is be used for direct stenting and the balloon opens a duct according to balloon shape and/or size.

An aspect of some embodiments of the invention relates to a delivery system including a low pressure balloon with high compliance. In some embodiments, a low pressure balloon with high compliance, during direct stenting, the balloon potentially conforms stent shape to duct geometry.

In some embodiments, at least two polymer segments have a different pattern structure.

An aspect of some embodiments of the invention relates to a stent design including main radial resistant patterns providing zero recoil in an axial direction.

An aspect of some embodiments of the invention relates to a stent comprising flexible and rigid members connected to each other where distances between connection points do not change when the named members are crimped.

An aspect of some embodiments of the invention relates to a stent design including flexible nitinol connection between main radial resistant patterns. In some embodiments the connection includes a rhomb link flexible pattern, potentially providing excellent stent flexibility in a crimped condition and/or excellent conformability in a deployed condition.

An aspect of some embodiments of the invention relates to a stent design including flexible polymer connection between main radial resistant patterns. In some embodiments the connection includes a rhomb link flexible pattern, potentially providing excellent stent flexibility in a crimped condition and/or excellent conformability in a deployed condition.

An aspect of some embodiments of the invention relates to a balloon expandable composite stent, comprising at least one metallic and at least one polymer portion, wherein metallic portion made of shape memory alloy (SMA). In some embodiments, the stent has three different configurations: a first configuration with small diameter, d, in a crimped condition; a second configuration with a large diameter, D, in a deployed condition and a third configuration with an intermediate diameter, d1, in a self-crimped condition, where D>d1>d.

In some embodiments, a SMA of a metallic portion possess a strain induced martensite feature (e.g. as described in U.S. Pat. No. 5,876,434). In some embodiments, the strain framework varies from small strain, (e.g. ε1, FIG. 6) in a deployed condition to a maximal strain (e.g. ε3, FIG. 6), such that a SMA transformation temperature from martensite to austenite in a deployed condition is A, a SMA transformation temperature from martensite to austenite in a crimped condition it is A" and A" is significantly (at least 5° C.) above A (for example, Af=15° C., Af=22° C.).

In some embodiments, a polymer portion is made of polymer that possesses high recoil. In a crimped condition the polymer portion co-exists with the SMA portion in a stable force equilibrium and eliminates SMA portion expansion. This equilibrium is stable at body temperature, because active martensite-austenite transformation temperature, A, increases from A to A" and therefore its expansion force decreases and for polymer portion is easier to eliminate expansion of the SMA part.

In some embodiments, the force equilibrium between the polymer and SMA portions can be shifted by an external factor. In some embodiments, the external factor is an external force assisting SMA portion expansion. In some embodiments, this force is applied by balloon dilatation in composite stent deployment.

In some embodiments, when the stent is deployed due to balloon expansion, the SMA portion transforms from the state with large strain (e.g. ε3, FIG. 6) to the state with small strain, ε1. At the same time, A" changes to A (U.S. Pat. No. 5,876,434, FIG. 3.

In some embodiments, in a deployed condition the SMA portion has decreased transformation temperature A<A" and correspondently increased radial resistance; therefore, in some embodiments, the polymer portion is not able to crimp the SMA portion and both portions are in stable equilibrium in the stent deployed condition. In some embodiments, the term "stable equilibrium" is a physical term, referring to a state where small attempts to change the stent shape leads to a force returning the stent back to equilibrium.

In some embodiments, a deployed stent SMA portion exists in slightly crimped condition with strain ε1, but a polymer portion decreases SMA portion outward force to almost zero. At the same time, SMA portion resists polymer portion recoil, decreasing it almost to zero. In some embodiments, the polymer portion in expanded condition creates a flexible connection between SMA portions that potentially provides high stent conformability.

In some embodiments, a composite balloon expandable stent in a deployed condition has crush resistance. Usual mode for crushing is two plate pressure, which is different from radial crimping. In some embodiments, during crushing SMA portion strain varies around δ1 within narrow framework, keeping the same SMA portion expansion outward force. In some embodiments, the polymer portion resistance change to crushing is more sharp and allows the SMA portion to expand the polymer portion after crushing.

For example, the polymer is selected to react to straining of 200-400% with a change I reactive force of a factor of 3-7.

In some embodiments, the force equilibrium between SMA and polymer portions may be shifted by changing radial resistance of SMA portion. In some embodiment, the external factor is temperature change. In some embodiments, local cooling of a SMA portion leads to decreasing of its radial resistance below the recoil force of polymer portion. As a result, in some embodiments, a polymer portion recoil force leads to composite stent self-crimping to the next equilibrium, when stent has intermediate diameter d1>d.

In some embodiments, the SMA portion displays strain induced martensite behavior (e.g. per U.S. Pat. No. 5,876,434), in unloading from different deformed conditions (e.g. with different strains). In some embodiments, unloading is through different unloading (lower) plateaus (e.g. FIG. 6). In some embodiments, when the stent is in a crimped condition and the SMA portion is deformed with large strain (e.g. ε3, FIG. 6), the SMA portion would like to unload and to provide outward force (e.g. F"1, FIG. 6). In the crimped condition, the polymer portion resists the SMA portion outward force with polymer portion expansion force, e.g. with force F4>F1" (FIG. 6). In some embodiments, such a relation between forces exerted by SMA and polymer portions potentially leads to a very stable stent crimped condition e.g. within the body.

In some embodiments, in order to deploy the stent, the stent is expanded from a crimped condition, by an external factor e.g. expansion force of balloon inflation. In some embodiments, the sum of outward SMA and balloon force exceeds a polymer portion expansion force (e.g. F4, FIG. 6) and the composite stent deploys, expanding from diameter d to diameter D. Due to geometrical changes, the SMA portion strain also changes from large strain ε3 to small strain ε2 and therefore, according to FIG. 3 transformation temperature A changes from elevated A" to low A, that leads to change in unloading plateau (FIG. 6), that changes from F1" to F1'. In some embodiments, expansion force of the SMA portion increases after deployment from F1" to F1' (e.g. FIG. 6). Stent expansion leads to polymer portion deforming and increasing of its expansion force F4 above F1' and recoil force F5 below F1' (FIG. 6). In some embodiments, in a deployed condition, polymer portion resists SMA portion expansion, decreasing stent outward force almost to zero. At the same time, a recoil force of the polymer portion, (e.g. F5, FIG. 6) is not enough to crimp the SMA portion (e.g. F5<F2, FIG. 6), decreasing stent recoil almost to zero. In some embodiments, the polymer portion in an expanded condition creates a flexible connection between SMA portions that potentially provides high stent conformability.

In some embodiments, a composite balloon expandable stent in a deployed condition is crush resistant.

Usually, crushing is modeled with pressure between two plates, which is different to radial crimping. In some embodiments, during crush deforming, stent strain varies within small framework around strain ε1 and expansion force is remains almost constant and equal to F1. In some embodiments, the polymer portion more sharply changes its forces, therefore after crushing F1 is above F4, potentially providing crush resistance, restoring of uncrushed shape.

In some embodiments, the force equilibrium between SMA and polymer portions in a deployed condition is shifted by changing a radial resistance of the SMA portion using an external factor of temperature change. In some embodiments, local cooling of the SMA portion leads to decreasing of SMA portion radial resistance below the recoil force of polymer portion. As a result, polymer portion recoil force leads to composite stent self-crimping to a next equilibrium, when stent has intermediate diameter d1>d.

In some embodiments, a stent in a deployed condition is self-crimped by cold saline flushing within the SMA portion. In some embodiments, upon cooling, a radial resistance of SMA portion decreases e.g. so that F2 (FIG. 6) drops below recoil force F5 of polymer portion (FIG. 6) and, for example, a polymer portion crimps the SMA portion over a retrieving catheter e.g. between retrieving catheter distal and proximal stoppers. In some embodiments, stoppers on the retriever catheter potentially prevent the stent from sliding (e.g. off the catheter) during removal of the stent from the body. In some embodiments, a distal stopper (e.g. on the free end of the retrieving catheter) is manufactured as a small low pressure balloon. In some embodiments the distal stopper balloon is deflated when the catheter inserts into deployed stent and is inflated when the catheter pulls out of the body.

In some embodiments, a retriever catheter has side holes through which saline (e.g. cold saline) is flushing. In some embodiments, side holes are situated between distal and proximal stoppers and stent self-crimps over the catheter between the stoppers.

In some embodiments, at least two segments of SMA portion have different design, for example that provides different expansion outward force and/or different radial resistance of different stent segments. In some embodiments, the polymer portion has a uniform design over the entire stent length. A potential benefit of a stent with different SM portion design and optionally uniform polymer portion design is enhanced conformability and/or migration resistance. In some embodiments, different design of the SMA portion includes different cell pattern designs and/or different SMA portion free diameters.

In some embodiments, different segments of polymer portions have different design, for example, contributing to different expansion resistance and different crimping recoil force for different stent segments. A potential benefit is enhanced stent conformability and/or migration resistance.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Structure with Stable Crimped and Deployed Configurations

Figure 1A:
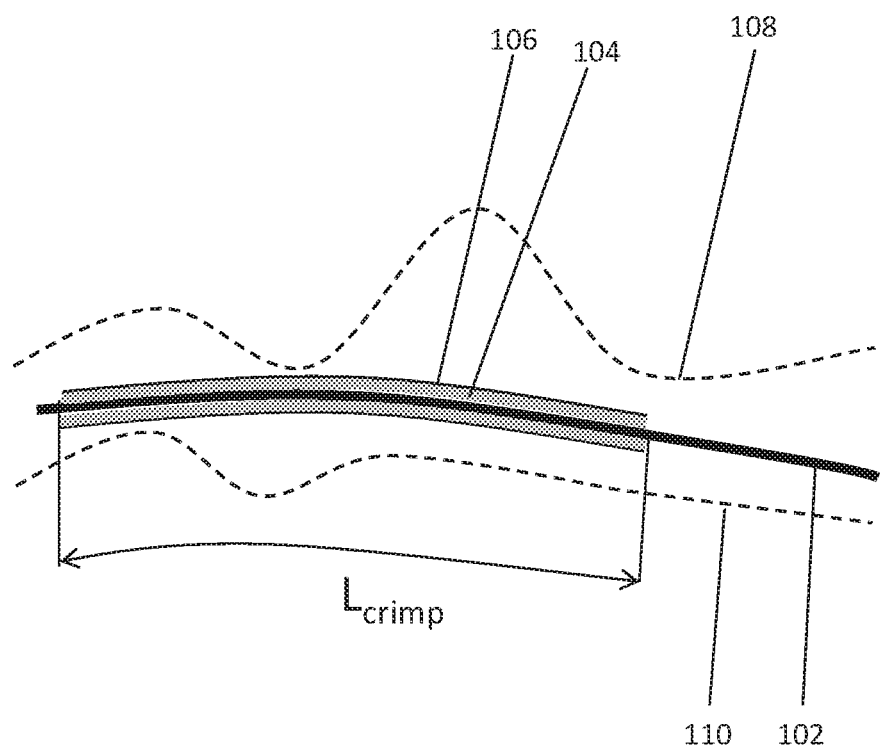

Referring now to the drawings, FIG. 1A is a simplified schematic cross sectional view of a structure in a crimped configuration within a lumen 100, according to some embodiments of the invention. In some embodiments, the structure is delivered to lumen 100, and/or a target portion of lumen 100, by a deployment device 102 (e.g. catheter). In some embodiments, the structure includes a SM portion 104 coupled to a resistive second portion 106, for example, and elastic portion (e.g. polymer). In some embodiments the portions are coupled such that SM portion 104 is contained within or held by second portion 106.

In an exemplary embodiment of the invention, the lumen is a body lumen and the stent is formed of and/or coated with bio-compatible materials. In an exemplary embodiment of the invention, the lumen is a natural lumen such as a blood vessel (e.g., artery or vein), part of GI tract (e.g., esophagus, stomach, duodenum, small intestine, large intestine or rectum), urethra, ureter, part of a kidney, bronchi and/or sinus cavities. Optionally, the stent is provided sterile, optionally in sterile packaging and/or with instructions for use. Optionally or alternatively, the stent is used for artificially formed lumens, such as to separate tissues and/or for apertures formed in organs (e.g., the skin).

The application may determine one or more desirable stent properties, such as one or more of length, crimped diameter, maximum deployed diameter, range of stable diameters, degree of conforming, crush resistance and/or maximum applied radial force. In an exemplary embodiment of the invention, such properties are achieved using selection methods as described herein. For example, once stent properties are known, various options for design and properties of the SM portion and second portion can be matched to see which pairing provides a desired result. Optionally, a search is made of the space of such pairings to find a best or satisfactory match between the stent design and the properties. As can be understand, the above properties can be modified, for example, by selecting portion strength, amount of induced strain and/or relaxed geometry. In an exemplary embodiment of the invention, the geometry of the stent is selected according to the desired amount, uniformity and/or location of induced strain (and/or e.g., affect of crimping on stent behavior and/or properties when deployed of a crimped stent). As noted herein, the amount of strain affects self-expansion force, in some stents according to exemplary embodiments of the invention. So, for example, a stent where more of the strain is concentrated at certain joints, will exhibit a lower self-expansion than a stent where the strain is more evenly spread over the stent (e.g., when entire struts are deformed, rather than just joints thereon) and, hence, in general lower and less affecting (reducing) of the expansion forces. In an exemplary embodiment of the invention, designs are selected (e.g., as appropriate) where 10%, 20%, 40%, 70%, 80% or intermediate or greater or smaller percentages of the stent carry at least 50% or 80% of the strain. In accordance with some embodiments of the invention, greater percentages of stent carrying strain generally indicate a more uniform straining and hence a lessor reduction in self-expansion forces.

For example, for smaller blood vessels (lower extremity, for example) stent (total, composite) thickness can be 0.05-0.5 mm thickness, for example, 0.08-0.3 mm, for example, 0.1-0.15 mm in deployed condition with length, for example, up to 150 mm (e.g., 20, 40, 80 or intermediate or greater length), and/or with surface coverage of between 5% and 60%, for example, between 10-30%. For large vessels (SFA) or GI (biliary & esophageal) SM portion is optionally 0.1-0.9 mm, for example, 0.15-0.4 mm thick and Poly portion is 0.05-0.6 mm, for example, 0.1-0.4 mm thick (e.g, varied between normally open and normally closed stents), length, for example, up to 200 mm (e.g., at least 10, 20, 40, 80, 150 or intermediate length in mm), and/or surface coverage from 20 to 95%, for example, between 25 and 45%.

In some embodiments, the crimped structure is small enough to be inserted into a lumen 100, e.g. thinner than a minimum distance between lumen walls 108, 110. In some embodiments, the crimped structure is 3.5-4.5 mm diameter or 3-5 mm diameter. In some embodiments, the crimped structure is less than 3.5 mm in diameter, e.g. 1-1.5 mm. In some embodiments, the crimped structure is more than 4.5 mm in diameter. Crimping ratio can be (ratio between crimped and deployed state), for example, between 1:2 and 1:10, or intermediate numbers, or greater, depending on the stent design.

Figure 1B:
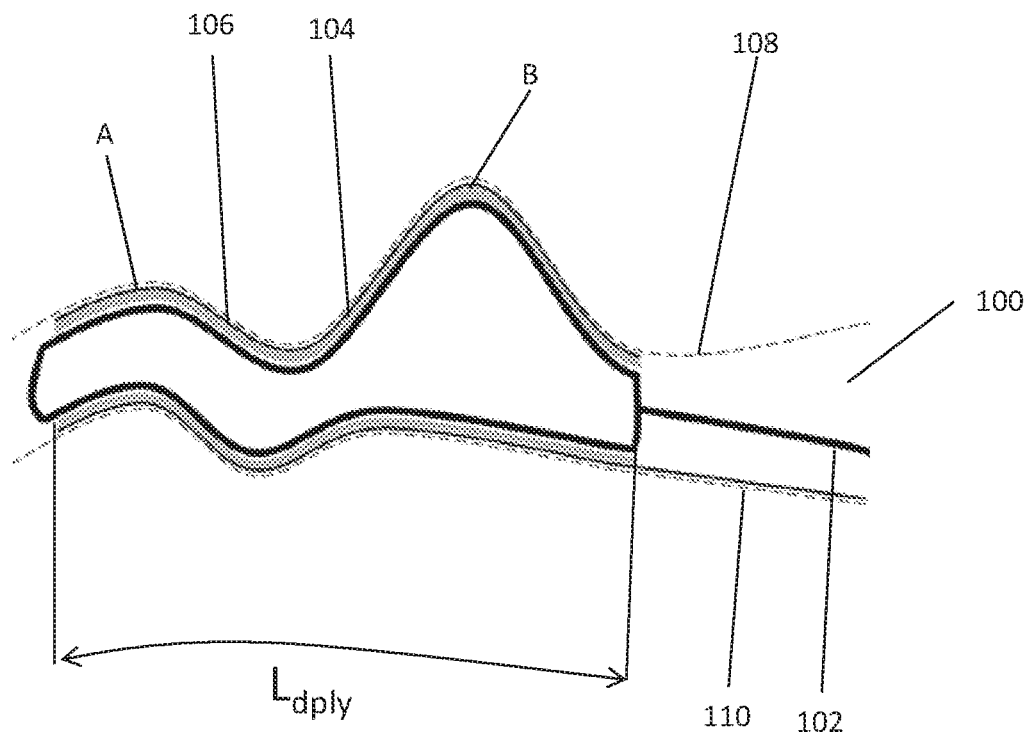

FIG. 1B is a simplified schematic cross sectional view of a structure in a deployed configuration within a lumen 100, also showing optional adaptation to the lumen, according to some embodiments of the invention.

In some embodiments, the structure is expanded into a deployed configuration by a deployment device 102. In some embodiments, the structure is deployed by expansion of at least a portion of deployment device 102, for example, by inflation of a balloon.

FIG. 1B shows a possible consequence of structure balance in a range of configurations, e.g. a range of deployed diameters. In some embodiments, the structure, in a deployed configuration, has more than one diameter and/or axial geometry enclosed by the structure along a structure length: a structure transverse dimension at point A along length $L_{dply}$ of the structure is smaller than a structure transverse dimension at point B.

Apparent Composite Stents of the Art

Described in the art are composite stents including a SM portion and a plastic portion, however, as will be explained below, it is not clear that such are possible. FIG. 2 presents a plot of applied stress, F, with strain, ε, for a SM portion and a plastic material portion of a composite stent described in the art. Hysteresis plot 50 shows the stress-strain relationship of the SM portion, where lower curve 51 corresponds to expansion of the stent (unloading of the SM portion) from the crimped configuration and where upper curve 52 corresponds to crimping of the stent. Hysteresis plot 60 shows the stress-strain relationship of the plastic portion where upper curve 62 corresponds to expanding of the stent and lower curve 61 corresponds to crimping of the stent.

Of note is hysteresis plot 50a, in particular, the lower curve, corresponding to expansion of the stent from a deployed configuration where the expanding force, F1 of the SM portion in the crimped configuration is the same as the expanding force of the SM portion in the deployed configuration.

The stent does not expand from a crimped configuration, where strain=εcrimped, since expansion of the SM portion exerts a force F1 which is less than the force required to expand the plastic portion, F4, F1<F4.

In a deployed configuration, e.g. εdeployed, the stent is stable, the stent does not expand, as F1<F4, and the stent does not collapse, as the relaxation or contraction force of the plastic portion, F5, is less than the force needed to crimp the SM material, F2 (F5<F2).

To expand or deploy the stent from the crimped configuration εcrimped, a force greater than or equal to, F=F1−F4 is applied.

Generally, for most materials, the upper and lower parts of the stress/strain hysteresis curve are similar, for example, F2=F1+δ, F4=F5+δ where δ is small. Therefore, although, theoretically, a match between a SM material and a plastic (or other material) such that F1<F4 and F2>F5 in the deployed configuration and where F1<F4 in the crimped configuration might be found, the inventors are not aware of any practical match. Even were such a match found, the size of the overlap is very small, effectively dictating a narrow or single range of stable diameters. In some embodiments of the invention, material treatment and/or stent design are selected to increase the possibility of a match with practical results, for example, as shown in the examples below.

FIG. 3 and FIG. 4 show two examples of ineffective material matching.

FIG. 3 presents a plot of applied force, F, with strain, ε, for a composite stent. F2>F5, but F1>F4, so a composite stent using these materials is stable when deployed, but is not stable in the crimped configuration.

FIG. 4 presents a plot of applied force, F, with strain, ε, for materials for a composite stent. F1<F4, but F2<F5, so a composite stent constructed using these materials is stable when in the crimped configuration, but the deployed stent is not stable and collapses back to the crimped configuration.

As explained herein (e.g., FIGS. 5, 6), in an exemplary embodiment of the invention, the properties of the SM material are modified such that a practical match is more easily found.

Exemplary Strain Dependent Material Characteristics

Generally, shape memory alloys transform from martensite crystal structure to austenite crystal structure upon heating. When heating, in a range of transformation temperatures between a transformation start temperature As and a transformation finish temperature Af (where As<Af), the alloy is neither austenitic or martensitic, and exhibits superelastic material characteristics. As the shape memory alloy is heated further, above Af, the memory alloy eventually reaches a temperature, Md, a maximal temperature when martensitic transformation occurs at stress.

Shape memory alloy transformation temperatures (e.g. As, Af) are generally known to be dependent from applied stress and are somewhat dependent on applied strain, As=As(ε), Af=Af(ε). However, generally, the influence of strain on transformation temperatures (where the strain is within the limit of SM devices being used, e.g., 0 to 8%) is small, e.g. up to about 1-2° C.

In some embodiments, a SM portion is treated such that transformation temperatures show high strain dependence. For example, the influence on transformation temperature can be, for example, 3, 4, 5, 7, 8, 10, 15, 20 degrees Celsius or intermediate or greater difference in transformational temperature, for shape memory in the 0-8% strain range.

In some embodiments, treatment is heat treatment, e.g. as described below. In some embodiments, a SM portion is treated and sized such that a difference in strain between a crimped configuration and a deployed configuration generates a transformation temperature change the SM portion expanding force such that the mechanical properties of the SM portion are as desired in relation to the second portion (e.g., as described above) in the crimped and deployed configuration. For example, in some embodiments, at 3% strain As=15° C. and Af=25° C., whereas, at 7% strain As=28° C. and Af=32° C.

In some embodiments, transformation temperatures, when the structure is in a crimped configuration, A's, A' f, are different to transformation temperatures, when the structure is in a deployed configuration. In some embodiments A's>As and/or A'f>Af (e.g., by the above noted differences).

FIG. 5 presents plots of shape memory material austenite transformation start temperature, As, and austenite transformation finish temperature, Af, with strain, for stent materials used according to some embodiments of the invention. FIG. 5 shows that, below temperature As'(ε) the material is martensite (solid gray shading), above temperature Af'(ε) the material is austenite (striped) and, above temperature As'(ε) and below temperature Af'(ε) the material is superelastic (white).

It should be noted with respect to FIGS. 5 and 6 (and some other charts herein), that what is shown are the shape-memory properties of the material from which the SM portion is constructed in accordance with some embodiments of the invention. However, in the body, actual forces are applied by the stent, not by component materials. The use of diagrams such as FIGS. 5 and 6 allows the effect of the stent structure to be ignored. It is noted, however, that some embodiments of the invention utilize the stent structure and/or stent crimping/deployment state, to affect how the material acts, for example, stent crimp amount and/or design can affect which part of FIG. 6 is traversed.

Referring to FIG. 5, for example, at a temperature Af0, for different strains, $\varepsilon_A$, $\varepsilon_B$ the shape memory material is at a different stage in the transformation; under strain $\varepsilon_A$ the alloy crystal structure is at the end of the transformation (at a border between superelastic and austenite), and under strain $\varepsilon_B$, the crystal structure is at the beginning of the transformation (at a border between superelastic and martensite). The differences in crystal structure are reflected in material characteristics, at the same temperature, for different applied strains.

In some embodiments, at a temperature range between room temperature and body temperature (e.g. 18° C.-39° C.), increasing the strain on a structure initiates a martensitic transformation in a SM portion of the structure, and reduces the expanding force of the SM portion. In some embodiments, increasing deforming strain on the structure and/or SM portion causes, for example decreasing of the mechanical hysteresis curve lower plateau. In an exemplary embodiment of the invention, a design can use these properties to select a desired curve, within the range possible for the material.

FIG. 6 presents a plot of stress-strain hysteresis curves for a SM portion and a polymer portion, according to some embodiments of the invention. It should be noted that the strain scale of the polymer plot is not the same as the SM plot, as polymers can often work under strain of 400-500%, while Nitinol may only work with strain up to 8%. In some exemplary embodiments of the invention, this difference in strain capability is used to provide different structures for the SM and second portions, with the SM being designed to reduce strain in all parts of the device to below 8%. A polymer section, for example, can have a small relaxed diameter (corresponding to desired crimp diameter) and still allow a great increase in diameter (e.g., a factor of 10 or more, such as 15 or 20) thereof during deployment.

Illustrated are three SM unloading curves $f_1(A_s)$, $f_1'(A_s')$, $f_1''(A_s'')$ each associated with unloading from a different strain on the SM portion: $F_1$ is associated with unloading from strain $\varepsilon_1$, $F_1'$ with $\varepsilon_2$, and $F_1''$ with $\varepsilon_3$, where $\varepsilon_1 < \varepsilon_2 < \varepsilon_3$. Each unloading curve includes an unloading plateau, $F_1$, $F_1'$, $F_1''$, which, for simplicity, is referred to as a single force value.

Exemplary Balance of Contracting and Expanding Forces

In some embodiments, a radially expanding force of a SM portion is balanced by a radially contracting force of a polymer portion. FIG. 7 is a simplified schematic of an uncoupled SM portion 704 and a second portion 706, according to some embodiments of the invention.

In some embodiments, SM portion 704, has a relaxed (e.g. shape memory) diameter, which is larger than that of a relaxed diameter of second portion 706; $D_{SM} > D_{poly}$. In some embodiments, coupling of SM portion 704 and second portion 706, for example, corresponds with stretching of second portion 706 and/or compression of SM portion 704. For example, in some embodiments, the polymer relaxed diameter is 75% or less, 50% or less, 25% or less, than the SM relaxed diameter. For example, in some embodiments $D_{SM}$ is approximately 12 mm and $D_{poly}$ is approximately 3 mm.

In some embodiments, for example, for force equilibrium at deployed diameters, $D_{SM}$ is larger than the largest deployed diameter.

In some embodiments, expanding a structure where SM portion 704 and second portion 706 are coupled such that and SM portion 704 is compressed and second portion 706 is stretched, corresponds with unloading or relaxing the SM portion and extending or loading the polymer portion. Referring now back to FIG. 6, expanding the structure corresponds with moving along curve F4 for the polymer and, depending on the strain applied to the SM portion, moving along one of the unloading curves f1(As), f1'(As'), or f1"(As").

In some embodiments, radially compressing, closing or crimping the structure corresponds with loading the SM portion and relaxing the polymer portion. Referring to FIG. 6, crimping the structure corresponds with moving along curve F5 for the polymer and moving along curve F2 for the SM portion.

In some embodiments of the invention, using a polymer portion to offset some of the SM portion properties allows a stronger SM material to be used, for example, more material or material with a stronger memory. In an exemplary embodiment of the invention, this translates into an elongation of the elastic loading of the curve in FIG. 6. Optionally, this curve is elongated by 20%, 40%, 50%, 60%, 80% or more relative to what is used for a same stent without the polymer layer.

Exemplary Heat Treatment

In some embodiments, a SM portion is treated such that, in a crimped configuration, the transformation temperature is at least 5° C. above the transformation temperature in a deployed configuration. For example, in some embodiments, a crimped configuration transformation temperature, Af=22° C. and a deployed configuration transformation temperature, Af=15° C.

In some embodiments, a SM portion is treated such that, in a crimped configuration, where $\varepsilon = \varepsilon_3 = 7\%$, D=2 mm, an unloading stress, F1", is approximately 50 MPa.

In some embodiments, a SM portion is treated such that, in a deployed configuration, where $\varepsilon = \varepsilon_2 = 2\%$, D=10 mm, an unloading stress, F1', is approximately 300 MPa.

In some embodiments, a SM portion is treated and/or a SM portion material is selected such that, a loading, resisting (crimping) stress, F2, is approximately 450 MPa.

Values intermediate, smaller and/or greater than the above values can be achieved as well and are limited only by the material properties, the above values being only exemplary.

In some embodiments, a SM portion is heated to a high temperature, then subjected to a solution treatment, constrained and subjected to a memorizing treatment and then to an aging treatment.

In some embodiments, a SM portion is subjected to a solution treatment, to a shape setting treatment and an aging treatment.

Generally, solution treatment is where a metal portion is heated to a temperature high enough to allow a constituent of the metal to enter into solid solution, and is then cooled rapidly (e.g. using water quenching) to hold that constituent in solution. Generally solution heat treatments soften.

Generally, memorizing treatment, or shape setting forms the material into a new memory shape. Memorizing treatment generally involves firmly constraining the material into a new shape (e.g. in a fixture or on a mandrel) and then performing a heat treatment. The heat treatment time should be such that the material reaches the desired temperature throughout its cross-section. The time will depend on the mass of the fixture and material, and the heating method.

Generally, aging treatments are done to raise the austenite finish (Af) temperature of superelastic Nitinol components.

Generally, aging is done by heat-treating to about 300-480° C. for extended periods. Generally, longer aging treatments are associated with higher Afs. For example, in some embodiments, a SM portion is subjected to the treatment described in Example 2 of U.S. Pat. No. 5,882,444: The SM portion is heated to 500° C. for 1 hour and then to a solution treatment at 650° C. for 20 mins. The SM portion is then constrained and subjected to a memorizing treatment at 520° C. for 30 mins, and then to aging treatment at 400° C. for 2 hours.

Other shape memory setting treatment and/or transformation temperature tailoring treatments of the art and/or other parameter values are suitable for use and are within the scope of some embodiments of the invention. In some exemplary embodiments of the invention, what is important is that the material be shown to exhibit a change in force due to applied strain, independent of the treatment method that achieves it; and that this change in force be utilized in stent design and/or usage.

In an exemplary embodiment of the invention, parameter values are selected according to a desired effect on SM properties. Optionally, after applying the treatment, SM properties are tested, for example, to measure the hysteresis curve of FIG. 6, or just to detect a difference in applied force as a function of strain, for example, at 2, 3 or more points of strain, to determine if the parameters yield a suitable effect (for example, effects as described herein). Optionally, the testing is done on a complete stent, or possibly only on a SM part of such a stent or other structure.

Exemplary Crimped Configuration

In some embodiments, in a structure crimped configuration, the structure is highly compressed and SM portion experiences a large (e.g., between 4 and 7%) strain, for example, a strain $\varepsilon_3$ corresponding with SM material behavior from unloading curve $f1"(A_s")$. For example, in some embodiments, a diameter of the crimped structure is less than a fifth of $D_{SM}$ or up to a tenth of $D_{SM}$ or less than a tenth of $D_{SM}$ Or intermediate fractions of $D_{SM}$.

Referring to FIG. 6, radially expanding forces of the crimped SM portion are low, F1" is lower than the force required to expand the polymer, F4. In some embodiments, F1" is approximately 50 MPa. This represents a stable crimped configuration.

FIG. 8A is a simplified schematic cross sectional view of a structure in a crimped configuration, according to some embodiments of the invention. The structure is optionally disposed within a lumen 800 (lumen includes lumen walls 808). In some embodiments, for example, for force balance, a radially expanding force F1" of a SM portion 804 is less than a force F4 needed to expand a second portion 806; F1"<F4. In the crimped configuration, force balance between the SM and polymer portion, for example, means that the stent stably remains in the crimped configuration, e.g. for accurate and safe deployment. Optionally or alternatively, the stent remains in stable configuration also during partial expansion thereof. Further, it is possible to selectively inflate/expand only a part of the device e.g., so as to engage the lumen, while other parts of the device are less, or not, deployed.

Exemplary Deployment

In some embodiments, to expand or deploy the stent from the crimped configuration, a force greater than or equal to, Fexpansion=F4-F1" is applied. For example, in some embodiments, expansion force is applied to the structure by a deployment device (e.g. by filling/inflating a balloon deployment device). In some embodiments, Fexpansion is low. A potential advantage of low Fexpansion is ease of deployment. It should be noted that the SM portion can help with the deployment the Polymer portion, so, overall, a lower deployment force is needed and/or lower stress polymer can be used (as after deployment it is supported by the SM portion.

In some embodiments, a structure is mounted directly on a balloon deployment device for direct stenting.

In some embodiments, a structure is expanded and/or deployed using a compliant balloon (e.g. using low pressure). A potential benefit of structure deployment using a complaint balloon is a highly conformed stent shape to lumen geometry.

In some embodiments, a structure is expanded and/or deployed using a non-compliant balloon (e.g. using high pressure). A potential benefit of structure deployment using a non-compliant balloon is that the stent can be used to open and/or enlarge a lumen (e.g. a body lumen), according to the balloon size. Optionally, some amount of recoil (e.g., 10%, 20%, 30% or intermediate values) is designed into the stent itself, by selecting a suitable match between SM and polymer hysteresis and applied forces and stent design. In other embodiments, recoil is substantially eliminated by such suitable selection.

FIG. 8B presents a plot of applied expansion force, Fexpansion, with strain, $\varepsilon$, for a composite structure, according to some embodiments of the invention.

In some embodiments, Fexpansion is higher between crimped ($\varepsilon=0$) and deployed configurations where F4>F1.

In some embodiments, Fexpansion is fairly constant between deployed diameters. In some embodiments, Fexpansion increases (e.g. slightly) between deployed diameters, for example, as the force required to expand the polymer portion, F4, increases with structure diameter. In some embodiments, Fexpansion goes up and down, but within a desired range (e.g., of low force values).

In some embodiments, Fexpansion rises above SM portion relaxed strain, where structure diameter=$D_{SM}$.

In some embodiments, the structure is unstable below D=$D_{SM}$, for example, when the SM portion diameter approaches $D_{SM}$, F1 reduces. Once F1<F5 the structure is unstable and collapses, under the polymer portion relaxation force, F5.

FIG. 8C is a chart showing the balancing between a force of expansion applied by a SM portion and a force of contraction applied by a second portion, in accordance with an exemplary embodiment of the invention. In an exemplary embodiment of the invention, various behaviors of force applied by the stent and/or forces resisted by the stent can be achieved by varying the stent (or other structure) parameters.

In FIG. 8C, magnitude indicates size of force and sign, its direction. In a schematic case, for a range of working diameters 820, it is desirable that a total applied force (828) by the stent is close to zero (822). When force 826 is positive, this means that the stent tends to expand on its own. As can be seen, any such tendency is much smaller than the tendency which would be provided if only the SM portion existed (force 824). This is due to the counteracting effect of force 826 applied by the second portion. In design, one may, for example, select a desired range for force 828 and/or a desired range of diameters 820, and proceed to design/select stent portions that have force graphs which when combined yield the desired result. In some cases, one or both of force graphs 824 and 826 is given and only other parts may be modified.

Referring specifically to force graph 824, the magnitude of the force can be modified, for example, using strain effect as described above, using more or less material and/or different strength of SM portion design. The range of diameters over which force is applied in a positive way can depend, for example, on the relaxed diameter selected for "memory". The shape of the line can depend on the actual geometry of the stent SM portion. For example, diamond-type designs apply different amounts of force at different states of deformation, due to the angle between the struts (when the deformation is at the angle). The shapes of such force charts are known for a wide range of shapes and one can choose a shape according to a desired shape of graph. In an exemplary embodiment of the invention, the graphs (designs) are selected according to an expected amount of strain, or vice versa—strain is selected in order to provide the desired shape of graph. Further, by providing a composite design (e.g., two sets of deforming shapes, each with different strength and/or memory), graph 824 can be an overlay of two such graphs and be, for example, non-monotonic. Such selections can also be made for the second portion. In general, if the design of the two portions is different, the shape of 826 and 824 will not be mirror images of each other.

Such selection can be, for example, manual. Alternatively, modeling software (e.g., numerical simulation, such as FEA and/or other numerical methods) can be used to select matching structures and/or parameters that meet a desired result.

Force 828 need not be monotonic. His may result in there being several "sweet spots", diameters that are easier to achieve by expansion.

It is also noted that force 828 may be non-zero (though generally as small as desired) or even somewhat negative. In an exemplary embodiment of the invention, the stent is stable in diameter due to one or more of the following considerations:

First, the forces shown are not pure forces and are generated in reaction to the forces applied to the parts of the stent. This means that the small amount of hysteresis, for example, in the second portion, may be enough to resist changes in diameter due to small apparent forces 828.

Second, the blood vessel (or other lumen) may be allowed to apply some resisting force. Generally, in many lumens some such force is desirable to assist in anchoring the stent in the lumen (e.g., by friction or embedding and/or to allow the stent to react to slow and/or fast changes in lumen diameter). For example, the force may be on the order of 30%, 20%, 10% or less or intermediate percentages of the force applied by the SM portion alone.

Third, the stent may include a third (or more) portion which exhibits plastic deformation, resistance to which deformation supplied the force which zeros force 826. Optionally, the stent is not formed of more than 5, optionally 4, 3 or 2 different materials and/or materials with different treatment.

FIG. 8C does not pertain to what happens to force 828 outside range 820. Depending on the properties selected for forces 824 and 826, this may cause expansion or self-crimping of stent at low radiuses and/or at high radiuses.

Exemplary Deployed Configuration

In some embodiments, structure deployed configurations include a range of diameters less than $D_{SM}$. In some embodiments, (for example, because the diameter is less than $D_{SM}$), in deployed configurations, the SM portion is under a low level of strain, for example, a strain $\varepsilon_2$. In some embodiments, deployed strains are 1-4%. In some embodiments, a range of deployed structure diameters is 5-12 mm.

Referring to FIG. 6, when the SM portion is under strain $\varepsilon_2$, unloading (expanding) of the SM portion follows curve $f_1'(A_s')$. Loading of the SM portion follows curve F2. Unloading or relaxing of the polymer portion follows curve F5 and loading or extension of the polymer portion follows F4.

In some embodiments, in deployed configurations, a force equilibrium or balance prevents the structure from collapsing, closing radially and/or crimping. FIG. 9A is a simplified schematic cross sectional view of a structure in a deployed configuration, according to some embodiments of the invention. In some embodiments, the balance is between the relaxation force F5 of the second portion 906, which is smaller than the loading force required to collapse or crimp the SM portion 904, F5<F2.

In some embodiments, in deployed configurations, a force equilibrium or balance prevents the structure from expanding. FIG. 10 is a simplified schematic cross sectional view of a structure in a deployed configuration, according to some embodiments of the invention. In some embodiments, the balance is between the radially expanding force of a SM 1004 portion F1', which is smaller than the force required to expand F4 a second portion 1006.

In some embodiments, in a deployed configuration, a structure exerts substantially zero outwards force on a lumen. F1'-F4~0. In some embodiments F4 is reactive to F1', so it comes exactly to same value as F1' (potentially it can be larger).

In some embodiments, there are a wide range of deployed configurations, (e.g. deployed diameters) corresponding with a wide range of stable or balanced strains $\varepsilon$ (shown on FIG. 6) where F1'<=F4 and F2>=F5.

Exemplary Crimp Resistance

In some embodiments, the structure, in a deployed configuration, is resistant to crimping and or closing. In some embodiments, for example, if the structure is circular in cross section, the structure has radial resistance to crimping. In other structures or sub-structures, such as a beam, crimp resistance is a resistance to bending and/or torsion.

Referring to FIG. 6, although forces required to radially compress or crimp the polymer portion is relatively low, F5, forces required to radially compress or crimp the SM portion are large, F2. Referring to FIG. 9A, a minimum force required to close or crimp the structure is Fcrimp=F2−F5.

In some embodiments, a force resisting radial collapsing, radial resistance, is substantially constant in structure deployed configurations (e.g., for example, selected using the methodology of FIG. 8C). In some embodiments, a force resisting radial collapsing increases with radial collapsing (decreases with strain), for example, because of decreasing F5 with strain.

FIG. 9B presents plots of crimp resistance, Fresist, with strain, $\varepsilon$, according to some embodiments of the invention. For example, if the structure is circular in cross section, $\varepsilon = \Delta D/D$, where $\Delta D$ is the change in diameter of the structure where D is the diameter of the structure in the crimped configuration.

Schematically illustrated in FIG. 9B are a radial resistance of steel 950, a radial resistance of structures and/or stents 952, according to some embodiments of the invention and an ideal radial resistance 954 (constant radial resistance for all diameters). In some embodiments, at $\varepsilon = 0$ and the structure is crimped, Fresist is at a maximum. As strain increases to deployed diameters, Fresist falls to a plateau, dropping after the plateau. In an exemplary embodiment of the invention, various parameters of the stent, for example, properties of the SM portion, properties of the second portion and/or a match between them, are selected to achieve a desired shape and/or length of the plateau and/or a desired small angle of inclination (and/or range of variance) thereof.

Exemplary Crush Resistance

In some embodiments, the structure has low resistance to a local pressure applied to the structure. FIG. 11 is a simplified schematic cross section of a structure in a deployed configuration, undergoing a local deformation, according to some embodiments of the invention. In an exemplary embodiment of the invention, a local deformation is one applied to less than 30%, 20%, 10% or other percentage, for example intermediate, as desired, of the diameter of the structure. In an exemplary embodiment of the invention, during crushing only the diameter changes and not the circumference of the structure. Possibly, this avoids a change in force applied by the polymer layer, while still affecting the force applied by the SM portion.

For example, in some embodiments, local pressure P1, applied to the structure corresponds with low strain on the SM portion. In some embodiments, a local pressure corresponds with low strain on the SM portion. In some embodiments, referring to FIG. 6, a local crushing pressure is approximately ⅓ of F2. In some embodiments, a local crushing pressure results in strains of approximately 0.1-1.5%, or less, for example, about 1% corresponding to classic elastic (austenite) SM portion reactive force (F2 before the plateau). In some embodiments, the reactive force (to the crushing force) of the polymer, F5, is almost zero, corresponding to a small strain of the polymer portion. Once local pressure P1 is removed, for example, as the polymer portion has not significantly changed in circumference, the SM portion returns to a pre-deformation deployed configuration.

In an exemplary embodiment of the invention, various parameters of the stent may be varied in order to achieve a desired crush resistance. For example, the SM portion design may be changed to make it to make it stiffer or use thicker SM material, giving a higher crush resistance. In such a case poly design may be changed to restore balance of forces.

Exemplary Second Portion, Additional Portions

In some embodiments, the second portion is a high recoil elastic (e.g. a high recoil polymer). In some embodiments, the second portion is extended such that it applies sufficient contracting force to balance the SM portion expanding force. In some embodiments, for example, in deployed configurations, the second portion is elastically extended from a relaxed diameter to, 100-600%, 200-500%, 300-400%.

In some embodiments, the second portion is elastic, including elastic hysteresis, as described above, where F4≠F5, for example, there being a difference of at least 10% 50%, 100%, 300% or intermediate percentages between F4 and F5. In some embodiments, the second portion is elastic, where F4=F5, for example, there being less than 10%, 5%, 3% or intermediate percentage of difference between F4 and F5.

In some embodiments, the second portion is shape memory as well, however, this may limit its range of expansion.

Optionally, in some embodiments, the second portion, and/or an additional portion is plastic, for example, plastically deformed during deployment e.g. gold. In embodiments where the second portion is plastically deformed during deployment, the second portion resists expansion of the SM portion.

In some embodiments, a structure includes more than two portions.

For example, in some embodiments, a structure includes three portions including a SM portion, a polymer portion with high recoil and an additional portion and/or layer, which is plastically deformed by deployment.

For example, the structure is deployed, plastically deforming an additional outer portion, upon a temperature change the SM portion and polymer portion self-crimp, for example, leaving the outer portion within the lumen.

For example, the structure is deployed, plastically deforming an additional portion disposed within said elastic second portion, the plastically deforming portion for example providing additional resistance to expansion (e.g. to increase control of expansion).

In an exemplary embodiment of the invention, the portions are arranged as layers, however, this need not be the case and depending on the mechanical coupling the two or more portions may be interleaved or provided side by side.

Exemplary Outward Radial Force (ORF)

In some embodiments, for example, as the radially expanding force of the SM material and the radially contracting force of the polymer are balanced, an outward radial force (ORF) of the structure outwards, when the structure is in a deployed configuration (e.g. a force outwards on the lumen from the deployed structure) is substantially zero (see also FIG. 8C).

FIG. 12 presents plots of outwards force from the structure, Forf, with strain c. For example, if the structure is circular in cross section, $\varepsilon = \Delta D/D$, where $\Delta D$ is the change in diameter of the structure and D is the diameter of the structure in the crimped configuration.

Schematically plotted in FIG. 12 are; a pushing force of stents of the art 1200, a pushing force of structures and/or stents 1202 according to some embodiments of the invention and an ideal pushing force 1204 (e.g. zero pushing force for all stent diameters).

In some embodiments, Forf is highest in the crimped configuration, where strain, $\varepsilon=0$. In some embodiments, as the structure is expanded (or independently expands), Forf decreases, until Forf=0 at a strain where D approaches $D_{SM}$. In some embodiments, Forf is minimal at $D=D_{SM}$, for example, due to selection of the polymer portion contracting force.

In some embodiments, Forf is about 0.1N when $\varepsilon=50\%$. This is in comparison with Forf=2-5N at $\varepsilon=50\%$ of self-expanding biliary or SFA stents of the art.

Exemplary Self-Crimping

In some embodiments, temperature related material characteristics of the SM portion are used to close or crimp the structure from a deployed configuration. Referring back to FIG. 5, in a deployed configuration the SM portion is superelastic, upon cooling below $A_s'$, for example, by spraying or washing the structure with cold saline solution, or otherwise cooling the structure directly or indirectly (e.g., cooling surrounding tissue and/or fluids) the SM material transforms to an easily deformable martensite crystal structure. At this point, the second portion can collapse the structure and meet little resistance.

FIG. 13 is a simplified schematic cross section of a structure in a deployed configuration, and forces on the structure upon a temperature change. In some embodiments, for example, at a low temperature (e.g. 10° C.), the radial resistance force of the SM portion, which is dependent on temperature, F2(T) is less than the relaxation force F5(T) of the polymer and the structure collapses.

In some embodiments, self-crimping is initiated without changing the temperature of the structure. In some embodiments, the structure is over-expanded (e.g. to above $D_{SM}$)

such that the SM portion provides a low or substantially no radially resisting force. The structure is no longer balanced, and the structure closes or collapses under the polymer relaxation force F5. The amount of over expansion may depend on the design. For example, 10%-20% may be sufficient for some designs, which for some normally-closed designs an increase of 500-700% may be needed. In an exemplary embodiment of the invention, the diameter at which self-crimping occurs is determined at design time and is, for example, between 110% and 600%, for example, between 130% and 200% of the maximum stable deployed diameter.

In some embodiments, a self-crimped structure diameter is larger than a minimal crimped structure diameter. This may be for example, as, in some embodiments, the stent is crimped at high strain by external crimper corresponding to low SM portion expanding force and correspondingly a low crimped diameter. Whereas, in some embodiments, for example, the polymer relaxation force responsible self-crimping is lower than forces applied by an external crimper, so SM portion strain is lower than externally crimped strain, SM portion expansion force is higher, resulting in a larger diameter.

Exemplary Self-Deployment

In some embodiments, temperature related material characteristics of the SM portion are used to open or deploy the structure, optionally without applying external force to the structure. In some embodiments, the structure is heated (e.g. using heated saline, microwave heating) and at least a part of the SM portion transforms from martensite to austenite crystal structure. In some embodiments, the austenite SM includes a higher radially expanding force than the polymer expansion force $F_4$ and the structure expands. In some embodiments, the structure, upon heating, self-expands or self-deploys to fill the lumen, in some embodiments, the structure expansion is stopped and/or limited by resistive forces of the lumen. In some embodiments, unlike self expanding stents of the art, as the structure cools (e.g. to body temperature) the outwards force of the structure on the lumen reduces as the SM portion transforms from austenite to superelastic behavior, until there is substantially no outwards force on the lumen, for example, as the SM radially expanding force is balanced by the polymer radially contracting force. In an exemplary embodiment of the invention, heating is provided in bursts so as to provide better control over expansion. For example, between 2 and 10, for example, between 3 and 5 bursts may be used to incrementally expand a structure.

Exemplary Two-Way Shape Memory

In some embodiments, a SM portion includes a two-way shape memory, for example of a type known in the art. As previously described, the first shape memory corresponds with $D_{SM}$. In some embodiments, a second shape memory is invoked upon cooling a crimped structure. In some embodiments, a structure crimps to a second shape memory structure diameter, the structure contracts on cooling to a second shape memory configuration. A potential benefit of two-way shape memory for self-crimping is a reduced structure crimped configuration size, for easy and safe insertion and/or removal of the structure.

FIG. 14A is a simplified schematic cross section of a structure in a crimped configuration, according to some embodiments of the invention.

FIG. 14B is a simplified schematic cross section of the structure of FIG. 14A where the SM portion has two way shape memory structure in a crimped configuration, according to some embodiments of the invention. The manufacture and construction of the SM portion and the second portion of the structures illustrated in FIG. 14A and FIG. 14B are optionally the same (e.g., material type, structure type, thickness and/or heat treatment). However, the SM portion illustrated in FIG. 14B has been set to have a second shape memory, of smaller diameter than the first shape memory. Upon cooling, the crimped structure diameter of the structure illustrated in 14B is smaller than a crimped structure diameter of the structure in FIG. 14A.

Exemplary Method of Use of the Structure

FIG. 15 is a flowchart of an exemplary method of use of a structure, according to some embodiment of the invention. Crimp structure onto positioning device.

At 1502, the crimped structure is delivered to desired location using a deployment device (e.g., a balloon catheter on which the structure is mounted, optionally by direct crimping thereon. Optionally, manufacturing comprises self-crimping the stent unto the balloon, for example, using one of the method described herein above.). At 1504, the structure is deployed (expanded), using deployment device. For example, in some embodiments, the deployment device manually expands the structure (e.g. by filling and/or inflating a balloon). Alternatively, or additionally, in some embodiments, the deployment device expands/deploys the device by initiating a temperature change (e.g. using heated/cooled saline).

Optionally, at 1506 the structure is collapsed or self-crimped, e.g. by a temperature change initiated by the deployment device. Optionally, at 1502, the structure is delivered to a desired location, e.g. repositioned before, at 1504, being re-deployed. Optionally, at 1508, the deployment device is removed.

Optionally, for example, after a time duration, at 1510 a deployment device is reintroduced, at 1512, the structure is collapsed or self-crimped, e.g. by a temperature change initiated by the deployment device and, at 1514 the structure is removed (e.g. on deployment device).

In an exemplary embodiment of the invention, during deployment, the structure is expanded and crimped multiple times, for example, expanded n a first location and based on an indication location is incorrect (anatomical image and/or functional effect), the stent is collapsed and repositioned. This may be especially useful for devices such as heart valves or aortic-arch stents or connecting stent grafts where exact positioning is often critical, yet not easy in a beating heart and/or at the end of a catheter. In an exemplary embodiment of the invention, the structure is expanded (and collapsed as needed in between) at least twice, for example, up to, for example, 3, 5, 10 or more or intermediate number times.

Exemplary Structures

Circumferential Segments

FIG. 16 is a simplified schematic side view of a crimped structure 1690, according to some embodiments of the invention. FIG. 17 is a simplified schematic side view of a deployed structure 1790, generally corresponding to structure 1690, according to some embodiments of the invention.

In some embodiments, stent 1690, 1790, includes more than one segment. In some embodiments, segments are circumferential segments 1612, 1712. In some embodiments, circumferential segments 1612, 1712 are coupled by axial connectors 1614, 1714. In other embodiments, segments may have other shapes, such as patches, axial sections and/or sections with both axial and partial circumferential extent and/or combinations of any of the above. Also as noted below, structures using the principles described herein can be non-tubular, for example, ring shaped, helical, beam shaped (e.g., straight or curved) and/or spherical or ellipsoid-like.

In FIG. 16, FIG. 17, FIG. 18, FIG. 19, FIG. 20, and FIG. 21 SM material is illustrated as black (inner layer, generally thinner) and polymer material, is illustrated as grey (outer layer, generally more robust). In some embodiments of the invention, the structures do not include both a SM layer and a second portion layer, for example utilizing materials and designs as known in the art, other than segmented design and connector design as described herein. It is noted, however, that there is a synergy between these designs and the use of a two portion stent with a SM portion and a second portion.

In some embodiments, a connector length compensates for a change in segment length (e.g. change in axial length of section 1612), for example, maintaining an overall structure length (e.g. upon expanding or contracting the structure). For example, if an axial length of segment 1612a reduces (e.g. upon deployment) in some embodiments, connectors 1614a extend such that an axial length 1613 remains the same. Optionally, this extension if "programmed" into the connector, as a shape memory. Optionally or alternatively, this modification is imposed by a balloon or other deployment structure restraining axial length changing of the device. Optionally, the deployment structure includes a plurality of elements, such as hooks or rings which engage structure 1690 and resist axial contracting and/or elongation thereof, during deployment.

Optionally, at least two segments each include a different enclosed geometry and/or area, optionally in a crimped and/or deployed configuration.

Optionally or alternatively, at least two different segments include and/or are formed of different materials and/or have different geometries and/or different axial lengths.

In some embodiments, one or more connectors 1614, 1714 include polymer only. In some embodiments, a potential advantage of polymer only connector/s, is a flexible connection between segments, for example, providing high stent flexibility (e.g. for deployment) and/or high conformability (e.g. to a lumen). A potential advantage of a stent with high conformability is a low movement of the deployed stent within the lumen (migration resistance) and a corresponding low re-stenosis rate.

In some embodiments, one or more connectors 1614, 1714 include SM material only. In some embodiments, one or more connectors include SM material and polymer.

In some embodiments, one or more segment includes a different design, for example, for providing different support in different stent areas. In some embodiments, one or more segment has a SM portion with a different relaxed diameter, $D_{SM}$. In some embodiments, one or more segment has a polymer portion with a different relaxed diameter, $D_{poly}$. In some embodiments, one or more segment has a different pattern or cell structure for the SM portion and/or the polymer portion. For example, one or more segment including SM portion with a zigzag structure and one or more segment including a flattened eight sided shape.

FIG. 18 is a simplified schematic cross section along a length of an exemplary structure 1890 in a crimped configuration, according to some embodiments of the invention. As can be seen, optionally the SM layer has less material and/or lower surface coverage (and/or different design) than the polymer layer. Optionally, the stenting (or other structural) function is provided by the polymer layer with the SM portion acting to provide structural stability as described herein. This may be applied also in non-segmented stents.

FIG. 19 is a simplified schematic cross section along a length of an exemplary structure 1990 in a deployed configuration, according to some embodiments of the invention.

FIG. 20 is a simplified schematic side view of an exemplary structure 2090 in a deployed configuration, on a deployment device 2002 (e.g., a balloon catheter), according to some embodiments of the invention.

In some embodiments, as illustrated in FIG. 16, FIG. 17, FIG. 18, FIG. 19 and FIG. 20 segments include a flattened eight sided shape, where the octagon flattens in the crimped configuration and expands in the deployed configuration. Other numbers of sides and/or geometries may be used as well, in other embodiments.

In some embodiments, deployment device 2002 includes one or more stopper elements (e.g. a distal and a proximal stopper, e.g., at the end of the stent or past the end of the stent, not shown), which optionally engage the stent and prevent axial movement thereof. Optionally, the stoppers are in the form of balloons. Optionally or alternatively, one or both of the stoppers are in the form of rings which abut the stent and/or in the form of a protruding element which engages the stent, e.g., between struts thereof/in an aperture thereof. In some embodiments, deployment device 2002 includes a catheter. In some embodiments, mounting is by placing the stent on the balloon, between the stoppers and cooling to evoke self-crimping, such that upon a temperature change the structure self-crimps over the catheter between the stoppers. In some embodiments, one or more stopper prevents the stent from sliding (e.g. off) the deployment device (e.g. upon removal of the device from the body (and/or insertion thereinto).

In some embodiments, a distal stopper (e.g. on the free end of the retrieving catheter) is a small low pressure balloon. In some embodiments the distal stopper balloon is deflated when the deployment device is inserted into a deployed stent and is inflated, for example, before pulling the deployment device out of the body (e.g. either before or after crimping).

In some embodiments, deployment device 2002 includes one or more side holes through which a liquid (e.g. saline), in some embodiments, is flushed e.g. to initiate a structure temperature change. In some embodiments, the side holes are situated between stoppers. In some embodiments, such flushing is provided within the balloon (e.g., cooling or heating its contents, e.g., using an internal or external (to body) heater). Optionally or alternatively, flushing is provided from a port (e.g., an overtube such a guide catheter) proximal to the stent.

In some embodiments, segments include a SM portion with folding zigzag structure. In some embodiments, closing of a stent is by bending at apexes of the zigzags. FIG. 21 is a photographic side view of a second exemplary structure 2190 in a crimped configuration, on a deployment device 2102, according to some embodiments of the invention. FIG. 22 is a photographic side view of the second exemplary structure 2290 in a deployed configuration, on a deployment device 2202, according to some embodiments of the invention. The embodiment illustrated in FIG. 21 and FIG. 22 includes a transparent polymer portion (not visible in the figures) which substantially covers (e.g. is cylindrical in shape) the SM portion, e.g. covering more than 80%, more than 90%, more than 95% or intermediate percentages of the SM portion. In some embodiments, a covering polymer portion includes small apertures.

In some embodiments, a structure includes more than one SM portion and a single second portion restraining and interconnecting the SM portions. FIG. 38A is a simplified schematic front view of a crimped stent, according to some embodiments of the invention. FIG. 38B is a simplified schematic axial cross section of a crimped stent, according to some embodiments of the invention. FIG. 38C is a simplified schematic front view of a deployed stent, according to some embodiments of the invention. FIG. 38D is a simplified schematic axial cross section of a deployed stent, according to some embodiments of the invention.

In some embodiments, parts of the second portion (e.g. connectors or a connecting sleeve) are not supported by a SM segment. In some embodiments unsupported second portion parts protrude into a structure lumen 3899. A potential benefit of unsupported second portion parts is reduction and/or elimination of SM segment axial movement within the structure lumen (e.g. by physically blocking movement). It should be noted that such axial migration prevent is possible even if there is only a single SM portion and a single polymer portion (e.g., design of FIG. 38A), by the polymer portion radially contracting where it does not overlap the SM portion (e.g., at edges thereof and/or overlaying apertures therein) such that interference is created between said SM portion and said polymer portion. Optionally, the polymer portion extends a few mm or fractions thereof past the edge of said SM portion.

In some embodiments, the second portion includes axial struts, correspondingly, for example, in some embodiments, the protrusion of the second portion into structure lumen 3899 is hexagon-like in shape as illustrated in FIG. 38C. FIG. 38E is a photographic illustration of a top view of a exemplary structure with a second portion protruding into a structure lumen, according to some embodiments of the invention.

Construction of the Structure

In some embodiments, the SM portion and/or the polymer portion are solid tubes with an internal structure lumen. In some embodiments, the SM portion and/or the polymer portion are formed of struts and/or are lattice-like and/or are mesh-like. In some embodiments, the SM portion and/or the polymer portion are tubular and are formed of struts/lattice/mesh. In some embodiments, a percentage of the tube surface which is delineated by a part of the structure, herein termed surface coverage, is between 10%-95%, or over 95%, or less than 10% or intermediate values, such as 20%, 40%, 60% or intermediate values. In embodiments with non-tubular structures, surface coverage relates to structure surface porosity and is, for example, between 10%-95%, or over 95%, or less than 10% or intermediate values, such as 20%, 40%, 60% or intermediate values. In an exemplary embodiment of the invention, the SM portion and second portion have different coverage percentages, for example, being different by a factor of 1.5, 2, 3, 4 or intermediate or greater factors (e.g., more second portion than SM portion coverage or vice versa).

FIG. 41 is a simplified schematic cross sectional view of a structure, according to some embodiments of the invention. FIG. 42 is a simplified schematic cross sectional view of a structure, according to some embodiments of the invention. FIG. 41 and FIG. 42 illustrate a feature of some embodiments, that, at any particular cross section, a portion of a tube surface 4170, 4270 is inhabited by a SM portion 4104, 4204 and a second portion 4106, 4206. In other embodiments, some parts of the cross-section have only one of the SM portion and second portion (this can be seen in FIG. 19, for example). Furthermore, in some embodiments, while each (or many) cross-sections include both SM material and other (second) material, they need not be located at the same circumferential position. For example, in FIG. 20, SM material is generally arranged at angles and second portion material is generally arranged parallel to the axis of the stent, so at most locations, two struts (of different layers) will meet at an angle and not overlap for much of their lengths. FIG. 41 shows an example where the second portion surrounds the first portion. FIG. 42 shows an example where each SM portion is sandwiched between two second portion-materials. This may be the result, for example, of embedding the SM portion in the second portion, or the result of use of multiple layers, possibly with different relaxed diameters and/or material properties. In other embodiments, the SM portion (e.g., at least 51% thereof) is surrounded on at least four cardinal sides by the second portion.

In some embodiments, the SM portion and/or the polymer portion are constructed and/or manufactured by cutting out portions of a solid tube. For example, in some embodiments, the structures of FIGS. 19-23 are constructed by cutting (e.g. laser cutting) out portions of the tubes.

In some embodiments, the structure is constructed by bending one or more wire or tape. FIG. 23 is a photographic side view of a third exemplary structure 2390 in a crimped configuration, according to some embodiments of the invention. FIG. 24 is a photographic side view of a third exemplary structure in a deployed configuration 2490, according to some embodiments of the invention. For example, in some embodiments, the structure illustrated in FIG. 23 and FIG. 24 is optionally constructed by bending and connecting (e.g. by welding) of wires and/or by laser of plasma or other cutting of a tube.

In some embodiments, a structure is constructed by braiding or weaving. FIG. 25 is a simplified schematic side view of an exemplary braided structure 2590, according to some embodiments of the invention. SM material portions 2504 are illustrated using solid lines, second portions 2506 (e.g. are illustrated using dashed lines.

In some embodiments, a structure (or part thereof) is constructed by winding a tape or wire into a desired shape, e.g. a coil. FIG. 26 is a simplified schematic side view of an exemplary coil structure 2690, according to some embodiments of the invention. Optionally, the coil is formed of a SM material covered by or adhered to or otherwise connected to a polymer or other "second" layer.

Coupling of Portions

In some embodiments, the SM portion is coupled to the polymer portion by tension (e.g., in combination with friction and/or interference using deformation caused by tension). For example, in some embodiments, a SM portion is compressed and/or a polymer portion is expanded and the SM portion is placed within the polymer portion, expanding and contracting forces holding the two portions together.

In some embodiments, the SM portion is coated in polymer (e.g. the SM portion is imbedded in polymer). FIG. 27 is a simplified schematic cross section of a structure with more than two portions, according to some embodiments of the invention. In some embodiments, the structure illustrated in FIG. 27 is constructed by coating a SM portion 2704 (e.g. dip coating), for example, with polymer 2706.

In some embodiments, a structure includes a non-circular cross section, optionally in a crimped and/or a deployed configuration, for example, one or more angles (possibly rounded, possibly with a sharp edge, but with a radius of curvature of less than ¼ of that of the device as a whole) and/or a non-symmetrical cross section. FIG. 28 is a simplified schematic cross section of a structure 2890, according to some embodiments of the invention, showing such sharp bends.

In some embodiments, expansion of the structure is non-radial. For example, the structure illustrated in FIG. 29, in some embodiments, expands substantially more in an x-direction (e.g. by a factor of 1.5, 2, 3, or more, and possible does not expand in a y-direction).

Exemplary Normally Relaxed SM Portion

In some embodiments, the SM portion is relaxed in the crimped configuration and does not exert an expanding force on the polymer portion in the crimped configuration.

In some embodiments, the SM portion is in the austenitic state in the crimped configuration ("normally closed"). Upon, for example, balloon deployment, the SM portion transforms into martensite, due to applied strain, with A'f deployed>Tbody>Af crimped and remains in this state at body temperature, so that SM portion remains in the deployed configuration.

In some embodiments, raising a temperature of the stent causes the SM portion to transform from martensite into austenite phase, and SM portion radial resistance force is less than polymer relaxation force, so the SM portion returns to its crimped austenite shape and the stent collapses, possibly returning to the initial crimped or closed configuration.

In some embodiments, a structure normally closed SM portion is treated to generate a two way shape memory effect (TWSME). In some embodiments, a second shape memory is set for a SM portion diameter larger than the SM portion crimped (e.g. first shape memory) diameter. In some embodiments, the second shape memory leads to additional expansion of SM portion. A potential benefit of a SM portion with a second shape memory is a reduced elastic recoil in the direction of decreasing stent diameter.

Exemplary Low Foreshortening Structure

In some embodiments, the structure has low foreshortening when transferring between a crimped to a deployed configuration: Referring back to FIG. 1A and FIG. 1B, a length, Lcrimp of the structure in a crimped configuration (illustrated in FIG. 1A) is substantially the same as a length Ldply of the structure in a deployed configuration (illustrated in FIG. 1B). In some embodiments, (Lcrimp−Ldply)/Lcrimp is less than 2%, less than 1%, less than 0.5%. A potential advantage of low foreshortening is the ability to accurately control a position of a deployed stent by positioning of the crimped stent. As noted above, such structures may also be used for stents without strain induced behavior (e.g., not meeting FIG. 6).

Referring back to FIG. 24, which shows a structure with low foreshortening in a deployed configuration. In some embodiments, the structure 2490 includes one or more rigid struts orientated axially 2416. In some embodiments, radial expansion of the structure is through unbending and/or stretching of flexible, weaker and/or joint sections 2418. In some embodiments, struts 2416 are not substantially deformed by radial expansion and/or crimping and maintain a substantially constant length. In some embodiments, constant length of rigid struts 2416 substantially maintains the structure length in the crimped and deployed configurations.

In some embodiments, flexible sections 2418 and rigid struts 2416 are connected to each at connection points 2417. In some embodiments, a distance between connection points does not change during crimping and/or expanding/deployment of the structure. In an exemplary embodiment of the invention, it is noted that when deploying a stent axial shortening can occur due to differences in diameter between different segments and/or due to axial bending. In an exemplary embodiment of the invention, flexible interconnections 2414 are provided, for example, in the form of diamonds, but alternatively in the form of curved sections, which can deform to accommodate such differences in radius.

FIG. 31 is a simplified schematic of a section of a structure 3192 including low foreshortening, according to some embodiments of the invention. FIG. 32 is a simplified schematic of a section 3292 of a structure with low foreshortening, according to some embodiments of the invention. In some embodiments, segments 3112, 3212 include rigid struts orientated axially 3116, 3216. In some embodiments, curved connectors (e.g. sinusoid) 3114 run along the structure axially. In some embodiments curved connectors (e.g. sinusoid) 3214 are staggered axially along the structure. FIG. 32 shows a design with possibly more flexibility than the design of FIG. 31, as the connectors are in adjacent rows rather than same rows as in FIG. 31.

Exemplary Kink Resistance

In some embodiments, the structure bends without significantly (e.g., 20%, 30%, 40% or more) reducing a structure cross sectional area at the bending point and/or the structure bends without closing the structure at a bend and/or substantially decreasing a structure cross sectional area at the bend.

In some embodiments, the structure includes deformable connectors where each connector is able to independently extend and/or retract in length. In an exemplary embodiment of the invention, such connectors extend at one side of the bend (and possibly due to flexibility thereof follow the curve) and contract (rather than bend inwards) at the inside of the bend. As noted above, such structures may also be used for stents without strain induced behavior (e.g., not meeting FIG. 6).

FIG. 33 is a simplified schematic of a contracted connector 3314, according to some embodiments of the invention. FIG. 34 is a simplified schematic of an extended connector 3414, according to some embodiments of the invention. In the example shows, the structure is two vertex-to-vertex connected diamonds or parallelogram elements. However, smaller or greater number of elements could be provided. Optionally or alternatively, the elements may be rounded (e.g., ovoid).

FIG. 35 is a photographic side view of a third exemplary structure which has been bent, according to some embodiments of the invention. For example, in some embodiments, when the structure is bent one, or more connector 3514b will extend in length (e.g. those connectors on the outside of the bend) and/or one or more connector with contract in length 3514a (e.g. those connectors on the inside of the bend).

In some embodiments, connectors include rhombic shapes. FIG. 36 is a simplified schematic of a section of a structure including kink resistance, according to some embodiment of the invention. In some embodiments, segments 3612 are rhombic in shape. Connectors 3614 include two rhombic shapes.

FIG. 37 is a simplified schematic of a section of a structure including kink resistance, according to some embodiments of the invention. Connectors 3114, including two rhombic shapes, connect segments 3712. In some embodiments, structures with rhombic connectors have closed cell structure. FIGS. 36 and 37 illustrate rhombic connectors for closed cell stent structures, wherein FIG. 26 an example of the connectors being adjacent (and not part of) radially resisting sub-structures is shown and in FIG. 37 the connectors may be part of a radially resisting sub-structure.

In an exemplary embodiment of the invention, the connectors are small relative to the segments, for example, in the crimped state, having a length of less than 50%, 30%, 10% or intermediate percentages of a neighboring segment. As noted above, segments need not be perfect cylindrical segments and may have other shapes as well, including ribbon shape and angled cylinder shaped (cylinder, where end faces are not perpendicular to cylinder angle).

In some embodiments, connectors prevent forces being transferred between segments. In some embodiments, an axial force (e.g. force tending to cause structure migration within the lumen) is at least partially absorbed by compression of connectors, for example, preventing and/or reducing stent migration.

In an exemplary embodiment of the invention, the connectors are weaker than the segments, for example, by a factor of at least 2, 3, 4 or more. However, as all or most deployment forces are radial, the connectors do not need to resist (during or after deployment) large forces.

A potential benefit of contractible and/or extendible connectors, which is also a potential advantage of polymer only connector/s, is a flexible connection between segments, for example, providing high stent flexibility (e.g. for deployment) and/or high conformability (e.g. to a lumen). A potential advantage of a stent with high conformability is a low movement of the deployed stent within the lumen (e.g., migration resistance).

Exemplary Non-Tubular Structures

In some embodiments, the structure is tubular in a crimped configuration and is expanded to a sphere-like (or other substantially closed) shape in a deployed configuration. In some embodiments, a SM portion shape memory is set to be a sphere-like shape. In some embodiments, a SM portion shape memory is set to be a body lumen shape or a part of body lumen shape, e.g. bladder, portion of the heart.

In some embodiments, the structure has in crimped configuration small diameter cylindrical shape and, in a deployed configuration has a sphere-like shape, with elliptical distortion. In some embodiments, the deployed configuration is provided due to deployment on high compliance balloon and comply with body duct. In some embodiments, a SM portion has normally closed shape in austenite state and the SM portion transforms into strain induced martensite upon balloon deployment. In some embodiments, the structure is removed by self-crimping. In some embodiments, self crimping is when the structure is heated to above Af'>body temperature>Af.

In some embodiments a self-expanding upon heating embodiment is used, so there is no need to provide a balloon inside the structure being deployed, however, slow deployment can be provided (e.g., using spurs of heated fluid with fluoroscopy for feedback).

Additional structures may be provided in accordance with some embodiments of the invention. For example, a beam, having a layer of SM material and a second layer of "second portion" material, may be deployed (e.g., by bending) as described herein, and once deployed, will resist cursing and crimping and can possibly self undeploy. This may be useful for hooks as well, whereby cooling may be used to straighten the hooks, while the two layer design being used to provide sufficient strength prior thereto. Optionally or alternatively, to a hook, a curved beam may be provided.

In such embodiments, such a beam can optionally be balanced at multiple deformation (e.g., "expansion") positions.

Another example of a structure is a ring or other curved or arcuate shape, optionally nearly or completely closed, which can be formed of two rings, each one of a different material.

Another example of a structure is a joint (e.g., a living hinge or a location of weaker material where stiffer struts meet). such a joint can be locked into multiple positions and resist small amounts of deformation, with significant resilience.

As can be appreciated, such components (cylinder, sphere, beams, joints, etc.) and/or other components can be combined to provide arbitrary composite structures.

For brevity of description, most of the specification refers specifically to tubular shapes, however, the mechanisms, structure and treatments described herein should be understood to refer to other structures as well, such as beams.

Exemplary Additional Technologies

The designs described herein are generally compatible with many stent technologies.

In some embodiments, a structure includes one or more radiopaque marker, for example to assist in structure placement in a body lumen. Such a marker may be, for example, welded to the SM section and/or embedded in a polymer section.

In some embodiments, drug eluting is provided. In some embodiments, the polymer portion includes one or more drug eluting part. In some embodiments, the SM portion includes one or more drug eluting part. Optionally or alternatively, drug storage is in a layer or reservoirs between the two portions, or is provided in a third portion and/or as a coating layer.

In an exemplary embodiment of the invention, additional physiologically function layers, such s mesh for encouraging endothelial growth or a graft layer, are provided.

Various embodiments and aspects of the present invention as delineated hereinabove and as claimed in the claims section below find experimental support in the following real and/or hypothetical examples.

EXAMPLES

Reference is now made to the following examples, which together with the above descriptions illustrate some embodiments of the invention in a non limiting fashion. While the examples show particular parameters and combinations, these are not to be understand as being required to be practiced together or essential, if they are not. Rather, various features shown in the examples can be combined with features shown in other examples or in the above description, within the scope of some embodiments of the invention.

Example 1

Composite Stent Manufacturing and Testing, General Properties

Manufacture

A SM portion was laser cut from a nitinol tube. The nitinol tube was then placed onto a mandrel to set a 13 mm shape memory diameter and heat treated. Heat treatment was 520° C. for 20 min, then 600° C. for 40 min and then 400° C. for 1 hour. It is noted that other heat treatments could have been applied. Austenite transformation finish temperature, Af, was measured at two nitinol portion diameters, at a diameter of D=8 mm, Af was 20° C., after crimping the nitinol to D=2.2 mm, Af was 33° C.

A polymer portion was laser cut from Polyurethane Tecothane 1074 grade tube with a diameter of 2.5 mm and wall thickness of 0.3 mm.

A composite stent was assembled by crimping and inserting the nitinol portion into the polymer portion.

Testing

The composite stent was placed onto a balloon delivery system and crimped to 4 mm diameter. The stent was then balloon deployed to a diameter of 8.2 mm, which was stable at 37° C. The stent was then self-crimped by cooling the composite stent with saline at 10° C. and the resulting diameter of the stent after self-crimping was 5.5 mm. It should be appreciated that depending on the design and embodiment of the invention, self crimping can be, for example, to a diameter of 200%, 150%, 100%, 80%, 50% or intermediate or smaller or larger percentages of the originally crimped diameter.

Example 2

Composite Stent Testing (Radial Conformability, Outward Force)

Manufacture

Two nitinol portions were manufactured according to Example 1. One polymer portion was manufactured according to Example 1. A composite stent was manufactured by crimping the two nitinol portions and inserting them into the polymer portion where each nitinol portion was restrained by the polymer portion and the polymer portion formed a connector between the two nitinol portions (e.g., similar to the FIG. 16 and/or FIGS. 38B and 38D).

Testing

The composite stent was inserted into a simulated lumen. The simulated lumen was a tube with two different diameters, a portion with 8 mm diameter and a portion with 5 mm diameter. The composite stent was balloon deployed in the simulated lumen, with one segment of the stent in each portion of the simulated lumen.

After deployment the stent had two different diameters, the stent segment deployed in the 8 mm lumen portion was measured to be 7.8 mm diameter and the segment deployed in the 5 mm lumen portion was measured to be 4.9 mm diameter. Stability of the deployed stent was tested by removing the stent from the simulated lumen. Upon removal of the simulated lumen the stent maintained the deployed stent shape. Lack of expansion of the stent, upon removing the stent from the stimulated lumen (which could have been providing a reactive force to an outwards force) illustrated that there was substantially no outwards force from the deployed stent.

Example 3

Crush Resistance

Manufacture

A composite stent according to Example 2 was deployed into a simulated lumen which was a PE tube with a 0.05 mm wall and a diameter of D=8 mm. A stent of the art (Propel, absorbable polymer stent made by Intersect ENT) was deployed into a similar PE tube of 10 mm diameter.

Testing

Both stents were tested for crush resistance using a Testometric universal testing machine. Testing was conducted at 25° C., in some embodiments, a worst case temperature for the inventive device as, in some embodiments, maximal crush resistance is at body temperature (e.g. 37° C.). The testing machine gauge length was set up to 10 mm.

FIG. 39 presents a plot of measured crush resistance with deflection, for an exemplary embodiment of the invention. A measured crush resistance force for the composite stent at a maximal crushing of about half (about 4 mm) of the deployed stent diameter (corresponding to a 'deflection' of about 6 mm from 10 mm as the first 2 mm of the gauge length has zero force before contact was made with the 8 mm diameter stent) gauge length (real 4 mm=half of deployed diameter) is 90 gf.

FIG. 40 presents a plot of measured crush resistance with deflection, for a stent of the art (Propel sinus stent). A measured crush resistance force for the Propel stent was only 20 gf corresponding to a crushing of 6 mm (approximately 60%).

As can be seen crush resistance for a considerable range of diameters can be substantially better than for standard stents.

Example 4

Kink Resistance

Manufacture

A nitinol portion was manufactured according to Example 1. The nitinol structure included rhomb connectors (similar to that illustrated in FIG. 24) connecting two stent segments.

A polymer portion was laser cut from Polyurethane Tecoflex EG85 grade tube with a diameter of 2.5 mm and wall thickness of 0.3 mm.

Testing

The deployed stent was bent at an angle of more than 45° between two segments. Bending did not result in a change in stent segment geometry. Bending did not result in stent kinking (the struts did not substantially protrude into the cross sectional internal area of the stent).

Example 5

Normally Closed Stent

Manufacture of SM Portion

A SM portion was laser cut from a nitinol tube. The nitinol tube was then placed onto a mandrel to set a 2.5 mm diameter and heat treated. Heat treatment was 520° C. for 20 min, then 600° C. for 40 min and then 400° C. for 1 hour. Austenite transformation finish temperature, Af, was measured at two nitinol portion diameters, at a diameter of D=8 mm, Af was 20° C., after crimping the nitinol to D=2.2 mm, Af was 33° C.

Testing of SM Portion

Expansion of the SM portion on a balloon delivery system to 6 mm diameter resulted in an Af of 20° C., (the stent was fully closed at 20° C.). SM portion expansion on a balloon delivery system to 14 mm diameter resulted in an Af of 44° C. and an As of 40° C., so that, after expansion, the SM portion kept the expanded diameter at 37° C.

Manufacture of Polymer Portion

A polymer portion was manufactured from a tube of silicone elastomer grade 40 with 2.3 mm diameter and a wall thickness of 0.15 mm.

Manufacture of Composite Stent

A composite stent was assembled by crimping and inserting the nitinol portion into the polymer portion.

Testing of Composite Stent

The composite stent was placed onto a balloon delivery system and crimped. The stent was then balloon deployed to a diameter of 14 mm, which, upon balloon deflation reduced to a stable 11.3 mm at 37° C. Heating the composite stent to 45° C. lead to self-crimping of the stent to a diameter of 3.5 mm.

Example 6

Two Way Shape Memory

Manufacture

A SM portion was manufactured according to Example 1. The nitinol portion was then placed onto a mandrel and subjected to training to set a second shape memory diameter of 10 mm.

A polymer portion was manufactured according to Example 1.

A composite stent was assembled by crimping and inserting the nitinol portion into the polymer portion.

Testing

Features were similar to Example 1, but self-crimped diameter was 4.9 mm, 10% less, compared with Example 1.

Example 7

Normally Closed, Two Way Shape Memory

Manufacture

A SM portion was manufactured according to Example 5. The nitinol portion was then trained to TWSME, in order to set a second shape memory diameter of 3.5 mm (more than 2.5 mm).

A polymer portion was manufactured according to Example 5.

A composite stent was assembled by crimping and inserting the nitinol portion into the polymer portion.

Testing

The stent was then balloon deployed to a diameter of 14 mm, which, upon balloon deflation reduced to a stable 12.4 mm at 37°, two way shape memory training led to about a 10% increase in deployed diameter.

General

As used herein the term "about" refers to ±20%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An expandable structure comprising:
  a first shape memory (SM) portion which consists of nitinol, where said first SM portion is loaded, from a relaxed configuration, by compressive strain, which applies a SM portion expanding force during unloading by expansion; and
  a second portion mechanically coupled to said first SM portion so that said second portion resists expansion of said first SM portion with a contracting force, over a plurality of different expansion states of said first SM portion;

wherein said first SM portion is pre-treated to have a decrease in said SM portion expanding force as a function of a maximum value of compressive strain applied to said first SM portion, where said SM portion expanding force decreases with an increase of said maximum value of compressive strain.

2. The expandable structure according to claim 1, wherein said first SM portion is pre-treated to display a strain induced martensite behavior which is characterized by said SM portion expanding force decreasing as a function of strain of said first SM portion, so as to have a difference selected from at least 10% and at least 20% in force between two strain states at which said structure is usable.

3. The expandable structure according to claim 1, wherein said second portion both resists expansion of said first SM portion and said first SM portion resists contraction of said second portion, due to said decrease in said SM portion expanding force as a function of a maximum value of compressive strain applied to said first SM portion at different deployment stages thereof.

4. The expandable structure according to claim 1, wherein said structure is configured to exert less outward force than 30% of said SM portion expanding force, at a deployed stable configuration.

5. The expandable structure according to claim 1, wherein said pre-treatment consists of a treatment selected from heat treatment, memorizing treatment, solution treatment, aging treatment and combinations thereof.

6. The expandable structure according to claim 1, wherein said first SM portion is treated such that, in a crimped state, an austenite transformation finish temperature of at least 10% thereof is at least 5° C. above an austenite transformation finish temperature in a deployed state, at a temperature range between room temperature and body temperature of 18° C.-39° C.

7. The expandable structure according to claim 1, wherein said first SM portion and second portion are selected so that said structure has a resistance to a crimping force acting to radially crimp the structure equal to one of at least 40% of a self-expansion force of said first SM portion and at least 100% of a force required to expand the structure.

8. The expandable structure according to claim 1, wherein said first SM portion and said second portion are selected so that said structure elastically deforms upon application of a low strain which changes a circumference of said structure by less than 5%.

9. The expandable structure according to claim 1, wherein said first SM portion and said second portion are selected so that said structure exhibits a crush resistance greater by a factor of at least 10 of an outwardly applied radial force applied by said structure.

10. The expandable structure according to claim 1, wherein said first SM portion has a relaxed diameter of more than 100% of a relaxed diameter of said second portion.

11. A tubular expandable structure, said structure being in the form of a plurality of segments, each segment comprising:
at least one first SM portion of claim 1; and
a second portion of claim 1 restraining said at least one first SM portion; and
a plurality of connectors, each connector axially coupling two segments;
wherein a diameter of at least one of said segments in a deployed state is radially expandable and at least one of said connectors is more axially compressible than said segments.

12. The expandable structure according to claim 11, wherein at least one section of said second portion is configured to radially contract at least one location where not overlapping with said at least one first SM portion and at least assist in preventing axial motion of said at least one first SM portion relative to said second portion.

13. The expandable structure according to claim 11, comprising a single SM tubular portion which includes said first SM portion of each said segment, and said plurality of connectors, formed as said single SM tubular portion.

14. The expandable structure according to claim 11, wherein one or more of said plurality of segments is deployed to have a different deployed diameter than another of said plurality of segments.

15. The expandable structure according to claim 11, wherein, for each of said plurality of segments, each said first SM portion has a shape memory diameter and cross-sectional shape, and wherein at least one first SM portion of at least one segment of said plurality of segments, has at least one of a different shape memory diameter and a different cross-sectional shape than that of another of said first SM portions.

16. The expandable structure according to claim 11, wherein each said first SM portions, of said plurality of segments, is heat treated and wherein at least one first SM portion in one segment has a different heat treatment from the heat treatment of another of said first SM portions in another segment.

17. The expandable structure according to claim 11, wherein each said segment has a segment axial length and at least one segment has a different axial length from that of another segment.

18. An expandable structure according to claim 1 comprising:
at least one of said first SM portion and said second portion including a plurality of circumferential segments;
at least one of said first SM portion and said second portion including a plurality of flexible connectors configured to bend axially, each connector axially coupling two segments; and
at least one of said first SM portion and said second portion including a plurality of rigid struts orientated axially along the structure and each having an initial length, wherein each rigid strut is coupled to another two rigid struts by at least two flexible connectors such that said rigid struts coupled by flexible connectors form at least one circumferential segment of a tubular structure;
wherein upon a radial expanding force said flexible connectors unbend to expand a diameter of each said circumferential segment;
wherein upon a radial contracting force said flexible members bend to contract a diameter of each said circumferential segment; and
wherein said rigid struts substantially maintain said initial lengths thereof; and wherein said flexible connectors are more axially compressible than said segments.

19. The expandable structure of claim 18, wherein said plurality of flexible connectors comprise at least one rhombic shape.

20. A method of use of an expandable structure comprising:
(a) providing an expandable structure according to claim 1;
and one of:
(b) expanding said structure and cooling said expanded structure, wherein said cooling is such that a SM resisting force is less than the second portion contracting force and allowing said structure to collapse due to said second portion contracting force;
(c) expanding said structure such that a SM portion resisting force is reduced to below said second portion contracting force and allowing said structure to collapse under said second portion contracting force; and
(d) expanding said structure and cooling said expanded structure, wherein said cooling is such that said first SM portion is urged to return to a second shape memory diameter.

21. The method of claim 20, wherein said cooling is such that the SM resisting force is less than the second portion retracting force, and wherein said cooling is below a SM portion transformation temperature.

22. A system comprising the expandable structure according to claim 1, a deployment device, and at least one drug eluting part.

23. The system according to claim 22, wherein said deployment device comprises a balloon.

24. The system according to claim 22, wherein said first SM portion includes said at least one drug eluting part.

25. The system according to claim 22, wherein said second portion includes said at least one drug eluting part.

26. The system according to claim 22, wherein said at least one drug eluting part is provided between said first SM portion and said second portion.

27. A system comprising, a deployment device, and:
an expandable structure comprising a plurality of tubular segments, each segment comprising:
at least one first SM portion of claim 1;
a second portion, of claim 1, restraining said at least one SM portion; and
a plurality of connectors, each connector axially coupling two segments; and
wherein at least one of said connectors includes at least one drug eluting part.

28. A system comprising the expandable structure according to claim 1, said system further comprising a deployment device;
wherein said expandable structure includes at least one drug eluting coating.

29. A system comprising the expandable structure according to claim 1, a deployment device, and at least one drug eluting layer.

30. The expandable structure according to claim 1, wherein said first SM portion is treated such that, in a crimped state, an austenite transformation finish temperature of at least 10% thereof is at least one of 10° C., and at least 15° C. above an austenite transformation finish temperature in a deployed state.

31. The expandable structure according to claim 1, wherein said expandable structure is configured to be expanded from a crimped configuration to a deployed configuration, where said first SM portion is in an expansion state, at least twice.

32. The expandable structure according to claim 31, wherein said deployed configuration includes a range of sizes, corresponding to said plurality of different expansion states of said first SM portion, wherein a size of said deployed configurations is 1.5 to 3 times a size of said crimped configuration.

33. The expandable structure according to claim 1, wherein said first SM portion is superelastic in a deployed state at body temperature of 37° C.

34. An expandable structure comprising: a first shape memory (SM) portion loaded, from a relaxed configuration, by compressive strain, which applies a SM portion expanding force during unloading by expansion; and a second portion mechanically coupled to said first SM portion so that it resists expansion of said first SM portion with a contracting force, over a plurality of different expansion states of said first SM portion; wherein said first SM portion is pre-treated to have a decrease in said SM portion expanding force as a function of a maximum value of compressive strain applied to said first SM portion, where said first SM portion expanding force decreases with an increase of said maximum value of compressive strain; and wherein said first SM portion is treated such that, in a crimped state, an austenite transformation finish temperature of at least 10% thereof is at least one of 10° C., and at least 15° C. above an austenite transformation finish temperature in a deployed state.

35. An expandable structure comprising:
a first shape memory (SM) portion loaded, from a relaxed configuration, by compressive strain, which applies a SM portion expanding force during unloading by expansion; and
a second portion mechanically coupled to said first SM portion so that it resists expansion of said first SM portion with a contracting force, over a plurality of different expansion states of said first SM portion;
wherein said first SM portion is pre-treated to have a decrease in said SM portion expanding force as a function of a maximum value of compressive strain applied to said first SM portion, where said SM portion expanding force decreases with an increase of said maximum value of compressive strain; and
wherein said first SM portion and second portion are selected so that said structure has a resistance to a crimping force acting to radially crimp the structure equal to one of at least 40% of a self-expansion force of said first SM portion and at least 100% of a force required to expand the structure.

* * * * *